US012344660B2

(12) United States Patent
Mauzy et al.

(10) Patent No.: US 12,344,660 B2
(45) Date of Patent: Jul. 1, 2025

(54) **CAMELIDAE SINGLE-DOMAIN ANTIBODIES AGAINST *YERSINIA PESTIS* AND METHODS OF USE**

(71) Applicant: Government of the United States as represented by the Secretary of the Air Force, Wright-Patterson AFB, OH (US)

(72) Inventors: Camilla A Mauzy, Enon, OH (US); Serge Victor Marie Muyldermans, Brussels (BE)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 0 days.

(21) Appl. No.: 18/663,247

(22) Filed: May 14, 2024

(65) Prior Publication Data
US 2024/0294616 A1    Sep. 5, 2024

Related U.S. Application Data

(63) Continuation of application No. 17/141,554, filed on Jan. 5, 2021, now Pat. No. 12,030,932, which is a continuation of application No. 16/023,723, filed on Jun. 29, 2018, now Pat. No. 11,339,208, which is a continuation of application No. 13/906,386, filed on May 31, 2013, now abandoned.

(60) Provisional application No. 61/653,488, filed on May 31, 2012.

(51) Int. Cl.
*C07K 16/12* (2006.01)
(52) U.S. Cl.
CPC .............................. *C07K 16/1228* (2013.01)
(58) Field of Classification Search
CPC .................................................. C07K 16/1228
See application file for complete search history.

*Primary Examiner* — Robert A Zeman
(74) *Attorney, Agent, or Firm* — AFMCLO/JAZ

(57) ABSTRACT

Single-domain antibodies (SAbs) against three *Yersinia pestis* surface proteins (LcrV, YscF, and F1), nucleic acid sequences encoding the SAbs, and polypeptides comprising two or more SAbs capable of recognizing two or more epitopes and/or antigens. The present invention further includes methods for preventing or treating *Y. pestis* infections in a patient; methods for detecting and/or diagnosing *Y. pestis* infections; and devices and methods for identifying and/or detecting *Y. pestis* on a surface and/or in an environment.

2 Claims, 32 Drawing Sheets
Specification includes a Sequence Listing.

```
SEQ
ID NO
154: QVQLQESGGGLVQAGGSLRLSCAASGRTWRA----YYMGWFRQAPGKEREFVAVMSRSGGTTSYADSVKG  : 66
155: QVQLQESGGGLVQAGGSLRLSCVASGRAFSN----YAMAWFRQAPGKEREFVAANWRSGGLTDYADSVKG  : 66
156: QVQLQESGGGLVQAGGSIRLSCAVSGRTFSR----YAMGWFRQAPGKEREFVAALSWSGSSTYYADSVKG  : 66
157: QVQLQESGGGLVQAGGSLKLSCTASQRTFSR----YSLGWFRQAPGEERVFVAATTWSGISSDYADSVKG  : 66
158: QVQLQESGGGLVQAGGSLRLSCAASGRTFSS----HAMAWFRQGPGEERQFLAAIRWNGDNIHYSDSAKG  : 66
159: QVQLQESGGGLVQAGDSRILSCTASGRTFGRPFRYTMGWFRRAPGKEREFVGGITRSGNNIYYSDSVKG   : 69
160: QVQLQESGGGLVQAGGSLRLACAASGETVDD----LAIGWFRQAPGKEREEISCISGSDGSTYYADSLSG  : 66

154: RFTISRDNAKNTVYLQMNNLAPEDTATYYCKAGGG---MYG-PDLYGMTYWGKGTQVTVSS
155: RFTISRDDAKNTVYLQMNSLKPEDTAVYYCAAGGGSRWYGRTTASWYDYWGQGTQVTVSS
156: RFTISRDHAKNVMYLQMNGLKPEDTGVYVCARP-----AYGLRP-PYNYRGQGTQVTVSS
157: RFTISRDNAKNTGYLQMNLKPEDTGVYYCAAGRSSWFAPWLTPYEYDYWGRGTQVTVSS
158: RFTISRDLAKNTLYLQMNSLKPEDTAVYYCARG-------------VYDYWGQGTQVTVSS
159: RFTISRDNAKNTVYLQMNSLKPEDTAVYYCNADWG-----------WRNYWGQGTQVTVSS
160: RFTISRDNVKNTVYLQMNSLKLEDTAVYCYAEIYD-----RRWYRNDYWGQGTQVTVSS
```

FIG. 10

| SEQ ID NO | | |
|---|---|---|
| 168: | QVQLQESGGGLVQAGGSLRLSCAVSGMMYIREAIRWYRQAPGKQREWVAFVSSTGN-PRYTDSVKG | : 65 |
| 169: | QVQLQESGGGLVQPGGSLRLSCAVSGMMYIRYTMRWYRQAPGKQREWVAVVSSTGN-PHYADSVKG | : 65 |
| 170: | QVQLQESGGGLVRPGGSLRLSCAVSGRAVNRYHMHWYRQAPGKQREWVTFISVGGT-TNYAGSVKG | : 65 |
| 171: | QVQLQESGGGSVQPGGSLSLSCSASGIIFSDYALTWYRQAPGKQREWVAQITRSQN-INYTGSVKG | : 65 |
| 172: | QVQLQESGGGSVQPGGSLSLSCSASGIIFSDYALTWYRQAPGKQREWVAQITRSQN-INYTGSVKG | : 65 |
| 173: | QVQLQESGGGLVQPGGSLSLSCSASGIIFSDYALTWYRQAPGKQREWVAQITRSQN-INYTGSVKG | : 65 |
| 174: | QVQLQESGGGLVQPGGSLSLSCSASGIIFSDYALTWYRQAPGKQREWVAQITRRQN-INYTGSVKG | : 65 |
| 175: | QVQLQESGGGLVQPGGSLRLSCSASGIIFSDYALTWYRQAPGKQREWVAQITRSQN-INYTGSVKG | : 65 |
| 176: | QVQLQESGGGLVQPGGSLRLSCAASARIFSIYAMVWYRQAPGKQREWVAAITTGGT-TNYADSVKG | : 65 |

| 168: | RFTISRDNAKNTVYLQMNSLTPEDTAVYYCNTYLG-SRDYWGQGTQVTVSS |
|---|---|
| 169: | RFTISRDNAKNTVYLQMNSLTPEDTAVYYCNTYLG-SRDYWGQGTQVTVSS |
| 170: | RFTVSRDNAKNTLYLQMNSLKPEDTAVYYCNS----AEYWGQGTQVTVSS |
| 171: | RFTVSRDNAKNTVHLQMNSLKPEDTAVYYCHAYDGRRPPYWGQGTQVTVSS |
| 172: | RFTVSRDNAKNTVHLQMNSLKPEDTAVYYCHAYDGRRRTYWGQGTQVTVSS |
| 173: | RFTVSRDNAKNTVHLQMNSLKPEDTAVYYCHAYDGRRPPYWGQGTQVTVSS |
| 174: | RFTVSRDNAKNTVHLQMNSLKPEDTAVYYCHAYDGRRSPYWGQGTQVTVSS |
| 175: | RFTVSRDNAKNTVHLQMNSLKPEDAAVYYCHAYDGRRPPYWGQGTQVTVSS |
| 176: | RFTVSRDNAKNTVYLQMNSLKPEDTAVYYCNAPG------YWGQGTQVTVSS |

FIG. 11A

| SEQ ID NO | | |
|---|---|---|
| 177: | QVQLQESGGGLVQPGGSLRLSCAASGVIASISVLRWYRQTPGKTRDWVAIITSGGN-TRYADSVKG | : 65 |
| 178: | QVQLQESGGGLVQPGGSLRLSCEASGTTFRSLVMKWYRQAPGKEREWVAFISSPGDRTRYTEAVKG | : 66 |
| 179: | QVQLQESGGGLVQSGDSLRLSCAASGFTFSNYAMSWVRQAPGKGLEWVSTINSGGSTSYAYSVKG | : 66 |
| 180: | QVQLQESGGGLVQPGGSLRLSCAASGFTFSNYAMSWVRQAPGKGLEWVSTINIGGSTSYADSVKG | : 66 |
| 181: | QVQLQESGGGLVQPGGSLRLSCAASGFTFRNYAMSWVRQAPGKGLEWVSTINGGSTINIAGGITSYADSVKG | : 66 |
| 182: | QVQLQESGGGLVQPGGSLRLSCAASGFTFSSYAMSWVRLAPGKGLEWVSTINIAGGITSYADSVKG | : 66 |
| 183: | QVQLQESGGGLVQPGGSLRLSCAASGFTFSSYAMSWVRQAPGKGLEWVSTINMGGGTTSYADSVKG | : 66 |
| 184: | QVQLQESGGGLVQPGGSLRLSCAASGFTFSTSAMSWIRQPPGKAREVVATITSAGGSISYVNSVKG | : 66 |
| 185: | QVQLQESGGGLVQPGGSLRLSCAASGFTFSTNAMSWIRQPPGKAREVVATITSAGGSISYVNSVKG | : 66 |

| | |
|---|---|
| 177: | RFTVSRDNARNTVYLQMNSLKPEDTAVYYCNTLVG-AKDYWGQGTQVTVSS |
| 178: | RFTVSRDNAKNALYLQMNGLKPEDTAVYYCNAN-----GIYWGKGTQVTVSS |
| 179: | RFTVSRDNAKNTLYLQMNSLKPEDTAVYYCAKTA---SHIPLSQGTQVTVSS |
| 180: | RFTVSRDNAKNTLYLQMNSLKPEDTAVYYCAKTA---SHIPLSQGTQVTVSS |
| 181: | RFTVSRDNAKNTMYLQMNSLKPEDTAVYYCAQTARDSRDSRGQGTQVTVSS |
| 182: | RFTVSRDNAKNTLYLQMNSLKPEDTAVYYCAKTAANWSAQRGQGTQVTVSS |
| 183: | RFTVSRDNAKNTLYLQMNSLKPEDTAVYYCAKTAGNWSAQRGQGTQVTVSS |
| 184: | RFTVSRDNAKNTLYLQMNMLKPEDTAVYYCARLVN---LAQTGQGTQVTVSS |
| 185: | RFTVSRDNAKNTLYLQMNMLKPEDTAVYYCARLVN---LAQTGQGTQVTVSS |

FIG. 11B

| SEQ ID NO | | |
|---|---|---|
| 204: | QVQLQESGGGMVEPGGSLRLSCAASGFRFSSYAMSWVRQAPGKGLERVSAINSDGDKTSYADSVKG | 66 |
| 205: | QVQLQESGGGLVEPGGSLRLSCAASGFRFSSYAMSWVRQAPGKGLERVSAINSDGDKTSYADSVKG | 66 |
| 206: | QVQLQESGGGMVEPGGSLRLSCAASGFRFSSYAMSWVRQAPGKGLERVSAINSDGDKTSYADSVKG | 66 |
| 207: | QVQLQESGGGLVQSGESLRLSCAASGLRFSSYAMSWVRQAPGKGLERVSAINSDGDKTSYADSVKG | 66 |
| 208: | QVQLQESGGGLVQPGGSLKLSCAASGFTFNWYTMAWYRQVPGEERKMVATITGASGDTKYADSVKG | 66 |
| 209: | QVQLQESGGGLVRPGGSLKLSCAASGFTFNWYTMAWYRQVPGEERKMVATITGASGDTKYADSVKG | 66 |
| 210: | QVQLQESGGGSVQPGGSLKLSCAASGFTFNWYTMAWYRQVPGEERKMVATITGASGDTKYADSVKG | 66 |
| 211: | QVQLQESGGGSVQPGGSLKLSCAASGFTFNWYTMAWYRQVPGEERKMVATITGASGDTKYADSVKG | 66 |
| 212: | QVQLQESGGGFVQPGGSLKLSCAASGFTFNWYTMAWYRQVPGEERKMVATITGASGDTKYADSVKG | 66 |
| 213: | QVQLQESGGGLVQPGGSLKLSCAASGLLNIYAMGWYRQAPGRQRELVATVT-SSGTAEYADSVKG | 65 |
| 214: | QVQLQESGGGLVQPGGSLGLSCAASGGTLGYYAIGWFRQAPGKKEREAVSCITSSDTSAYYADSAKG | 66 |
| 215: | QVQLQESGGGLVQPGGSLRLSCAASGFTLDIYAIGWFRQAPGKKEHEGVSWIVGNDGRTYIDSVKG | 66 |
| 216: | QVQLQESGGGLVQPGGSTRLSCAASGFTLDIYAIGWFRQAPGKKEHEGVSWIVGNDGRTYIDSVKG | 66 |
| 217: | QVQLQESGGGLVQPGGSLILSCTISGASLRDRRVTWSRQGPGKSLEIIAVMAPDYG-VHYFGSLEG | 65 |

FIG. 12A

| SEQ ID NO | |
|---|---|
| 204: | RFTISRDNARNTLYLQMSNLKPEDTAVYYCADR---DLYCSGSMCKDVLGGARYDFRGQGTQVTVSS |
| 205: | RFTISRDNARNTLYLQMSNLKPEDTAVYYCADR---DLYCSGSMCKDVLGGARYDFRGQGTQVTVSS |
| 206: | RFTISRDNARNTLYLQMNNLKPEDTAVYYCADR---DLYCSGSMCKDVLGGARYDFRGQGTQVTVSS |
| 207: | RFTISRDNARNTLYLQMSNLKPEDTAVYYCADR---DLYCSGSMCKDVLGGARYDFRGQGTQVTVSS |
| 208: | RFTISRDNAKNTVTLQMNSLKPGDAAVYYCHA---YLTYDSGSVKG----VNYWGQGTQVTVSS |
| 209: | RFTISRDNAKNTVTLQMNSLKPGDTAVYYCHA---YLTYDSGSVKG----VNYWGQGTQVTVSS |
| 210: | RFTISRDNAKNTVTLQMNSLKPGDTAVYYCHA---YLTYDSGSVKG----VNYWGQGTQVTVSS |
| 211: | RSTISRDNAKNTVTLQMNSLKPGDTAVYYCHA---CLTYDSGSVVKG----VNYWGQGTQVTVSS |
| 212: | RFTISRDNAKNTVTLQMNSLKPGDTAVYYCHA---YLTYDSGSVKG----VNYWGQGTQVTVSS |
| 213: | RFTISRDNAKNTVTLQMNSLKPGDTAVYYCHA---YLTYDSGSAKG----VNYWGQGTQVTVSS |
| 214: | RFTISRDNAKNTVYLQMNSLRPEDTGVYYCNA---HLRYG-DYVRGPPE---YNYWGQGTQVTVSS |
| 215: | RFTISRDNAKNTMYLQMNNLKPEDTAVYYCAAGYYFRDYSDSYYYTGTG---MKVWGKGTQVTVSS |
| 216: | RFTISRDNAKNTVYLEMNSLKPEDTAVYYCAAKFWPRYYSGRPPVGRDG---YDYWGQGTQVTVSS |
| 217: | RVAVRGDVVKNTVYLQVNALKPEDTAIYWCSMG----------------NIRGLGTQVTVSS |

FIG. 12B

```
SEQ
ID NO
165:  CAGGTGCAGCTGCAGGAGTCTGGGGGAGGATTGGTGCAGCCTGGGGCTCTCTGAGACTCTCCTGTGCAGCCTC
166:  CAGGTGCAGCTGCAGGAGTCTGGGGGAGGATTGGTGCAGCCTGGGGACTCTCCTGTACAGCCTC
161:  CAGGTGCAGCTGCAGGAGTCTGGGGGAGGATTGGTGCAGCCTGGGGCTCTCTGAGACTCTCCTGTGCAGCCTC
167:  CAGGTGCAGCTGCAGGAGTCTGGGGGAGGCTTGGTGCAGCCTGGGGGGTCTCTGAGACTCTCTGTGCAGCCTC

165:  TGGACGCACCTTCAGTAGCC---------ATGCCATGGCCTGGTTCCGCCAGGGTCCAGGAGAGGAGCGTCAGT
166:  TGGACGCACCCTTTGGACGCCGCCCCTTCAGATATACCATGGGCTGGTTCCGCCGGGCTCCAGGGAAGGAGCGTGAGT
161:  TGGACGCACCCTGAGAGCCT---------ATTACATGGGCTGGTTCCGCCAGGCTCCAGGGAAGGAGCGTGAGT
167:  TGGAGAGACTGTCGATGATC---------TTGCCATCGGCTGGTTCCGCCAGGCCCCAGGGAAGGAGCGTGAGG

165:  TTCTAGCAGCTATTAGATGGAATGGTGATAACATACACTATTCAGACTCCGTGAAGGGCCGATTCACCATCTCC
166:  TTGTAGGAGGTATTACAAGAAGTGGTAATAATATATACTATTCAGACTCCGTGAAGGGCCGATTCACCATCTCC
161:  TTGTAGCAGTTATGAGTCGGAGCGGTGGCACCATCCTATGCGACTCCGTGAAGGGCCGATTCACCATCTCC
167:  AGATTTCATGTATTAGTGGTAGTGGTAGCACATACTATGCACATACTATGCAGACTCCCCGTCGGGCCGATTCACCATCTCC
```

FIG. 15A

| SEQ ID NO | | | |
|---|---|---|---|
| 165: | AGAGACCTCGCCAAGAACACGCTCTATCTGCAAATGAACAGCCTGAAACCTGAGGACACGGCCGTGTATTACTG |
| 166: | AGAGACAACGCCAAGAACACGCCAAGTGTATCTCCAAATGAACAGCCTGAAACCTGAGGACACGGCCGTGTATTATTG |
| 161: | AGAGACAACGCCAAGAACACGGTGTATCTACAAATGAACAACCTGGCACCTGAGGACACGGCCACGTATTATTG |
| 167: | AGGGACAACGTCAAGAACACGTGTATCTGCAAATGAACAGCCTGAAACTTGAGGACACGGCCGTCTATTACTG |

| 165: | T---GCAAG-----------GGGGGT--GTA------------TGA-CTACTGGGCCAGGGGACC |
| 166: | TAACGCAGAT---------TGGGGGT--GGA------------GGAACTACTGGGGCCAGGGACC |
| 161: | TAAGGCGGGGGGCGGAATGTAC-GGGCCGGACCTGTA-------T-GGTATGACATACTGGGGCAAAGGGACC |
| 167: | TTATGCAGAG-----ATTTAC-GATAGACGCTGGTA-----------TCGGAACGAC-TACGGTTCCGGCCAGGGGACC |

| 165: | CAGGTCACCGTCTCCCAGCGGCCGCTACCCGTACGACGTTCCGGACTACGGTTCCGGCCGAGCATAG |
| 166: | CAGGTCACCGTCTCCCAGCGGCCGCTACCCGTACGACGTTCCGGACTACGGTTCCGGCCGAGCATAG |
| 161: | CAGGTCACCGTCTCCCAGCGGCCGCTACCCGTACGACGTTCCGGACTACGGTTCCGGCCGAGCATAG |
| 167: | CAGGTCACCGTCTCCCAGCGGCCGCTACCCGTACGACGTTCCGGACTACGGTTCCGGCCGAGCATAG |

FIG. 15B

```
SEQ
ID NO
162 : CAGGTGCAGCTGCAGGAGTCTGGAGGAGGATTGGTACAGGCTGGGGGCTCTCTGAGACTCTCCTGTGTAGCCTC
163 : CAGGTGCAGCTGCAGGAGTCTGGGGGAGGATTGGTGCAGGCTGGGGGCTCTCTGAGACTCTCCTGTGCAGTCTC
164 : CAGGTGCAGCTGCAGGAGTCTGGGGGAGGATTGGTGCAGGCTGGGGGCTCTCTGGAAACTCTCCTGCACAGCCTC

162 : TGGACGCGCCTTTCAGTAATT--------ATGCGATGGCCTGGTTCCGCCAGGCTCCAGGAAGGAGCGTGAGT
163 : TGGACGCACCTTCAGTAGAT---------ATGCCATGGGCTGGTTCCGCCAGGCTCCAGGAAGGAGCGTGAGT
164 : TCAACGCACCTTCAGTCGCT---------ATAGCTTGGGCTGGTTCCGCCAGGCTCCAGGTGAGGAGCGTGTTT

162 : TTGTAGCAGCTAATTGGCGGAGTGGTCTTACAGACTATGCAGACTCCGTGAAGGGCCGATTCACCATCTCC
163 : TTGTAGCAGCTATTAGCTGGAGTGGTAGTAGCACACATATTATGCAGACTCCGTGAAGGGCCGATTCACCATCTCC
164 : TTGTAGCCGCTACTACATGGAGTGGTATAAGCAGTGGTATGACTGACTCCGTGAAGGGCCGATTCACCATCTCC

162 : AGAGACGACGCCAAGAACACGGTGTATCTGCAAATGAACAGCCTGAAACCTGAGGACACGGCCGTTTATTACTG
163 : AGAGACCACGCCAAGAACACGGTGATGTATCTGCAAATGAACGGCCTGAAACCTGAGGACACGGGGTGTTTATGTCTG
164 : AGAGACAACGCCAAGAACACGGGTATCTGCAAATGAACAATTTAAAACCTGAGGACACGGGGCGTTTATTACTG

162 : TGCCGCCGGGGGCGGTAGTCGCTGGTACGGGCGAACAACCGCAAGTTGGTATGAC-TACTGGGCCAGGGGACC
163 : TGCA--AGACCAGCGTACGGACTCCGCCCCCG---------TATAAT-TACCGGGGCCAGGGGACC
164 : TGCAGCAGGACGTAGTCGTTGCCCTGTTCGCCCCCCCCTGTTGACCCCTATGAGTATGAT-TATTGGGGCCGGGGGGACC

162 : CAGGTCACCGTCTCCCAGCGCCCGCTACCCGTACGACGTTCCGGCCGAGCATAG
163 : CAGGTCACCGTCTCCCAGCGCCGCTACCCGTACGACGTTCCGGCCGAGCATAG
164 : CAGGTCACCGTCTCCCAGCGCCGCTACCCGTACGACGTTCCGGCCGAGCATAG
```

FIG. 15C

| SEQ ID NO | | | |
|---|---|---|---|
| 195: | CAGGTGCAGCTGCAGGAGTCTGGGGGAGGCTTGGTGCAGCCTGGGGGGTCTCTGAGACTCTCCTGTGCAGCCTC |
| 194: | CAGGTGCAGCTGCAGGAGTCTGGGGGAGGCTTGGTGCAGCCTGGGGGGTCTCTGAGACTCTCCTGTGCAGCCTC |
| 186: | CAGGTGCAGCTGCAGGAGTCTGGGGGAGGCTTGGTGCAGCCTGGGGGGTCTCTGAGACTCTCCTGTGCAGTTTC |
| 187: | CAGGTGCAGCTGCAGGAGTCTGGGGGAGGCTTGGTGCAGCCTGGGGGGTCTCTGAGACTCTCCTGTGCAGTTTC |
| 188: | CAGGTGCAGCTGCAGGAGTCTGGGGGAGGCTTGGTGCGGGCCTGGGGGGTCTCTGAGACTCTCCTGTGCAGTCTC |
| | |
| 195: | TGGAGTCATCGCCAGTATCTCCGTCCTGCGCTGGTACCGCCAAACACCAGGAAAGAGACGCGACTGGGTCGCAA |
| 194: | TGCCCGCATCTTCAGTATCTATGCCATGTATCTATGCCAGGCTCCAGGGAAGCAGCGCGAGTGGGTCGCAG |
| 186: | TGGAATGATGATGTACATTAGGGAGGCTATACGCTGGTACCGCCAGGCTCCAGGGAAGCAGCGCGAGTGGGTCGCCT |
| 187: | TGGAATGATGATGTACATTAGGTACACTATGCGCTGGTACCGCCAGGCTCCAGGGAAGCAGCGCGAGTGGGTCGCCG |
| 188: | TGGAAGAGCCGTCAATAGTATCACATGTATCACATGCACTGGTACCGCCAGGCTCCAGGGAAGCAGCGCGAGTGGGTCACAT |
| | |
| 195: | TTATTACTAG---TGGTGGCAACACACGCTATGCAGACTCCGTGAAGGGCCGATTCACCACCTCCAGAGATAAC |
| 194: | CTATTACTAC---TGGTGGTACCACAAACTATCCACGCTATACAGACTCCGTGAAGGGCCGATTCACCATCTCCAGAGACAAC |
| 186: | TTGTAAGTAG---TACTGGTAATCCACGCTATACAGACTCCGTGAAGGGCCGATTCACCATCTCCAGAGACAAC |
| 187: | TTGTAAGTAG---TACTGGTAATCCACACTATGCAGACTCCGTGAAGGGCCGATTCACCATCTCCAGAGACAAC |
| 188: | TTATTAGTGT---TGGTGGTACCACAAACTATGCAGGCTCCACACAAACTATGCAGGCTCCACCGTCTCCCGAGACAAC |

FIG. 16A

| SEQ ID NO | | | |
|---|---|---|---|
| 195: | GCCAGGAACACGGTGTATCTGCAAATGAACAGCCTGAGGACACGGCCGTCTATTACTGTAATACACT |
| 194: | GCCAAGAACACGGTGTATCTGCAAATGAACAGCCTGAGGACACGGCCGTCTATTACTGTAATGCTCC |
| 186: | GCCAAGAACACACGGTGTATCTGCAAATGAACAGCCTGACACGGCCGTCTATTACTGTAATACATA |
| 187: | GCCAAGAACACACGGTGTATCTGCAAATGAACAGCCTGAGGACACGGCCGTCTATTACTGTAATACATA |
| 188: | GCCAAAAACACGCTGTATCTGCAAATGAACAGCCTGAAACCTGAGGACACGGCCGTCTATTACTGTAATTCA-- |

| 195: | TGTAGGAGCCAA----GGACTACTGGGGCCAGGGGACCCAGGTCACCGTCTCCAGCGGCCGCTACCCGTACGAC |
| 194: | --------GGGCTACTGGGGCCAGGGGACCCAGGTCACCGTCTCCAGCGGCCGCTACCCGTACGAC |
| 186: | CTTGGGCTCGAG---GGACTACTGGGGCCAGGGGACCCAGGTCACCGTCTCCAGCGGCCGCTACCCGTACGAC |
| 187: | CTTGGGCTCGAG---GGACTACTGGGGCCAGGGGACCCAGGTCACCGTCTCCAGCGGCCGCTACCCGTACGAC |
| 188: | ----GCT--------GAATACTGGGGCCAGGGGACCCAGGTCACCGTCTCCAGCGGCCGCTACCCGTACGAC |

| 195: | GTTCCGGACTACGGTTCCGGCCGAGCATAG |
| 194: | GTTCCGGACTACGGTTCCGGCCGAGCATAG |
| 186: | GTTCCGGACTACGGTTCCGGCCGAGCATAG |
| 187: | GTTCCGGACTACGGTTCCGGCCGAGCATAG |
| 188: | GTTCCGGACTACGGTTCCGGCCGAGCATAG |

FIG. 16B

```
SEQ
ID NO
190:  CAGGTGCAGCTGCAGGAGTCTGGGGGAGGCTCGGTGCAGCCTCTCTGAGCCTCTCCTGTTCAGCCTC
189:  CAGGTGCAGCTGCAGGAGTCTGGGGGAGGCTCGGTGCAGCCTCTCTGAGCCTCTCCTGTTCAGCCTC
191:  CAGGTGCAGCTGCAGGAGTCTGGGGGAGGCTCGGTGCAGCCTCTCTGAGCCTCTCCTGTTCAGCCTC
193:  CAGGTGCAGCTGCAGGAGTCTGGGGGAGGCTTGGTGCAGCCTCTCTGAGACTCTCCTGTTCAGCCTC
192:  CAGGTGCAGCTGCAGGAGTCTGGGGGAGGCTTGGTGCAGCCTCTCTGAGCCTCTCCTGTTCAGCCTC

190:  TGGAATCATCTTCAGTGACTATGCCCTGACCTGGTACCGCCAGGCTCCAGGGAAGCAGCGCGAGTGGGTTGCAC
189:  TGGAATCATCTTCAGTGACTATGCCCTGACCTGGTACCGCCAGGCTCCAGGGAAGCAGCGCGAGTGGGTTGCAC
191:  TGGAATCATCTTCAGTGACTATGCCCTGACCTGGTACCGCCAGGCTCCAGGGAAGCAGCGCGAGTGGGTTGCAC
193:  TGGAATCATCTTCAGTGACTATGCCCTGACCTGGTACCGCCAGGCTCCAGGGAAGCAGCGCGAGTGGGTTGCAC
192:  TGGAATCATCTTCAGTGACTATGCCCTGACCTGGTACCGCCAGGCTCCAGGGAAGCAGCGCGAGTGGGTTGCAC

190:  AGATTACGCG---AAGCCAAAATATATAAATTATACAGGATCCGTGAAGGGCCGATTCACCGTCTCCAGAGACAAAC
189:  AGATTACGCG---AAGTCAAAATATATAAATTATACAGGATCCGTGAAGGGCCGATTCACCGTCTCCAGAGACAAAC
191:  AGATTACGCG---AAGCCAAAATATATAAATTATACAGGATCCGTGAAGGGCCGATTCACCGTCTCCAGAGACAAAC
193:  AGATTACGCG---AAGTCAAAATATATAAATTATACAGGATCCGTGAAGGGCCGATTCACCGTCTCCAGAGACAAAC
192:  AGATTACGCG---AAGGCAAAATATATAAATTATACAGGATCCGTGAAGGGCCGATTCACCGTCTCCAGAGACAAAC
```

FIG. 16C

| SEQ ID NO: | |
|---|---|
| 190: | GCCAAGAACACAGTGCATCTGCAAATGAACAGCCTGAAACCTGAGGACACGGCCGTCTACTATTGTCATGCATA |
| 189: | GCCAAGAACACAGTGCATCTGCAAATGAACAGCCTGAAACCTGAGGACACGGCCGTCTACTATTGTCATGCATA |
| 191: | GCCAAGAACACAGTGCATCTGCAAATGAACAGCCTGAAACCTGAGGACACGGCCGTCTACTATTGTCATGCATA |
| 193: | GCCAAGAACACAGTGCATCTGCAAATGAACAGCCTGAAACCTGAGGACACGGCCGTCTACTATTGTCATGCATA |
| 192: | GCCAAGAACACAGTGCATCTGCAAATGAACAGCCTGAAACCTGAGGACACGGCCGTCTACTATTGTCATGCATA |
| | |
| 190: | TGACGGTCGACGCC-GAACCTACTGGGCCAGGGACCCAGGTCACCGTCTCCAGCGGCCGCTACCCGTACGAC |
| 189: | TGACGGTCGACGCC-CACCCTACTGGGCCAGGGACCCAGGTCACCGTCTCCAGCGGCCGCTACCCGTACGAC |
| 191: | TGACGGTCGACGCC-CACCCTACTGGGCCAGGGACCCAGGTCACCGTCTCCAGCGGCCGCTACCCGTACGAC |
| 193: | TGACGGTCGACGCC-CACCCTACTGGGCCAGGGACCCAGGTCACCGTCTCCAGCGGCCGCTACCCGTACGAC |
| 192: | TGACGGTCGACGAT-CACCCTACTGGGCCAGGGACCCAGGTCACCGTCTCCAGCGGCCGCTACCCGTACGAC |
| | |
| 190: | GTTCCGGACTACGGTTCCGGCCGAGCATAG |
| 189: | GTTCCGGACTACGGTTCCGGCCGAGCATAG |
| 191: | GTTCCGGACTACGGTTCCGGCCGAGCATAG |
| 193: | GTTCCGGACTACGGTTCCGGCCGAGCATAG |
| 192: | GTTCCGGACTACGGTTCCGGCCGAGCATAG |

FIG. 16D

| SEQ ID NO | | | |
|---|---|---|---|
| 200: | CAGGTGCAGCTGCAGGAGTCTGGGGGAGGCTTGGTGCAACCTGGGGGGTTCTCTGAGACTCTCCTGTGCAGCCTC |
| 201: | CAGGTGCAGCTGCAGGAGTCTGGGGGAGGCTTGGTGCAACCTGGGGGGTTCTCTGAGACTCTCCTGTGCAGCCTC |
| 197: | CAGGTGCAGCTGCAGGAGTCTGGGGGAGGCTTGGTGCAATCTGGGGATTCTCTGAGACTCTCCTGTGCAGCCTC |
| 198: | CAGGTGCAGCTGCAGGAGTCTGGGGGAGGCTTGGTGCAACCTGGGGGGTTCTCTGAGACTCTCCTGTGCAGCCTC |
| 200: | TGGATTCACCTTCAGTAGCTATGAGCTGGGTCCGCCTGGCTCCAGGAAAGGGGCTCGAGTGGGTCTCAA |
| 201: | TGGATTCACCTTCAGTAGCTATGAGCTGGGTCCGCCAGGCTCCAGGAAAGGGGCTCGAGTGGGTCTCAA |
| 197: | TGGATTCACCTTCAGTAACTATGAGCTGGGTCCGCCAGGCTCCAGGAAAGGGGCTCGAGTGGGTCTCAA |
| 198: | TGGATTCACCTTCAGTAACTATGAGCTATGCCAGGCTCCAGGAAAGGGGCTCGAGTGGGTCTCAA |
| 200: | CTATTAATATCGCTGGTGGTATCACAAGCTATGCAGACTCCGTGAAGGGCCGATTCACCATCTCCAGAGACAAC |
| 201: | CTATTAATATGGGTGGTGGTACCACAAGCTATGCAGACTCCGTGAAGGGCCGATTCACCATCTCCAGAGACACAAC |
| 197: | CTATTAATAGTGGTGGTAGCACAAGCTACGCAGACTCCGTGAAGGGCCGATTCACCATCTCCAGAGACAAC |
| 198: | CTATTAATATTGGTGGTAGCACAAGCTATGCAGACTCCGTGAAGGGCCGATTCACCATCTCCAGAGACAAC |

FIG. 16E

| SEQ ID NO | | | |
|---|---|---|---|
| 200: | GCCAAGAACACGCTGTATCTGCAAATGAACAGCCTGAAACCTGAGGACACGGCCGTGTATTACTGTG-CAAAAA | CGGCGGCCCAACTGGAGCGCCCAGAGAGGCCCAGGGGACCCAGGTCACCGTCTCCCAGCGGCCGCTACCCGTACGAC | GTTCCGGACTACGGTTCCGGCCGAGCATAG |
| 201: | GCCAAGAACACGCTGTATCTGCAAATGAACAGCCTGAAACCTGAGGACACGGCCGTGTATTACTGTG-CAAAAA | CGGCGGGCAACTGGAGCGCCCAGAGAGGCCCAGGGCCAGGTCACCGTCTCCCAGCGGCCGCTACCCGTACGAC | GTTCCGGACTACGGTTCCGGCCGAGCATAG |
| 197: | GCCAAGAACACGCTGTATCTGCAAATGAACAGCCTGAAACCTGAGGACACGGCCGTGTATTACTGTG-CAAAGA | CGGCCTCTCAC----ATACCCTTGA--GCCAGGGGACCCAGGTCACCGTCACCGTCTCCCAGCGGCCGCTACCCGTACGAC | GTTCCGGACTACGGTTCCGGCCGAGCATAG |
| 198: | GCCAAGAACACGCTGTATCTGCAAATGAACAGCCTGAAACCTGAGGACACGGCCGTGTATTACTGTG-CAAAGA | CGGCCTCTCAC----ATACCCTTGA--GCCAGGGGACCCAGGTCACCGTCACCGTCTCCCAGCGGCCGCTACCCGTACGAC | GTTCCGGACTACGGTTCCGGCCGAGCATAG |

FIG. 16F

| SEQ ID NO: | |
|---|---|
| 199: | CAGGTGCAGCTGCAGGAGTCTGGGGGAGGCTTGGTGCAACCTGGGGGGTTCTCTGAGACTCTCCTGTGCAGCCTC |
| 202: | CAGGTGCAGCTGCAGGAGTCTGGGGGAGGCTTGGTGCAACCTGGGGGGTTCTCTGAGACTCTCCTGTGCAGCCTC |
| 203: | CAGGTGCAGCTGCAGGAGTCTGGGGGAGGCCTGGTGCAACCTGGGGGGTTCTCTGAGACTGTCCTGTGCAGCCTC |
| 196: | CAGGTGCAGCTGCAGGAGTCTGGGGGAGGCTTGGTGCGGGGATCTCTAAGACTCTCCTGTGAAGCCTC |
| 199: | TGGATTCACCTTCAGGAACTATGCAATGAGCTGGGTCCGTCAGGCTCCAGGAAAGGGGCTCGAGTGGGTCTCAA |
| 202: | TGGATTCACCTTCAGTACAAGTGCCATGAGTTGGATCCGCCAGCCTCCAGGGAAGGCGCGCGAGGTGGTCGCAA |
| 203: | TGGATTCACCTTCAGTACAAATGCCATGAGTTGGATCCGCCAGGCCCCAGGGAAGGCGCGCGAGGTGGTCGCAA |
| 196: | TGGAACCACCTTCAGAAGCCTCGTAATGAAATGGTACCGCCAGGCTCCAGGGAAGGAGCGCGAGTGGGTCGCAT |
| 199: | CTATTAATGGTGGTGGTGGTATCACAAGCTATGCAGACTCCGTGAAGGGCCGATTCACCATCTCCAGAGACAAC |
| 202: | CTATTACTAGTGCTGGTGGTAGTATAAGTTATGTAAACTCCGTGAAGGGCCGATTCACCATCTCCAGAGACAAAC |
| 203: | CTATTACTAGTGCTGGTGGTAGTATAAGTTATGTAAACTCCGTGAAGGGCCGATTCACCATCTCCAGAGACAAAC |
| 196: | TTATTTCTAGTCCTGGTGATCGCACTCGTACACAGAAGCCGTGAAGGGCCGATTCACCATCTCCAGAGACAAAT |

FIG. 16G

```
SEQ
ID NO
199:  GCCAAGAACACACAATGTATCTGCAAATGAACAGCCTGAAACCTGAGGACACGGCCGTCTATTACTGTG-CCCAAA
202:  GCCAAGAACACACGCTGTATCTGCAAATGAACATGCTGAAACCTGAGGACACGGCCGTGTATTACTGTG-CCCGAC
203:  GCCAAGAACACACGCTGTATCTGCAAATGAACATGCTGAAACCTGAGGACACGGCCGTGTATTACTGTG-CCCGAC
196:  GCCAAGAACGCGCTGTATCTGCAAATGAACGGCCTGAAACCTGAGGACACGGCCGTGTATTATTGTAACGCGAA

199:  CCGCCCGCGATTCCCGCGATTCCCGCGATT-----GCCCAGACCGGCCAGGGAACCCAGGTCACCGTCTCCAGCGGCCGCTACCCGTACGAC
202:  TGGTCAACCTT-----GCCCAGACCGGCCAGGGAACCCAGGTCACCGTCTCCAGCGGCCGCTACCCGTACGAC
203:  TGGTCAACCTT-----GCCCAGACCGGCCAGGGAACCCAGGTCACCGTCTCCAGCGGCCGCTACCCGTACGAC
196:  CGGAATATACT----GGGGCAAAGGGACCCAGGTCACCGTCTCCAGCGGCCGCTACCCGTACGAC

199:  GTTCCGGACTACGGTTCCGGCCGAGCATAG
202:  GTTCCGGACTACGGTTCCGGCCGAGCATAG
203:  GTTCCGGACTACGGTTCCGGCCGAGCATAG
196:  GTTCCGGACTACGGTTCCGGCCGAGCATAG
```

FIG. 16H

| SEQ ID NO | | |
|---|---|---|
| 218: | CAGGTGCAGCTGCAGGAGTCTGGGGGAGGCATGGTAGAACCTGGGGGTTCTCTGAGACTCTCCCTGTGCAGCCTC |
| 219: | CAGGTGCAGCTGCAGGAGTCTGGAGGAGGCTTGGTAGAACCTGGGGGTTCTCTGAGACTCTCCTGTGCAGCCTC |
| 220: | CAGGTGCAGCTGCAGGAGTCTGGGGGAGGCATGGTAGAACCTGGGGGTTCTCTGAGACTCTCTTGTGCAGCCTC |
| 221: | CAGGTGCAGCTGCAGGAGTCTGGGGGAGGCTTGGTGCAGTCTGGGCAGTCTCTGAGACTCTCCTGTGCAGCCTC |
| 225: | CAGGTGCAGCTGCAGGAGTCTGGGGGGGCCTGGTGCAGCCTGGGGGCTCTCTGAAACTCTCCTGTGCAGCCTC |
| | | |
| 218: | TGGATTCCGCTTCAGTAGTTATGCTATGAGTTGGGTCCGCCAGGCTCCAGGGAAAGGGGCTCGAGCGGGTCTCGG |
| 219: | TGGATTCCGCTTCAGTAGTTATGCTATGAGTTGGGTCCGCCAGGCTCCAGGGAAGCTCGAGCGGGTCTCAG |
| 220: | TGGATTCCGCTTCAGTAGTAGTTATGCTATGAGTTGGGTCCGCCAGGCTCCAGGGAAAGGGGCTCGAGCGGGTCTCGG |
| 221: | TGGACTCCGCTTCAGTAGTAGTTATGCTATGAGTTGGGTCCGCCAGGCTCCAGGGAAGGGGCTCGAGCGGGTCTCGG |
| 225: | TGGATTCACCTTCAATTGGTATACCATGGCCTGGGTATCGCCAGGTTCCAGGGAGGAGCGCAAAATGTCGCCA |
| | | |
| 218: | CTATTAATAGTGATGGTGATAAAACAAGCTATGCAGACTCCGTGAAGGGCCGATTTACCATCTCCAGAGACAAC |
| 219: | CTATTAATAGTGATGGTGATAAAACAAGCTATGCAGACTCCGTGAAGGGCCGATTTACCATCTCCAGAGACAAC |
| 220: | CTATTAATAGTGATGGTGATAAAACAAGCTATGCAGACTCCGTGAAGGGCCGATTCACCATCTCCAGAGACAAC |
| 221: | CTATTAATAGTGATGGTGATAAAACAAGCTATGCAGACTCCGTGAAGGGCCGATTTACCATCTCCAGAGACAAC |
| 225: | CAATTACAGGTGCTAGTGGTGACACAAAATATGCAGACTCCGTGAAGGGCCGTCCACCATCTCCAGAGACAAT |

FIG. 17A

| SEQ ID NO |  |
|---|---|
| 218: | GCCAGGAACACGCTGTATCTGCAAATGAGCAACCTGAAAGACACGGCCGTGTATTACTGTGCAGACCG |
| 219: | GCCAGGAACACGCTGTATCTGCAAATGAGCAACCTGAAAGACACGGCCGTGTATTACTGTGCAGACCG |
| 220: | GCCAGGAACACGCTGTATCTGCAAATGAACAACCTGAAAGACACGGCCGTGTATTACTGTGCAGACCG |
| 221: | GCCAGGAACACGCTGTATCTGCAAATGAGCAACCTGAAAGACACGGCCGTGTATTACTGTGCAGACCG |
| 225: | GCCAAGAACACGGTGACACTGCAAATGAACAGCCTTAAACCTGGAGACACGGCCGTCTATTACTGTCATGCC-- |
| 218: | AGATTTGTACTGTTCAGGCTCTCTATGTGTA-AGGACGTCTTTGG-GGGGAGCACGCTATGACTT-TCGGGGCCAGG |
| 219: | AGATTTGTACTGTTCAGGCTCTCTATGTGTA-AGGACGTCTTTGG-GGGGAGCACGCTATGACTT-TCGGGGCCAGG |
| 220: | AGATTTGTACTGTTCGGGCTCTCTATGTGTA-AGGACGTCTTTGG-GGGGAGCACGCTATGACTT-TCGGGGCCAGG |
| 221: | AGATTTGTACTGTTCAGGCTCTCTATGTGTA-AGGACGTCTTTGG-GGGGAGCACGCTATGACTT-TCGGGGCCAGG |
| 225: | -----TGCC---TAAC---CTACGACT---CGGGGTCCGT----CAAAG--GAGT-TAACTA-CTGGGGTCAGG |
| 218: | GGACCCAGGTCACCGTCTCCCAGCGGCCGCTACCCGTACGACGTTCCGGACTACGGTTCCGGCCGAGCATAG |
| 219: | GGACCCAGGTCACCGTCTCCCAGCGGCCGCTACCCGTACGACGTTCCGGACTACGGTTCCGGCCGAGCATAG |
| 220: | GGACCCAGGTCACCGTCTCCCAGCGGCCGCTACCCGTACGACGTTCCGGACTACGGTTCCGGCCGAGCATAG |
| 221: | GGACCCAGGTCACCGTCTCCCAGCGGCCGCTACCCGTACGACGTTCCGGACTACGGTTCCGGCCGAGCATAG |
| 225: | GGACCCAGGTCACCGTCTCCAGCGGCCGCTACCCGTACGACGTTCCGGACTACGGTTCCGGCCGAGCATAG |

FIG. 17B

| SEQ ID NO | |
|---|---|
| 224: | CAGGTGCAGCTGCAGGAGAGTCTGGGGGAGGCTCGGTGCAGCCTGGGGGGTCTCTGAAACTCTCCTGTGCAGCCTC |
| 223: | CAGGTGCAGCTGCAGGAGAGTCTGGGGGAGGCTTGGTGCGGCCTTGGGGGGTCTCTGAAACTCTCCTGTGCAGCCTC |
| 226: | CAGGTGCAGCTGCAGGAGAGTCTGGGGGAGGCTTCGGTGCAGCCTGGGGGGTCTCTGAAACTCTCCTGTGCAGCCTC |
| 222: | CAGGTGCAGCTGCAGGAGAGTCTGGAGGAGGCCCTGGTGCAGCCTGGGGGGTCTCTGAAACTCTCCTGTGCAGCCTC |
| 227: | CAGGTGCAGCTGCAGGAGAGTCTGGGGGAGGCCCTGGTGCAGCCTGGGGGGTCTCTGAAACTCTCCTGTGCAGCCTC |
| 224: | TGGATTCACCTTCAATTGGTATACCATGGCCTGGTATCGCCAGGTTCCAGGGGAGGAGCGCAAAATGGTTGCCA |
| 223: | TGGATTCACCTTCAATTGGTATACCATGGCCTGGTATCGCCAGGTTCCAGGGGAGGAGCGCAAAATGGTCGCCA |
| 226: | TGGATTCACCTTCAATTGGTATACCATGGCCTGGTATCGCCAGGTTCCAGGGGAGGAGCGCAAAATGGTCGCCA |
| 222: | TGGATTCACCTTCAATTGGTATACCATGGCCTGGTATCGCCAGGTTCCAGGGGAGGAGCGCAAAATGGTCGCCA |
| 227: | TGGATTCACCTTCAATTGGTATACCATGGCCTGGTATCGCCAGGTTCCAGGGGAGGAGCGCAAAATGGTCGCCA |
| 224: | CAATTACAGGTGCTAGTGGTGACACAAAATATGCAGACTCCGTGAAGGGCCGGTTCACCATCTCCAGAGACAAT |
| 223: | CAATTACAGGTGCTAGTGGTGACACAAAATATGCAGACTCCGTGAAGGGCCGGTTCACCATCTCCAGAGACAAT |
| 226: | CAATTACAGGTGCTAGTGGTGACACAAAATATGCAGACTCCGTGAAGGGCCGGTTCACCATCTCCAGAGACAAT |
| 222: | CAATTACAGGTGCTAGTGGTGACACAAAATATGCAGACTCCGTGAAGGGCCGGTTCACCATCTCCAGAGACAAT |
| 227: | CAATTACAGGTGCTAGTGGTGACACAAAATATGCAGACTCCGTGAAGGGCCGGTTCACCATCTCCAGAGACAAT |

FIG. 17C

```
SEQ
ID NO
224 : GCCAAGAACACGGTGACACTGCAAATGAACAGCCTTAAACCTGGAGACACGGCCGTCTATTACTGTCATGCC---
223 : GCCAAGAACACGGTGACACTGCAAATGAACAGCCTTAAACCTGGAGACACGGCCGTCTATTACTGTCATGCC---
226 : GCCAAGAACACGGTGACACTGCAAATGAACAGCCTTAAACCTGGAGACACGGCCGTCTATTACTGTCATGCC---
222 : GCCAAGAACACGGTGACACTGCAAATGAACAGCCTTAAACCTGGAGACACGGCCGTCTATTACTGTCATGCC---
227 : GCCAAGAACACGGTGACACTGCAAATGAACAGCCTTAAACCTGGAGACACGGCCGTCTATTACTGTCATGCC---

224 : ------TACC---TAAC----CTACGACT--CGGGGTCCGT----CAAAG--GAGT-TAACTA-CTGGGGCCAGG
223 : ------TACC---TAAC----CTACGACT--CGGGGTCCGT----CAAAG--GAGT-TAACTA-CTGGGGCCAGG
226 : ------TACC---TAAC----CTACGACT--CGGGGTCCGT----CAAAG--GAGT-TAACTA-CTGGGGCCAGG
222 : ------TACC---TAAC----CTACGACT--CGGGGTCCGT----CAAAG--GAGT-TAACTA-CTGGGGCCAGG
227 : ------TACC---TAAC----CTACGACT--CGGGGTCCGC----CAAAG--GAGT-TAACTA-CTGGGGCCAGG

224 : GGACCCAGGTCACCGTCTCCAGCGGCCGCTACCCGTACGACGTTCCGGACTACGGTTCCGGCCGCCGAGCATAG
223 : GGACCCAGGTCACCGTCTCCAGCGGCCGCTACCCGTACGACGTTCCGGACTACGGTTCCGGCCGCCGAGCATAG
226 : GGACCCAGGTCACCGTCTCCAGCGGCCGCTACCCGTACGACGTTCCGGACTACGGTTCCGGCCGCCGAGCATAG
222 : GGACCCAGGTCACCGTCTCCAGCGGCCGCTACCCGTACGACGTTCCGGACTACGGTTCCGGCCGCCGAGCATAG
227 : GGACCCAGGTCACCGTCTCCAGCGGCCGCTACCCGTACGACGTTCCGGACTACGGTTCCGGCCGCCGAGCATAG
```

FIG. 17D

| SEQ ID NO | | | | |
|---|---|---|---|---|
| 227: | CAGGTGCAGCTGCAGGAGTCTGGGGGAGGCTTGGTGCAGCCTGGGGGGTCTCTAGGACTCTCCTGTGCAGCCTC |
| 229: | CAGGTGCAGCTGCAGGAGTCTGGGGGAGGCTTGGTGCAGCCTGGGGGGTCTCTGAGACTCTCCTGTGCAGCCTC |
| 230: | CAGGTGCAGCTGCAGGAGTCTGGGGGAGGCTTGGTGCAGCCTGGGGGGTCTCGGACTCTCCTGTGCAGCCTC |
| 231: | CAGGTGCAGCTGCAGGAGTCTGGGGGAGGCTTGGTGCAGCCTGGGGGTCTCTGATACTCTCCTGTACAATCTC |
| 227: | TGGAAGCCTCTCTTAAATATCTATGCCATGGGCTGGTACCGCCAGGCTCCAGGGAGACAGCGCGAGTTGGTCGCAA |
| 229: | TGGAGGCACTTTGGGTTACTATGCCATAGGCTGGTTCCGCCAGGCTGGTTCCGCCAGGGAAGGAGGCGAGGCGGGTCTCCT |
| 230: | TGGATTCACTTTTGGATATATTTATGCTATAGGCTGGTTCCGCCAGGCTGGTTCCGCCAGGGAAGGAGGAGCATGAGGGGGTCTCGT |
| 231: | GGGAGCCTCGCTCCCGAGACCGACGCGTCACCTGGAGTCGCCAAGGTCGCCAGGGAAATCGCTTGAGATCATCGCAG |
| 227: | CTGTAACGAGT---AGTGGAACCGCAGAATATGCAGACTCCCGTGAAGGGCCGATTCACCATCTCTAGAGACAAC |
| 229: | GTATTACTAGTAGTGACACTAGCGCATACTATGCAGACTCCGCGAAGGGCCGATTCACCATCTCCAGAGACAAC |
| 230: | GGATTGTTGGTAATGATGGTAGGACATATAGACTCCGTGAAGGGCCGATTCACCATCTCCAGAGACAAC |
| 231: | TTATGGCGCCG---GATTACGGGGTCCATTACTTTGGCTCCCTGGAGGGCGAGTTGCCGTCCGAGGAGACGTC |

FIG. 17E

```
SEQ
ID NO
227:  GCCAAGAACACGGTGTATCTGCAAATGAACAGCCTGAGACCTGAGGACACGGGCGTCTATTACTGTAATGCA--
229:  GCCAAGAACACGATGTATCTGCAAATGAACAACCTGAGGACAACCTGAAAACCTGAGGACACAGCCCGTTTATTACTGTGCAGCCGG
230:  GCCAAGAACACGGTGTATCTGTGTATCTTGAAATGAACAGCCTGAGGATACAGCCGTTTATTACTGCGCAGCTAA
231:  GTCAAGAATACAGTATATCTCCAAGTAAACGCCCTGAAACCTGAAAACACAGCCATCTATTGGTGCAG------

227:  ------CATC---TCAG----ATATGGCGA-CTATGTCCGTGGCCCTCCG--GAGTATAACTA-CTGGGCCAGG
229:  ---TTACTATT---TTAGAGACTATAGTGA-CAGTTACTACACGGGACGGGTATGAAAGTCTGGGGCAAAG
230:  ----GTTCTGGCCCCGATATTATAGTGGTAGGCCTCCAGTAGGGAGGGATGGCTATGACTA-TTGGGCCAGG
231:  --------------TATGGGG---------------------AATATCCGGGCCTGG

227:  GGACCCAGGTCACCGTCTCCCAGCGGCCGCTACCCGTACGACGTTCCGGACTACGGTTCCGGCCGAGCATAG
229:  GGACCCAGGTCACCGTCTCCCAGCGGCCGCTACCCGTACGACGTTCCGGACTACGGTTCCGGCCGAGCATAG
230:  GGACCCAGGTCACCGTCTCCCAGCGGCCGCTACCCGTACGACGTTCCGGACTACGGTTCCGGCCGAGCATAG
231:  GGACCCAGGTCACCGTCTCCCAGCGGCCGCTACCCGTACGACGTTCCGGACTACGGTTCCGGCCGAGCATAG
```

FIG. 17F

CAMELIDAE SINGLE-DOMAIN ANTIBODIES AGAINST *YERSINIA PESTIS* AND METHODS OF USE

CROSS-REFERENCE TO RELATED APPLICATIONS

This application is a continuation of U.S. application Ser. No. 17/141,554, filed Jan. 5, 2021, which was a continuation of U.S. application Ser. No. 16/023,723, filed Jun. 29, 2018, now U.S. Pat. No. 11,339,208 issued May 24, 2022, which was a continuation of U.S. application Ser. No. 13/906,386, filed May 31, 2013, which claimed the benefit of and priority to U.S. Provisional Application No. 61/653,488, filed on May 31, 2012. The disclosure of each application is incorporated herein by reference, in its entirety.

RIGHTS OF THE GOVERNMENT

The invention described herein may be manufactured and used by or for the Government of the United States for all governmental purposes without the payment of any royalty.

REFERENCE TO AN ELECTRONIC SEQUENCE LISTING

The contents of the electronic sequence listing (AFD-1216CON8 Sequence Listing.xml; Size: 307 KM; and Date of Creation: May 13, 2024) is herein incorporated by reference in its entirety.

FIELD OF THE INVENTION

This invention relates generally to the field of single-domain antibodies. More particularly, it relates to single-domain antibodies and polypeptides against *Yersinia pestis*, nucleic acid sequences encoding the single-domain antibodies, and methods of using the same.

BACKGROUND OF THE INVENTION

Increasing threats of bioterrorism have led to the development of new diagnostic and therapeutic tools for pathogens that can potentially be used as biological weapons. Many of these pathogens, such as the causative agents of plague, anthrax, and tularemia, are relatively easy to manipulate via genetic engineering and may be designed to evade detection by sensor devices. Many of these biological weapons candidates also display resistance to current medical treatments. To be useful, a diagnostic tool must be sensitive and specific, as well as able to withstand the extreme conditions often encountered in the field. The value of a therapeutic tool is largely determined by parameters such as toxicity, immunogenicity, and efficacy after administration. In addition, the therapeutic tool may be required to treat large number of people in the event of a bioterrorism attack. All of these requirements highlight the importance of a long shelf life and the production costs of biological weapon-related diagnostics and therapeutics.

Members of the family Camelidae, which includes alpacas, camels, and llamas, produce conventional antibodies, as well as antibodies consisting only of a dimer of heavy-chain polypeptides. The N-terminal domain of these heavy chain-only antibodies, which is referred to as VHH, is variable in sequence, and it is the sole domain that interacts with the cognate antigen. Because of their small size (12-15 kDa, 2.2 nm diameter, and 4 nm height), VHHs are also known as single-domain antibodies (SAbs), which are commercially-available as NANOBODIES (NANOBODY and NANOBODIES are registered trademarks of Ablynx N.V., Belgium).

SAbs make attractive as tools for biological weapon detection due to their high affinity and specificity for their respective targets and their high stability and solubility. Their small size gives SAbs the unique ability to recognize and bind to areas of an antigen that are often not normally accessible to full-size antibodies due to steric hindrance and other size constraints. In addition, SAbs may be economically produced in large quantities, and their sequences are relatively easy to tailor to a specific application. These properties, as well as their low immunogenicity, make SAbs uniquely suited for detection, diagnostics, and immunotherapeutics.

SUMMARY OF THE INVENTION

The present invention includes a composition comprising at least one single-domain antibody against one or more *Yersinia pestis* (*Y. pestis*) surface proteins, in which the one or more *Y. pestis* surface proteins are selected from the group consisting of YscF, F1, and LcrV, with each single-domain antibody comprising four framing regions (FRs) and three complementarity determining regions (CDRs), in which the at least one single-domain antibody is selected from the group consisting of: (1) at least one single-domain antibody comprising one CDR1 sequence selected from the group consisting of SEQ ID NOs:1-7, one CDR2 sequence selected from the group consisting of SEQ ID NOs:27-33, and one CDR3 sequence selected from the group consisting of SEQ ID NOs:54-60; (2) at least one single-domain antibody comprising one CDR1 sequence selected from the group consisting of SEQ ID NOs:8-19, one CDR2 sequence selected from the group consisting of SEQ ID NOs:34-47, and one CDR3 sequence selected from the group consisting of SEQ ID NOs:61-71, AEY, and PGY; and (3) at least one single-domain antibody comprising one CDR1 sequence selected from the group consisting of SEQ ID NOs:20-26, one CDR2 sequence selected from the group consisting of SEQ ID NOs:48-53, and one CDR3 sequence selected from the group consisting of SEQ ID NOs:72-78 and GNI, with the four framing regions of each single-domain antibody comprising one FR1 sequence selected from the group consisting of SEQ ID NOs:79-102, one FR2 sequence selected from the group consisting of SEQ ID NOs:103-120, one FR3 sequence selected from the group consisting of SEQ ID NOs:121-146, and one FR4 sequence selected from the group consisting of SEQ ID NOs:147-153.

In one embodiment, the at least one single-domain antibody is selected from the group consisting of SEQ ID NOs:154-160, 168-185, and 204-217. In a further embodiment, the at least one single-domain antibody further comprises at least one of a protein tag, a protein domain tag, or a chemical tag.

In one embodiment, the composition comprises a plurality of single-domain antibodies against a single *Y. pestis* surface protein. In another embodiment, at least a portion of the plurality of single-domain antibodies is against different epitopes on the single *Y. pestis* surface protein. In another embodiment, the composition comprises a plurality of single-domain antibodies against at least two *Y. pestis* surface proteins.

In an alternative embodiment, the composition comprises a plurality of single-domain antibodies further comprising a polypeptide. In one embodiment, the plurality of single-domain antibodies comprising the polypeptide are against a single *Y. pestis* surface protein. In another embodiment, at least a portion of the plurality of single-domain antibodies comprising the polypeptide are against different epitopes on the single *Y. pestis* surface protein. In another embodiment, the plurality of single-domain antibodies comprising the polypeptide are against at least two *Y. pestis* surface proteins.

In a further embodiment, the polypeptide comprises a fusion protein. In another embodiment, the polypeptide comprises a multivalent protein complex, with the single-domain antibodies being joined together with at least one linker molecule. In a further embodiment, at least one of the plurality of single-domain antibodies comprising the polypeptide further comprises at least one of a protein tag, a protein domain tag, or a chemical tag.

The present invention further includes at least one isolated nucleotide sequence encoding the at least one single-domain antibody, wherein the at least one isolated nucleotide sequence is selected from the group consisting of SEQ ID NOs:164-170, 189-206, and 221-234.

BRIEF DESCRIPTION OF THE DRAWINGS

FIGS. 9A-B are graphs graph of the ELISA for the presence of LcrV-specific SAbs in the periplasmic extract of positive colonies.

FIG. 10 is a protein sequence alignment of seven exemplary YscF SAbs according to the present invention.

FIGS. 11A-B are protein sequence alignments of eighteen exemplary F1 SAbs according to the present invention.

FIGS. 12A-B are the protein sequence alignment of fourteen exemplary LcrV SAbs according to the present invention.

FIGS. 15A-C are sequence alignments of nucleic acid sequences encoding the exemplary YscF SAbs according to the present invention.

FIGS. 16A-H are sequence alignments of nucleic acid sequences encoding the exemplary F1 SAbs according to the present invention.

FIGS. 17A-F are sequence alignments of nucleic acid sequences encoding the exemplary LcrV SAbs according to the present invention.

DETAILED DESCRIPTION OF THE INVENTION

Figure 1:
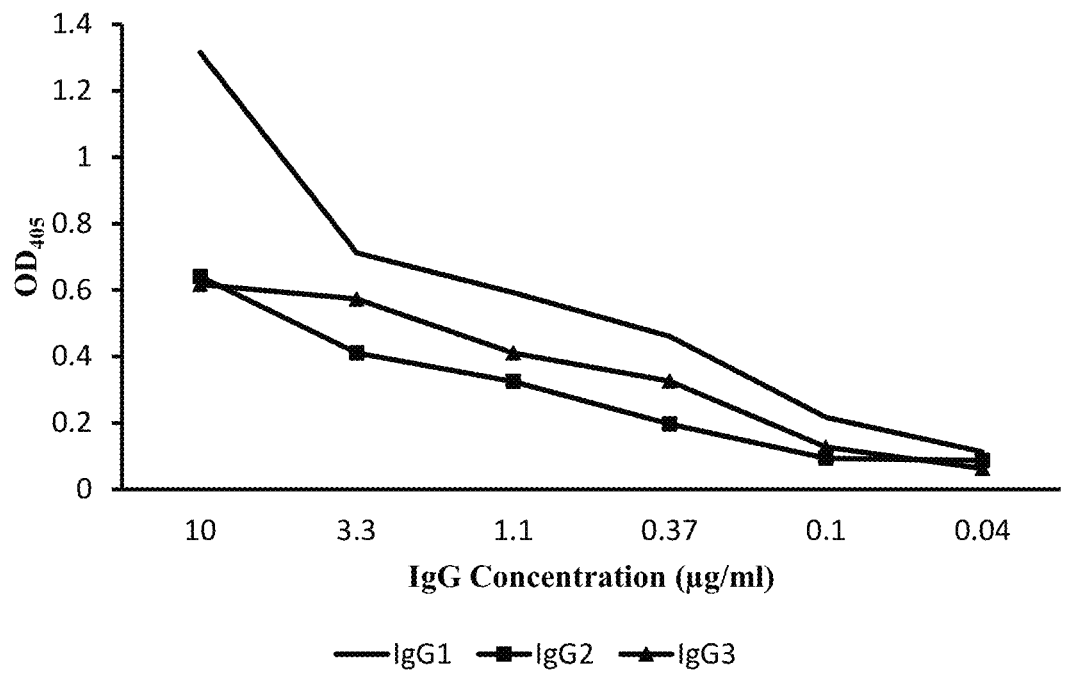
FIG. 1 is a graph of the binding response of IgG isolated from an immune alpaca to *Y. pestis* YscF (ELISA).

The present invention includes single-domain antibodies (SAbs) against three *Yersinia pestis* (*Y. pestis*) surface proteins (LcrV, YscF, and F1), the nucleic acids encoding the SAbs, and polypeptides comprising two or more SAbs capable of recognizing one or more *Y. pestis* surface proteins or epitopes. The present invention further includes methods for preventing or treating *Y. pestis* infections in a patient; methods for detecting and/or diagnosing *Y. pestis* infections; and devices and methods for identifying and/or detecting *Y. pestis* on a surface and/or in an environment.

*Y. pestis*, the gram-negative *Bacillus* that causes plague, is considered a Class A biological weapon. *Y. pestis* infections occur in three different ways: infection of the lymph nodes (bubonic), the lungs (pneumonic), or the blood (septicemic). The most serious, contagious, and often fatal mode of plague is pneumonic plague, which may be caused by inhalation of contaminated respiratory droplets from another infected person or from intentional release of aerosolized plague pathogen. While *Y. pestis* infections are treatable with antibiotics, diagnosis and treatment are often delayed. In the case of pneumonic plague, the early symptoms such as fever, headache, and nausea may easily be mistaken for more common illnesses, delaying proper diagnosis and treatment during the early stages of the disease and greatly increasing the chances of death. Untreated pneumonic plague has a mortality rate of almost 100%. In the case of battlefield personnel and persons stationed or living in rural areas, access to proper health care may be further limited by distance and availability.

Of particular interest for detection and treatment are three *Y. pestis* surface proteins, LcrV, YscF, and F1. LcrV is a 37 kDa virulence factor that is secreted and expressed on the *Y. pestis* cell surface prior to bacterial interaction with host cells, making it an excellent antigenic protein for antibody capture. It has been shown that anti-LcrV antibodies can block the delivery of Yops, a set of virulence proteins exported into the host cell upon contact. Additionally, it has been shown that a single sensitive, specific antibody could be used to capture LcrV from *Y. pestis, Y. pseudotuberculosis*, and *Y. enterocolitica*. The functional determination of LcrV provides a possible reason for the success of anti-LcrV Ab immunotherapeutics as it is hypothesized that the anti-LcrV/Ab complex prevents the formation and function of the tip complex, thus interfering with the translocation of virulent Yops critical to infection. YscF has also been implicated as one of the "needle" proteins involved in T3SS injection of the virulent Yops proteins across eukaryotic membranes upon cell contact. Recent work using purified YscF to initiate an active immune response indicates that YscF-vaccinated mice have significant protection to a *Y. pestis* challenge. As with LcrV, these data indicate that YscF is an excellent antigen target for immunotherapeutic uses. F1 protein, which is a *Y. pestis* capsule protein, has likewise been identified as a potential therapeutic target and is one of the principal immunogens in currently available plague vaccines. Among other roles, F1 is thought to be involved in preventing *Y. pestis* uptake by macrophages.

SAbs in general, including the presently disclosed *Y. pestis* SAbs, comprise four framework regions (FRs) interrupted by three complementarity determining regions (CDRs) to yield the following general structure:

FR1-CDR1-FR2-CDR2-FR3-CDR3-FR4.

Like many SAbs, the CDR3 sequence of the presently disclosed *Y. pestis* SAbs is generally the most crucial in determining antigen specificity. SAbs directed against a particular antigen generally demonstrate some degree of homology or sequence identity between each FR and CDR. Where two nucleotide or amino acid sequences are the same length when aligned, the term "sequence identity" as used herein relates to the number of positions with identical nucleotides or amino acids divided by the total number of nucleotides or amino acids. The number of identical nucleotides or amino acids is determined by comparing corresponding positions of a designated first sequence (usually a reference sequence) with a second sequence. Where two nucleotide or amino acid sequences are of different length when aligned, the term "sequence identity" as used herein relates to the number of positions with identical nucleotides or amino acids divided by the number of nucleotides or amino acids in the designated or reference sequence. Any addition, deletion, insertion, or substitution of a nucleotide or amino acid is considered a difference when calculating the sequence identity. The degree of sequence identity may also be determined using computer algorithms, such algorithms may include, for example, commercially-available Basic Local Alignment Search Tool, also known as BLAST (U.S. National Library of Medicine, Bethesda, MD).

*Y. pestis* SAbs according to the present invention may be used as components of in vivo and in vitro assays and may also be used diagnostic testing and imaging. The generally low toxicity and immunogenicity of SAbs further makes the present *Y. pestis* SAbs promising active and passive immunotherapeutic tools, particularly for self-administered fieldable therapeutics. In the case of an outbreak or a biological weapon attack, a self-administered treatment could provide sufficient temporary immunity and sufficiently slow the onset and progress of the disease to allow a person exposed to *Y. pestis* to reach a hospital for diagnosis and treatment. The SAbs may be introduced by any suitable method including intravenous and subcutaneous injection, oral ingestion, inhalation, and topical administration. The SAbs may bind to extracellular epitopes and antigens and may also bind to intracellular targets after introduction into the host cell by phagocytosis or other mechanisms. In addition, the *Y. pestis* SAbs may be useful for decontamination and as field-stable capture elements for real-time biological weapon detection and quantitation.

Many of the presently disclosed *Y. pestis* SAbs demonstrate full functionality and high affinity for their respective antigen targets, which is likely due to the ability of SAbs to bind to protein clefts that are often inaccessible to larger, conventional antibodies. This ability to access areas located in interior pockets may allow therapeutic and detection tools based on the present *Y. pestis* SAbs to detect multiple strains of the pathogen, as well as related organisms in the *Yersinia* genus. SAb-based tools and techniques may also be less susceptible to genetic engineering of pathogen surface proteins and epitopes designed to elude current detectors and to circumvent immunity conferred by conventional vaccination.

The *Y. pestis* SAbs according to the present invention may be quickly, easily, and inexpensively produced in large quantities in a bacterial expression system such as *E. coli* with little or no loss of protein activity and little or no need for post-translational modification. In addition, the SAbs are stable within a wide range of temperature, humidity, and pH. This stability may allow for stockpiling and long-term storage of the SAbs and SAb-based detection, diagnostic, and therapeutic tools in preparation for *Y. pestis* outbreaks and/or a bioterrorism attack, all without the need for costly climate control and/or monitoring. The stability of SAbs in extreme environments may further allow for reusable sensors and detection devices.

The following examples and methods are presented as illustrative of the present invention or methods of carrying out the invention, and are not restrictive or limiting of the scope of the invention in any manner. Amino acid residues will be according to the standard three-letter or one-letter amino acid code as set out in Table 1. The materials and methods used in Examples 1-4 are described, for example, in *Antibody Engineering*, Eds. R. Kontermann & S. Dübel, Springer-Verlag, Berlin Heidelberg (2010) Isolation of antigen-specific Nanobodies, Hassanzadeh Ghassabeh Gh., et al., Vol. 2, Chapter 20, pp. 251-266. Exemplary combinations of individual FR and CDR regions are shown in Table 2, and complete SAb protein sequences isolated according to the following Examples are listed in Tables 3, 5, and 7. Unique sequences (individual CDRs and FRs and complete SAb sequences) are each assigned a SEQ ID NO; sequences comprising less than four amino acids are not assigned a SEQ ID NO. As seen in FIGS. 10-12, some SAbs share 100% sequence identity in one or more CDRs and/or FRs because the SAbs are either from clonally-related B-cells or from the same B-cell with diversification due to PCR error during library construction.

Example 1

Antibody Development and Construction of a VHH Library

Figure 2:
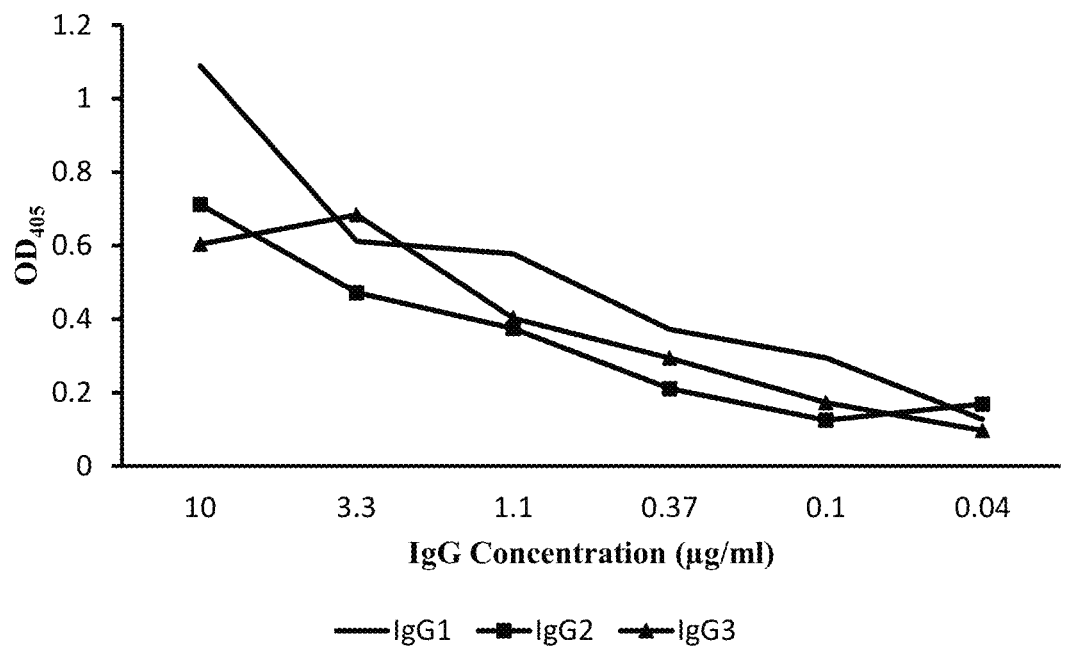
FIG. 2 is a graph of the binding response of IgG isolated from an immune alpaca to *Y. pestis* F1 (ELISA).
Figure 3:
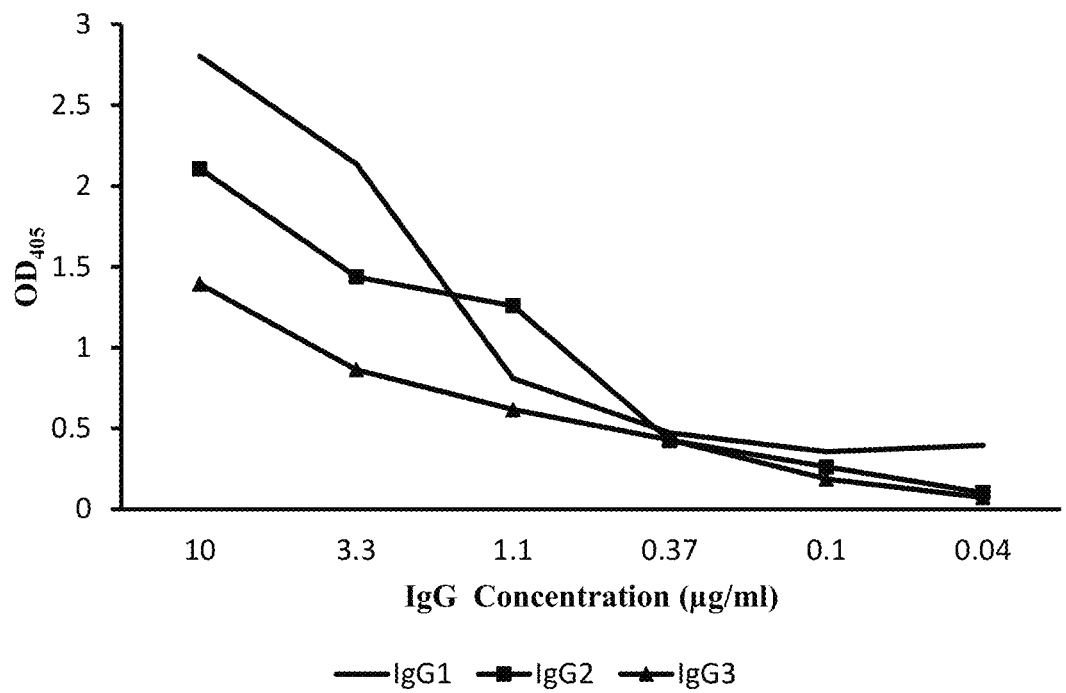
FIG. 3 is a graph of the binding response of IgG isolated from an immune alpaca to *Y. pestis* LcrV (ELISA).

All SAbs were developed using proteins (antigen) expressed from genes isolated from *Y. pestis* KIM5 (avirulent pgm−), which is similar in sequence to the same protein set in *Y. pestis* virulent strains (pgm+). An alpaca was injected subcutaneously on days 0, 7, 14, 21, 28 and 35, each time with about 165 µg YscF antigen, about 160 µg F1 antigen, and about 160 µg LcrV antigen. The same animal may be used for all experiments, but multiple animals may also be used. On day 39, anticoagulated blood was collected from the alpaca for the preparation of plasma and peripheral blood lymphocytes. Using plasma from the immune animal, IgG subclasses were obtained by successive affinity chromatography on protein A and protein G columns and were tested by ELISA to assess the immune response to YscF, F1, and LcrV antigens. FIGS. 1-3 are graphs of the immune response to YscF, F1, and LcrV, respectively, in both conventional (IgG1) and heavy chain (IgG2 & IgG3) antibodies. As seen in FIGS. 1-3, the IgG isolated from the immune animal exhibited a strong response toward all three antigens in both types of antibody.

A VHH library was then constructed and screened for the presence of SAbs specific to YscF, F1, and LcrV. Total RNA was extracted from peripheral blood lymphocytes isolated from the immune alpaca and used as a template for first strand cDNA synthesis with oligo(dT) primer. Using this cDNA, the VHH encoding sequences were amplified by PCR and cloned into the phagemid vector pHEN4. pHEN4 vectors containing the amplified VHH sequences were transformed into electrocompetent cells to obtain a VHH library of about 1-2×10$^8$ independent transformants. About 75-93% of transformants harbored vectors with the correct insert sizes. Antigen-specific SAbs were then selected from a phage display library.

Example 2

Isolation of YscF SAbs

Figure 4:
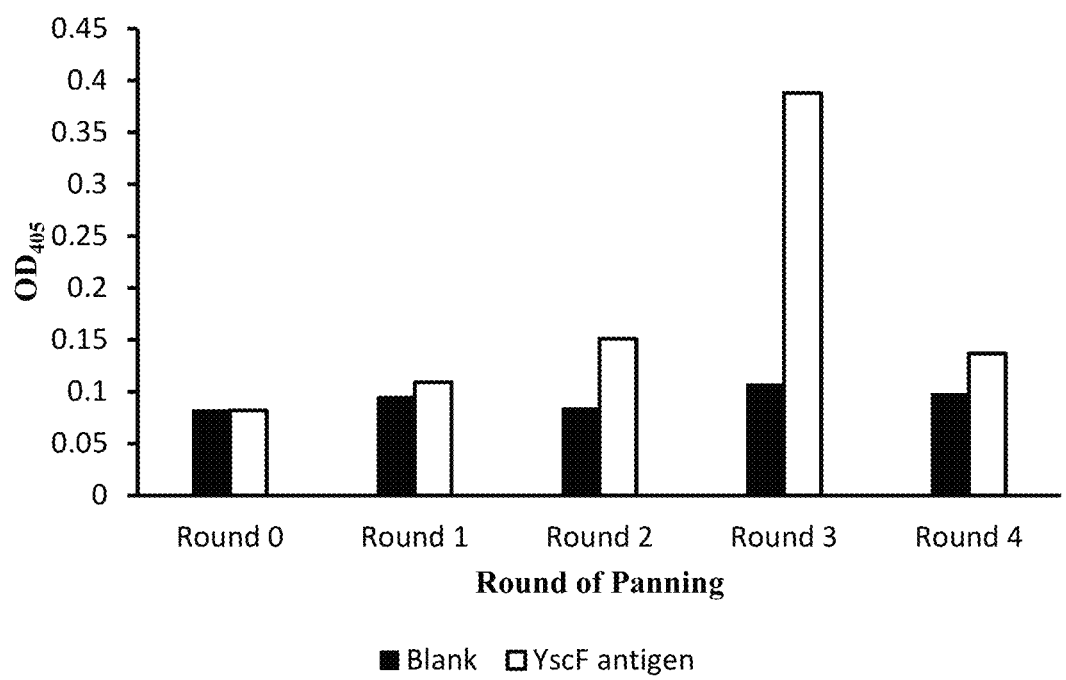
FIG. 4 is a graph of polyclonal phage ELISA testing after each round of panning to isolate YscF-specific phages.
Figure 5:
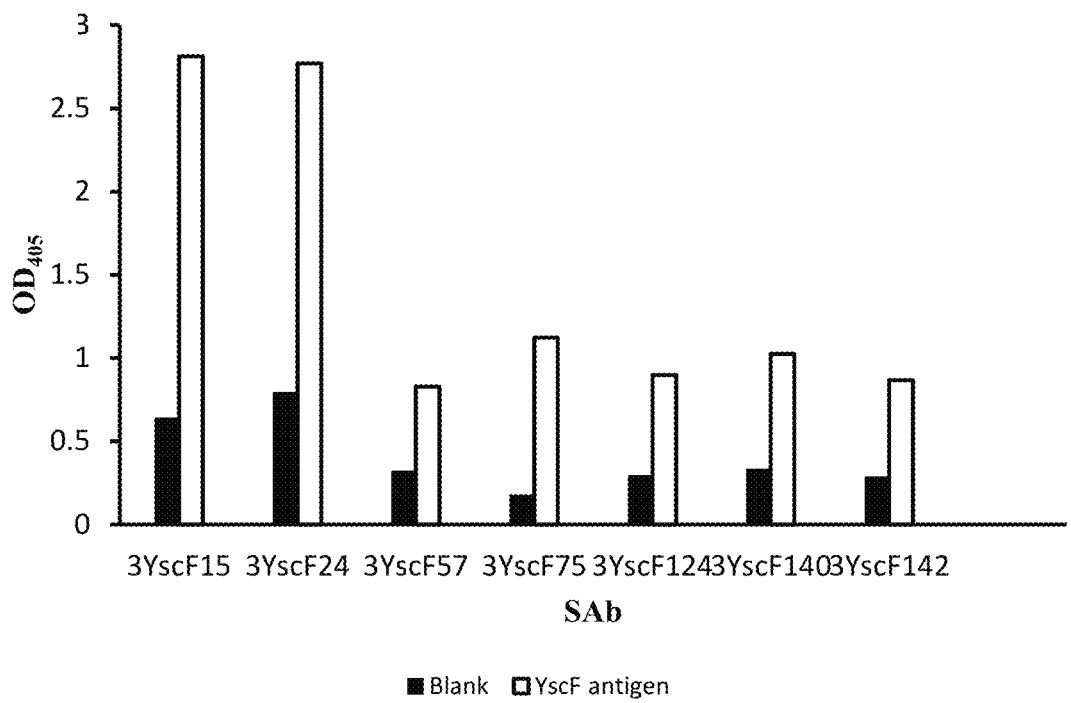
FIG. 5 is a graph of the ELISA for the presence of YscF-specific SAbs in the periplasmic extract of positive colonies.

For the YscF antigen, the VHH library was subjected to four consecutive rounds of panning, performed on solid-phase coated antigen (concentration: 700 µg/ml, 30 µg/well, in 25 mM Tris (pH not tested), 150 mM NaCl, 0.05% Tween-20, and 1 mM EDTA). The enrichment for antigen-specific phages after each round of panning was assessed by comparing the number of phages eluted from antigen-coated wells with the number of phages eluted from negative control (only blocked) wells. The enrichment was also evaluated by polyclonal phage ELISA, which is shown in FIG. 4. These experiments suggested that the phage population was enriched for antigen-specific phages only after the third round of panning. In total, 385 individual colonies (95, 143, and 47 from second, third, and fourth rounds, respectively) were randomly selected and analyzed by ELISA for the presence of YscF-specific SAbs in their periplasmic extracts. Out of these 385 colonies, 19 colonies (all from the third round) scored positive. Sequencing of positive colonies identified seven different SAbs, and the ELISA results for these seven SAbs are shown in FIG. 5. The protein sequences of the seven exemplary YscF SAbs according to the present invention are shown in Table 3, and the nucleic acid sequences encoding the seven exemplary YscF SAbs are shown in Table 4.

FIG. 10 is a protein sequence alignment of the seven exemplary YscF SAbs listed in Table 3, and FIGS. 15A-C are sequence alignments of the nucleic acid sequences listed in Table 4. Gaps are introduced in the sequences contained in FIGS. 10 and 15A-C as needed in order to align the respective protein and nucleic acid sequences with one another. Referring to FIG. 10, the three CDRs are underlined in each sequence. The CDRs are defined according to the Kabat numbering system [Kabat, E. A., et al., (1991) Sequences of Proteins of Immunological Interest, Fifth Edition, NIH Publication No. 91-3242, US Department of Health and Human Services, Bethesda, MD]. The differences in the four FRs of each SAb (if any), as compared with 3YscF57 (SEQ ID NO:154), are in bold; any differences between the three CDRs of each SAb are not otherwise indicated. The seven exemplary YscF SAb sequences depicted in FIG. 10 and listed in Table 3 represent seven different groups i.e. they originate from seven clonally-unrelated B-cells.

Example 3

Isolation of F1 SAbs

Figure 6:
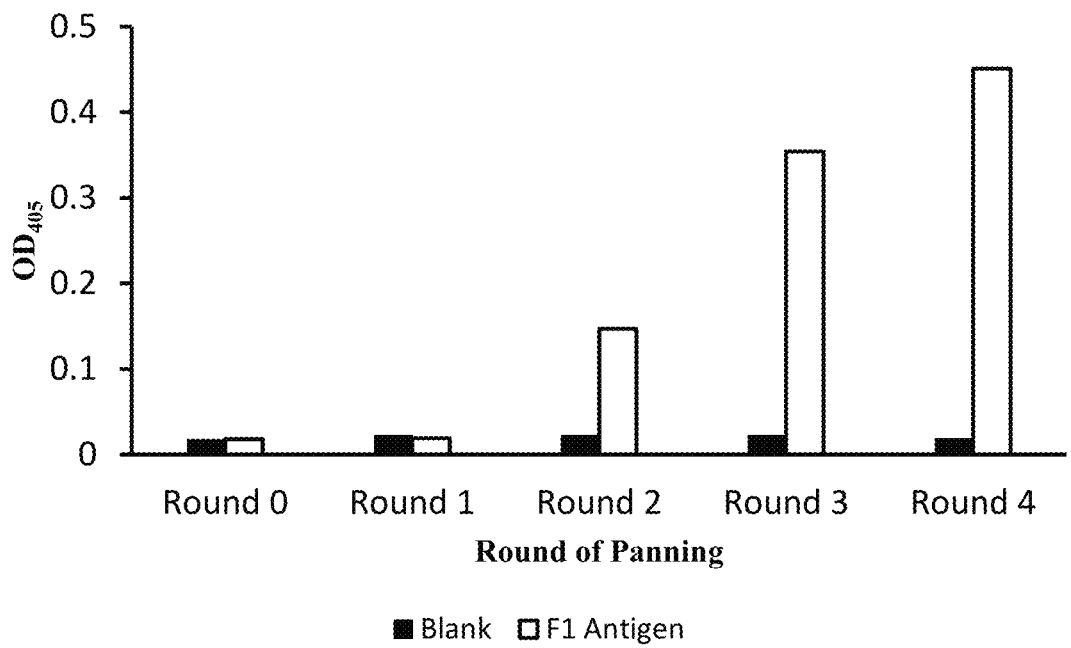
FIG. 6 is a graph of polyclonal phage ELISA testing after each round of panning to isolate F1-specific phages.
Figure 7A:
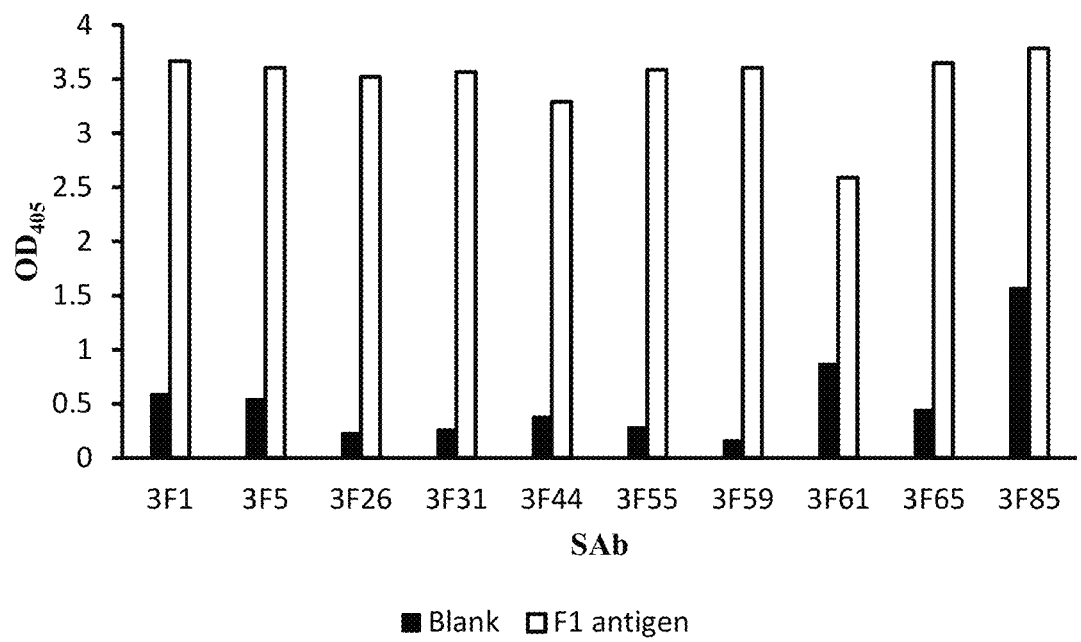
FIGS. 7A-B are graphs of the ELISA for the presence of F1-specific SAbs in the periplasmic extract of positive colonies.
Figure 7B:
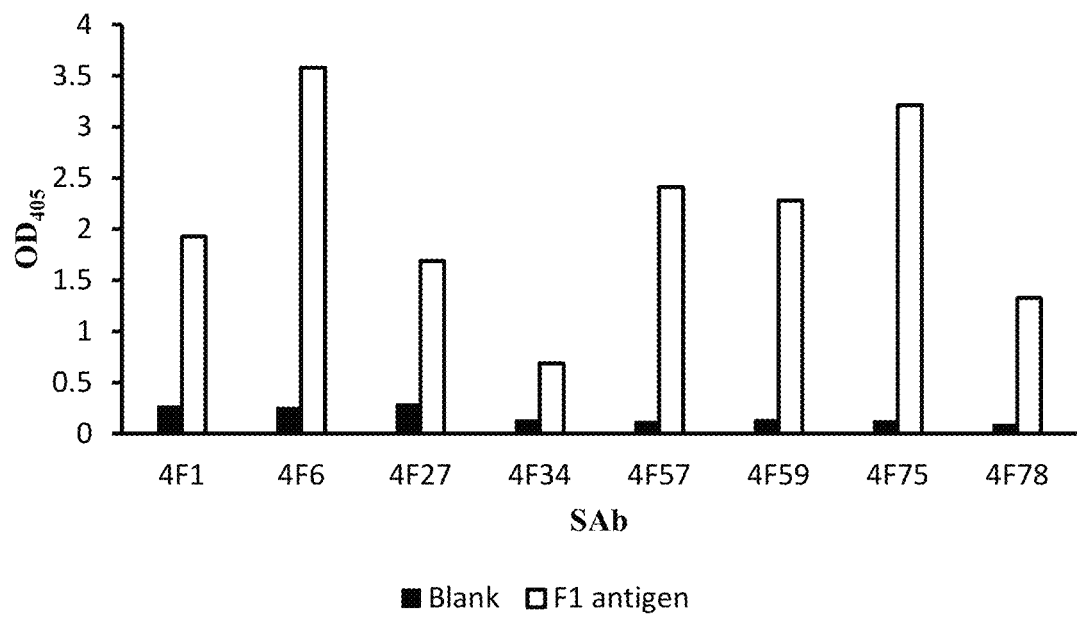

For the F1 antigen, the library was subjected to four consecutive rounds of panning, performed on solid-phase coated antigen (concentration: 200 µg/ml, 20 µg/well, in the presence of 0.005% Tween-20). The enrichment for antigen-specific phages after each round of panning was assessed by comparing the number of phages eluted from antigen-coated wells with the number of phages eluted from negative control (blocked only) wells. The enrichment was also evaluated by polyclonal phage ELISA, which is shown in FIG. 6. These experiments suggested that the phage population was enriched for antigen-specific phages only after the third and fourth rounds of panning. In total, 285 individual colonies from second, third, and fourth rounds of panning (95 from each round) were randomly selected and analyzed by ELISA for the presence of F1-specific SAbs in their periplasmic extracts. Out of these 285 colonies, 55 scored positive (0, 29, and 26 from second, third, and fourth rounds, respectively). Sequencing of these 55 positive colonies identified 18 different SAbs, and the ELISA results for these 19 SAbs are shown in FIGS. 7A-B. The protein sequences of 18 exemplary F1 SAbs according to the present invention are shown in Table 5, and the nucleic acid sequences encoding the 18 F1 SAbs are shown in Table 6.

FIGS. 11A-B are protein sequence alignments of the 18 exemplary F1 SAbs listed in Table 5, and FIGS. 16A-H are sequence alignments of the nucleic acid sequences listed in Table 6. Gaps are introduced in the sequences in FIGS. 11A-B and 16A-H as needed in order to align the protein and nucleic acid sequences with one another. Referring to FIGS. 11A-B, the three CDRs are underlined in each sequence. The CDRs are defined according to the Kabat numbering system. The differences in the four FRs of each SAb (if any), as compared with 3F55 (SEQ ID NO:168), are in bold; any differences between the three CDRs of each SAb are not otherwise indicated. The 18 exemplary F1 SAbs shown in FIGS. 11A-B and listed in Table 5 represent 10 different groups, which are listed in Table 9. SAbs belonging to the same group are very similar, especially in the CDR3 region, and their amino acid sequences suggest that they are either from clonally-related B-cells resulting from somatic hyper-mutation or from the same B-cell with diversification due to PCR error during library construction.

Example 4

Isolation of LcrV SAbs

Figure 8:
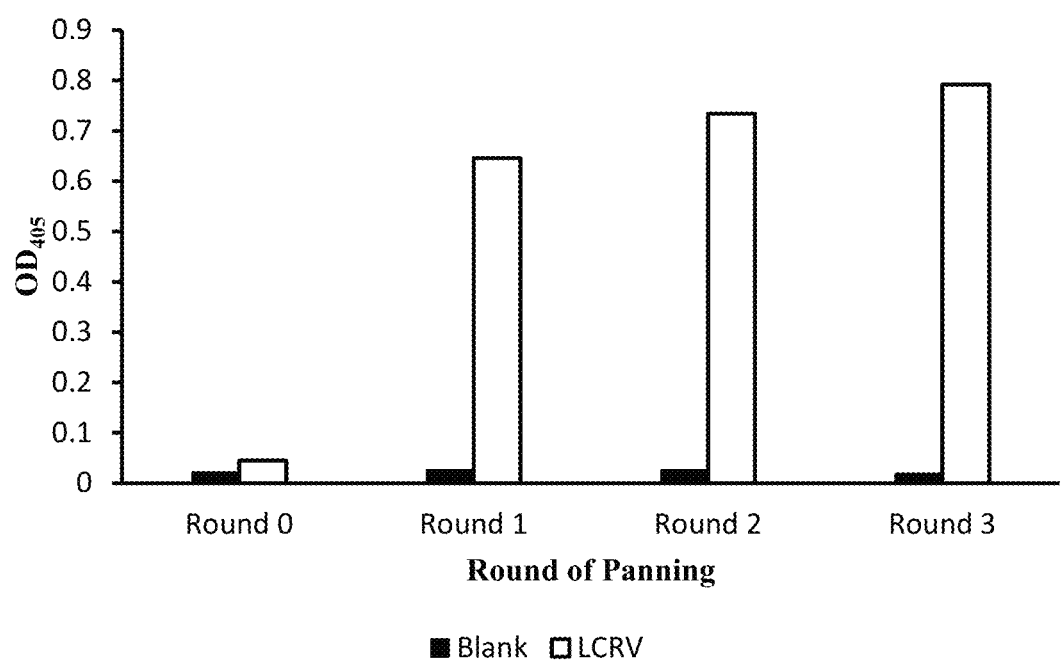
FIG. 8 is a graph of polyclonal phage ELISA testing after each round of panning to isolate LcrV-specific phages.

For the LcrV antigen, the library was subjected to three consecutive rounds of panning, performed on solid-phase coated antigen (concentration: 200 µg/ml, 20 µg/well). The enrichment for antigen-specific phages after each round of panning was assessed by comparing the number of phages eluted from antigen-coated wells with the number of phages eluted from negative control (blocked only) wells. The enrichment was also evaluated by polyclonal phage ELISA, which is shown in FIG. 8. These experiments suggested that the phage population was enriched for antigen-specific phages after the first, second, and third rounds of panning. 95 individual colonies from the second round of panning were randomly selected and analyzed by ELISA for the presence of LcrV-specific SAbs in their periplasmic extracts (not shown). Out of these 95 colonies, 85 scored positive. The VHHs from the 85 positive colonies were subjected to restriction fragment length polymorphism (RFLP) analysis using HinfI enzyme (not shown). Based on RFLP analysis, 40 colonies (several from each RFLP group) were selected for sequencing. Sequence analysis identified four different SAbs.

Figures 9A, 9B:
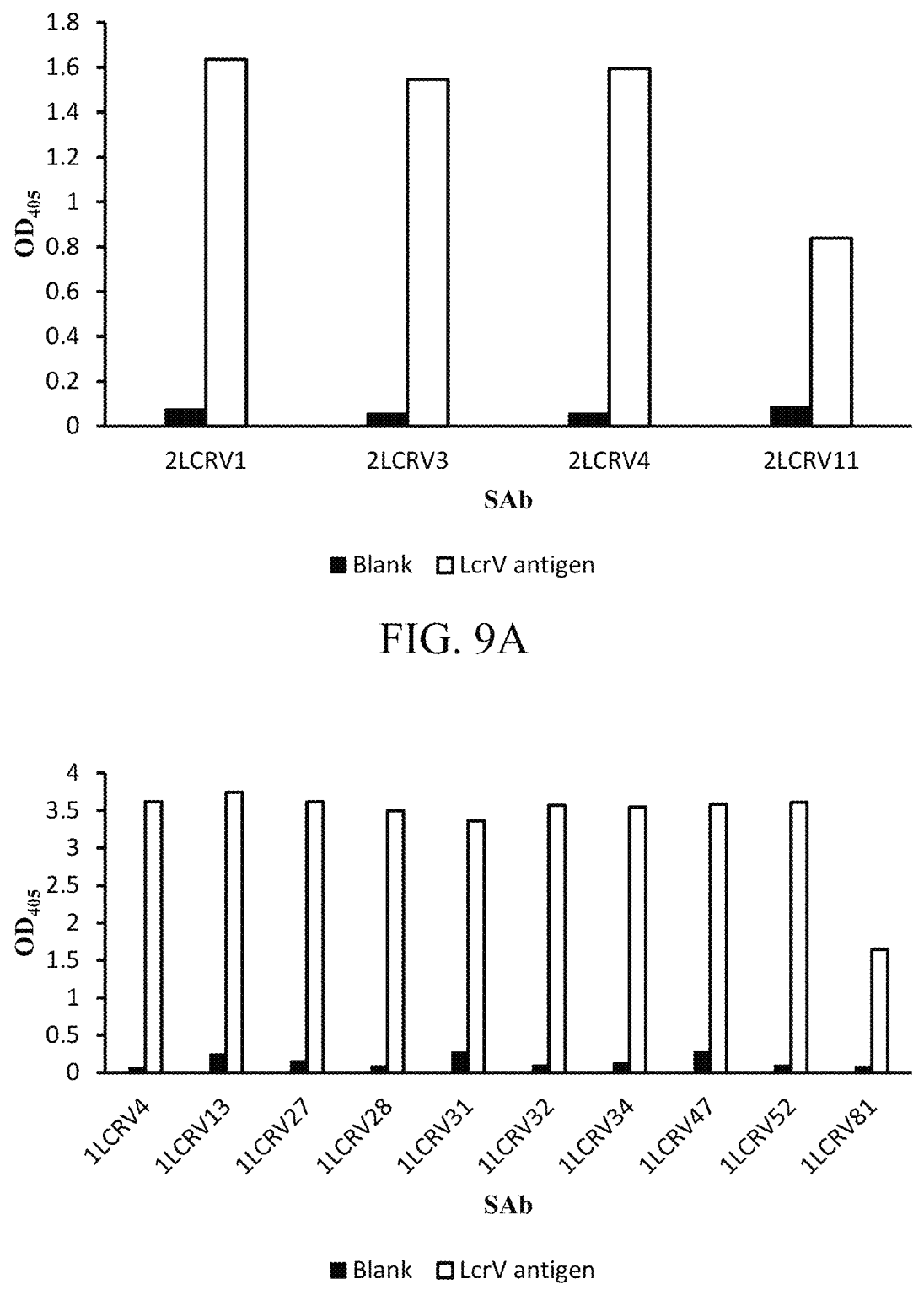

The high redundancy of the LcrV positive colonies identified after the second round of panning, together with the fact that the enrichment for antigen-specific phages was already good after the first round of panning, suggested that additional rounds of panning may have led to a loss of library diversity. To address this possibility and to identify additional unique sequences, 95 colonies from first round of panning were randomly selected and analyzed by ELISA for the presence of LcrV-specific SAbs in their periplasmic extracts, which is shown in FIGS. 9A-B. Out of these 95 colonies from the first round, 35 colonies were positive. These 35 colonies represented the four previously identified SAbs, as well as 10 novel sequences. The protein sequences of 14 exemplary LcrV SAbs according to the present invention are shown in Table 7, and the nucleic acid sequences encoding the 14 LcrV SAbs are shown in Table 8.

FIGS. 12A-B are the protein sequence alignment of the 14 exemplary LcrV SAbs listed in Table 7, and FIGS. 17A-F are sequence alignments of the nucleic acid sequences listed in Table 8. Gaps are introduced in the sequences in FIGS. 12A-B and 17A-F as needed in order to align the protein and nucleic acid sequences with one another. Referring to FIGS. 12A-B, the three CDRs are underlined in each sequence. The CDRs are defined according to the Kabat numbering system. The differences in the four FRs of each SAb (if any), as compared with 1LCRV32 (SEQ ID NO:204), are shown in bold; any differences between the three CDRs of each SAb are not otherwise indicated. The 14 exemplary LcrV SAbs shown in FIGS. 12A-B and listed in Table 7 represent six different groups, which are listed in Table 10. SAbs belonging to the same group are very similar, and their amino acid sequences suggest that they are from clonally-related B-cells resulting from somatic hypermutation or from the same B-cell with diversification due to PCR error during library construction.

Example 5

Binding Kinetics of LcrV and F1 SAbs

Binding kinetics studies were conducted on selected LcrV and F1 SAbs. LcrV and F1 protein was immobilized on the surface of a BIACORE CM5 chip (GE Healthcare Biosciences), and each SAb was allowed to associate/dissociate with the appropriate antigen. The results of the binding kinetics study are shown in Table 11. Binding generally ranged from nM to pM, with the best two SAbs (LcrV-reactive SAbs SEQ ID NOs:209, 214) binding to the target in the mid-fM range. The binding constants of the seven LcrV SAbs from Table 11 (SEQ ID NOs:204, 209, 211, 214-217) are shown in Table 12. The $K_D$ is calculated as $k_d/k_a$ ("n.b."=no binding).

Figure 13A:
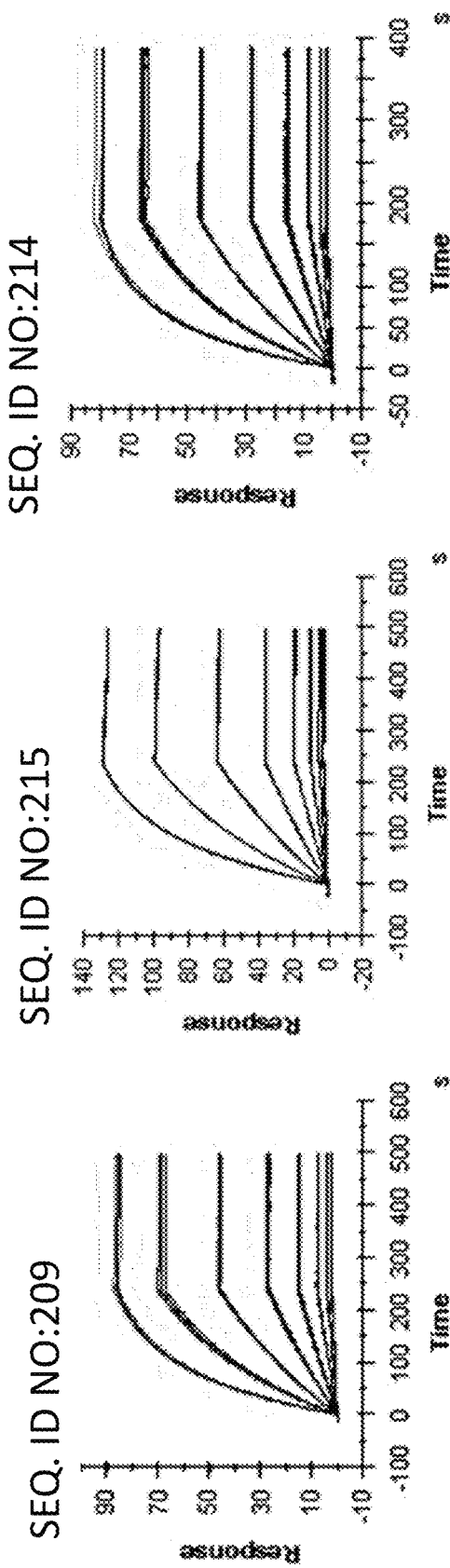
FIGS. 13A-B are the double-referenced sensorgrams obtained on the BIACORE T200 sensor instrument for selected LcrV SAbs.
Figure 13B:
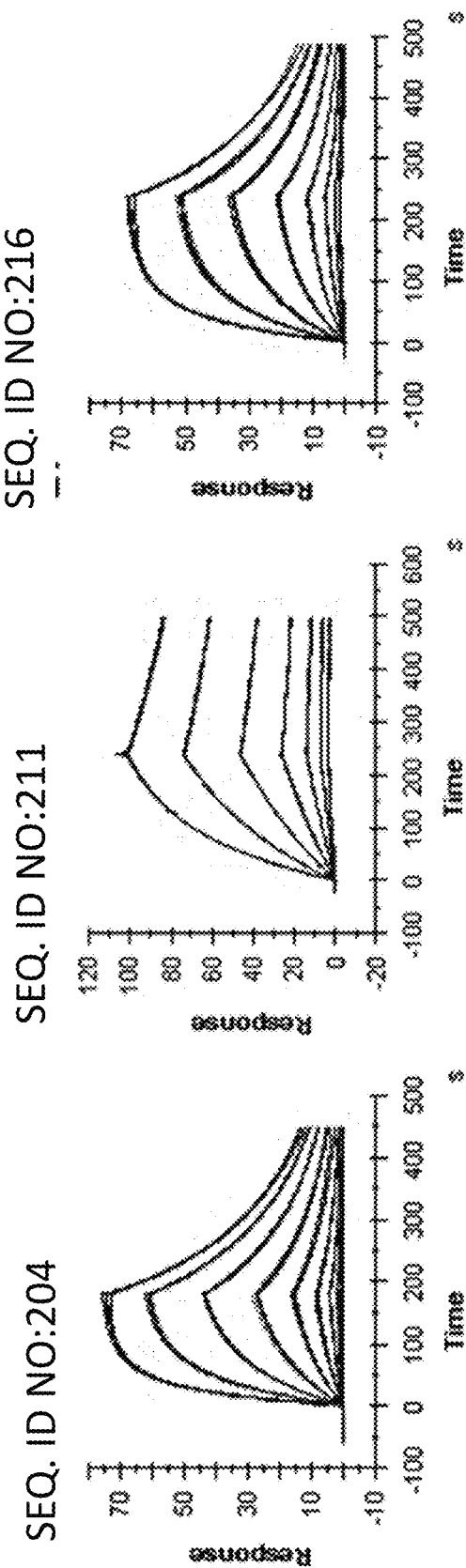

FIGS. 13A-B are the resulting double-referenced sensorgrams (colored by SAb concentration) obtained using a BIACORE T200 sensor instrument (General Electric Healthcare, United Kingdom) for six of the seven LcrV SAbs from Tables 11 and 12 (SEQ ID NOs:204, 209, 211, 214-217). A dissociation phase of 500 seconds was used for all concentrations of SAb. The overlaying curve fits are depicted in black, and the sensorgrams are based on a 1:1 binding model.

Figure 14A:
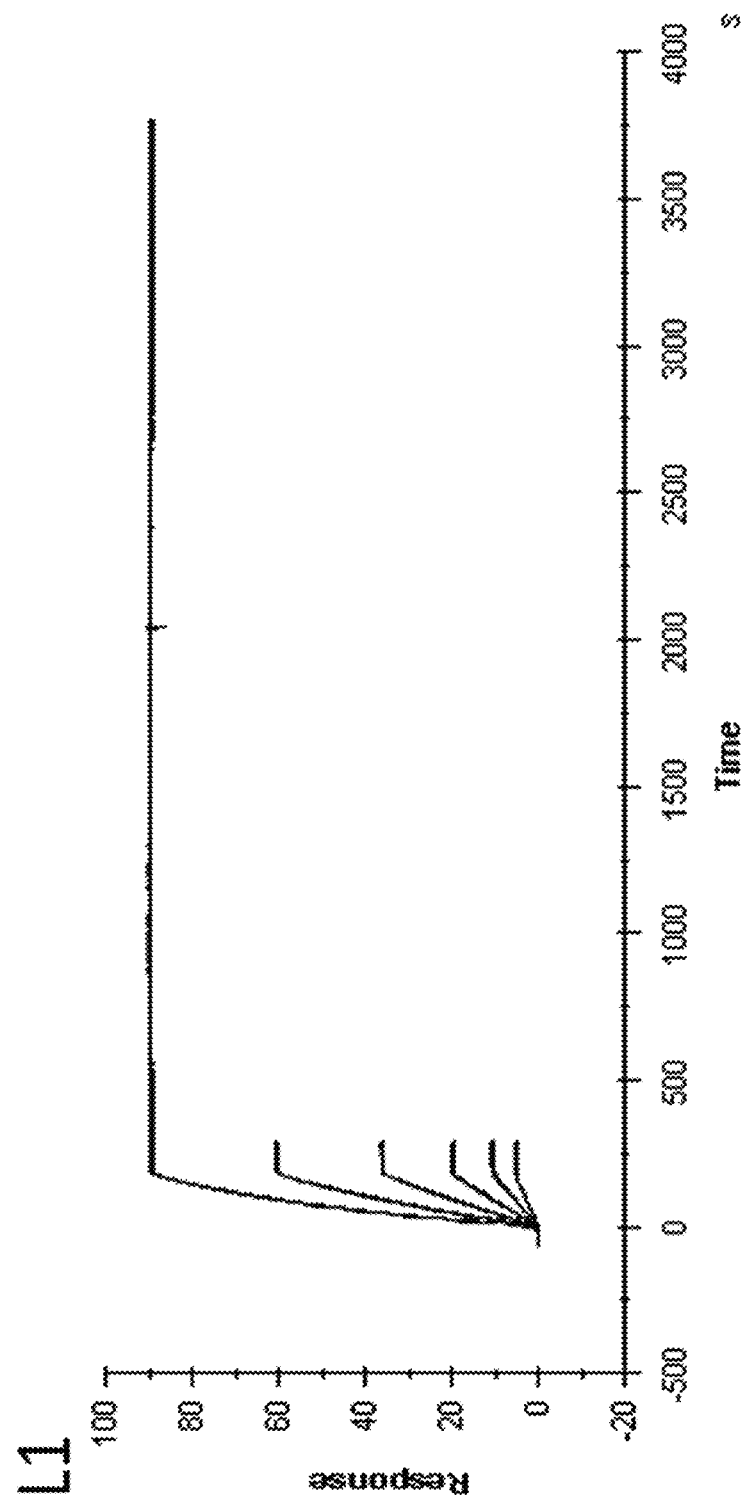
FIGS. 14A-B are the double-referenced sensorgrams obtained on the BIACORE T200 sensor instrument for the two LcrV SAbs demonstrating the best binding capabilities.
Figure 14B:
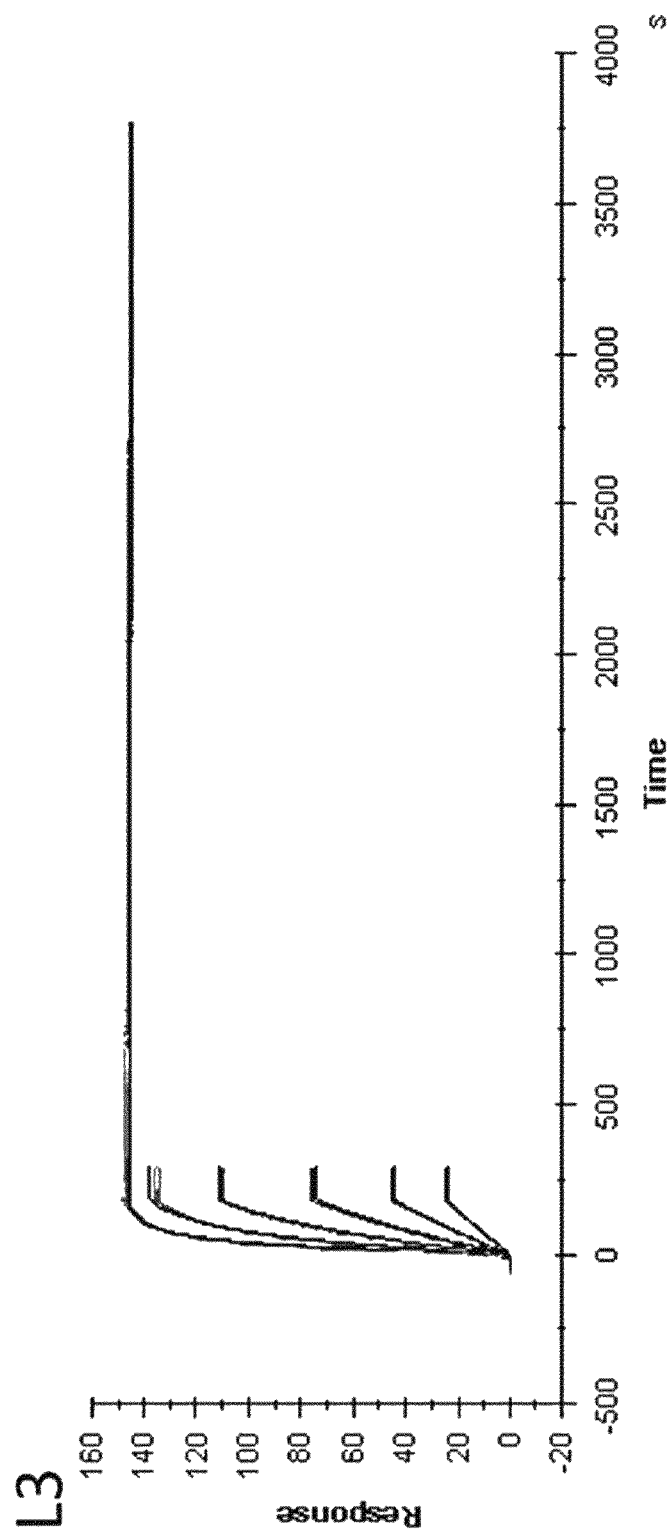

Of the described SAb sets, two SAbs (SEQ ID NOs:209, 214) demonstrate no discernible off rate ($k_d$) within the limits of THE BIACORE instrument analyses (see Tables 11 and 12). In a second test, LcrV was immobilized on the surface of a BIACORE CM5 chip, and LcrV-reactive SAbs SEQ ID NOs:209 and 214 were allowed to associate/dissociate. A dissociation phase of 120 seconds was used for all concentrations of SAb except the highest concentration, for which a 3600 second dissociation was used. FIGS. 14A-B are the double-referenced sensorgrams (colored by SAb concentration) obtained on the BIACORE T200 sensor instrument with overlaying curve fits (black), based on a 1:1 binding model. These data indicate that the SAb sequences of SEQ ID NOs:209 and 214 bind to the Y. pestis LcrV protein extremely and unusually tightly. Due to the nature of these two SAbs, both could bind to the Y. pestis bacteria in a manner that may make infection and/or replication difficult or impossible.

The present invention includes SAbs against at least one Y. pestis surface protein or antigen and the nucleotide sequences that encode the SAbs. The Y. pestis surface protein may include YscF, F1, and/or LcrV. The present invention includes a composition comprising a single SAb or a mixture of two or more different SAbs. For compositions comprising a mixture of two or more different SAbs, all of the SAbs may be against a single Y. pestis surface protein (single-antigen), or the SAbs may be against different epitopes on the same Y. pestis surface protein (single-antigen, multi-epitope). The mixture of two or more different SAbs may further comprise SAbs against two or more Y. pestis surface proteins (multi-antigen).

In one embodiment of the present invention, SAbs against at least one Y. pestis YscF epitope may comprise one each of a CDR1 sequence selected from the group consisting of SEQ ID NOs:1-7; a CDR2 sequence selected from the group consisting of SEQ ID NOs:27-33; and a CDR3 sequence selected from the group consisting of SEQ ID NOs:54-60. In another embodiment, SAbs against at least one Y. pestis YscF epitope may comprise one each of an FR1 sequence selected from the group consisting of SEQ ID NOs:79-102; a CDR1 sequence selected from the group consisting of SEQ ID NOs:1-7; an FR2 sequence selected from the group consisting of SEQ ID NOs:103-120; a CDR2 sequence selected from the group consisting of SEQ ID NOs:27-33; an FR3 sequence selected from the group consisting of SEQ ID NOs:121-146; a CDR3 sequence selected from the group consisting of SEQ ID NOs:54-60); and an FR4 sequence selected from the group consisting of SEQ ID NOs:147-153. In a further embodiment, SAbs against at least one Y. pestis YscF epitope may comprise the specific arrangement of FRs and CDRs embodied in SEQ ID NOs:154-160. The present invention further includes isolated nucleotide sequences selected from the group consisting of SEQ ID NOs:161-167 that encode the SAbs comprising SEQ ID NOs:154-160.

In another embodiment, SAbs against at least one Y. pestis F1 epitope may comprise one each of a CDR1 sequence selected from the group consisting of SEQ ID NOs:8-19; a CDR2 sequence selected from the group consisting of SEQ ID NOs:34-47; and a CDR3 sequence selected from the group consisting of SEQ ID NOs:61-71, AEY, and PGY. In another embodiment, SAbs against at least one Y. pestis F1 epitope may comprise one each of an FR1 sequence selected from the group consisting of SEQ ID NOs:79-102; a CDR1 sequence selected from the group consisting of SEQ ID NOs:8-19; an FR2 sequence selected from the group consisting of SEQ ID NOs:103-120; a CDR2 sequence selected from the group consisting of SEQ ID NOs:34-47; an FR3 sequence selected from the group consisting of SEQ ID NOs:121-146; a CDR3 sequence selected from the group consisting of SEQ ID NOs:61-71, AEY, and PGY; and an FR4 sequence selected from the group consisting of SEQ ID NOs:147-153. In a further embodiment, SAbs against at least one Y. pestis F1 epitope comprise the specific arrangement of FRs and CDRs embodied in SEQ ID NOs:168-185. The present invention further includes isolated nucleotide sequences selected from the group consisting of SEQ ID NOs:186-203 that encode the SAbs comprising SEQ ID NOs:168-185.

In a further embodiment, SAbs against at least one Y. pestis LcrV epitope may comprise one each of a CDR1 sequence selected from the group consisting of SEQ ID NOs:20-26; a CDR2 sequence selected from the group consisting of SEQ ID NOs:48-53; and a CDR3 sequence selected from the group consisting of SEQ ID NOs:72-78 and GNI. In another embodiment, SAbs against at least one Y. pestis LcrV epitope may comprise one each of an FR1 sequence selected from the group consisting of SEQ ID NOs:79-102; a CDR1 sequence selected from the group consisting of SEQ ID NOs:20-26; an FR2 sequence selected from the group consisting of SEQ ID NOs:103-120; a CDR2 sequence selected from the group consisting of SEQ ID NOs:48-53; an FR3 sequence selected from the group consisting of SEQ ID NOs:121-146; a CDR3 sequence selected from the group consisting of SEQ ID NOs:72-78 and GNI; and an FR4 sequence selected from the group consisting of SEQ ID NOs:147-153. In a further embodiment, SAbs against at least one *Y. pestis* LcrV epitope may comprise the specific arrangement of FRs and CDRs embodied in SEQ ID NOs:204-217. The present invention further includes isolated nucleotide sequences selected from the group consisting of SEQ ID NOs:218-231 that encode the SAbs comprising SEQ ID NOs:204-217.

In an alternative embodiment, the present invention includes one or more SAbs against *Y. pestis* YscF, with each SAb comprising a CDR1 sequence, a CDR2 sequence, and a CDR3 sequence respectively having at least 15% sequence identity with a CDR1 sequence selected from the group consisting of SEQ ID NOs:1-7; a CDR2 sequence selected from the group consisting of SEQ ID NOs:27-33; and a CDR3 sequence selected from the group consisting of SEQ ID NOs:54-60, in which the SAbs retain sufficient affinity for at least one of a *Y. pestis* YscF antigen or a *Y. pestis* YscF epitope. The present invention further includes one or more SAbs against *Y. pestis* YscF having at least 15% sequence identity with SEQ ID NOs:154-160, in which the SAbs retain sufficient affinity for at least one of a *Y. pestis* YscF antigen or a *Y. pestis* YscF epitope.

The present invention further includes one or more SAbs against *Y. pestis* F1, with each SAb comprising a CDR1 sequence, a CDR2 sequence, and a CDR3 sequence respectively having at least 15% sequence identity with at least one of a CDR1 sequence selected from the group consisting of SEQ ID NOs:8-19, a CDR2 sequence selected from the group consisting of SEQ ID NOs:34-47, and a CDR3 sequence selected from the group consisting of SEQ ID NOs:61-71, AEY, and PGY, in which the SAbs retain sufficient affinity for at least one of a *Y. pestis* F1 antigen or a *Y. pestis* F1 epitope. The present invention further includes one or more SAbs against *Y. pestis* F1 having at least 15% sequence identity with SEQ ID NOs:168-185, in which the SAbs retain sufficient affinity for at least one of a *Y. pestis* F1 antigen or a *Y. pestis* F1 epitope The present invention further includes one or more SAbs against *Y. pestis* LcrV, with each SAb comprising a CDR1 sequence, a CDR2 sequence, and a CDR3 sequence respectively having at least 15% sequence identity with at least one of a CDR1 sequence selected from the group consisting of SEQ ID NOs:20-26, a CDR2 sequence selected from the group consisting of SEQ ID NOs:48-53, and a CDR3 sequence selected from the group consisting of SEQ ID NOs:72-78 and GNI, in which the SAbs retain sufficient affinity for at least one of a *Y. pestis* LcrV antigen or a *Y. pestis* LcrV epitope. The present invention further includes one or more SAbs against *Y. pestis* LcrV having at least 15% sequence identity with SEQ ID NOs:204-217, in which the SAbs retain sufficient affinity for at least one of a *Y. pestis* LcrV antigen or a *Y. pestis* LcrV epitope.

In an another embodiment, the present invention further includes a polypeptide, which is used herein to refer to a structure comprising two or more of any of the above-described SAbs against *Y. pestis* YscF, F1, and/or LcrV in which the two or more SAbs are joined together. In one embodiment, the polypeptide may comprise a fusion protein that is created by joining together two or more SAbs at the genetic level. Two or more nucleic acid sequences encoding for two or more SAbs may be spliced together, and translation of the spliced nucleic acid sequence creates a longer, multi-antigen and/or multi-epitope fusion protein. The fusion protein may contain up to four SAbs joined end-to-end in a substantially linear fashion, similar to beads on a string.

In one embodiment, the fusion protein comprises SAbs that are all against a single *Y. pestis* surface protein or antigen i.e. a single-antigen fusion protein against either YscF, F1, or LcrV. In a further embodiment, this single-antigen fusion protein further comprises SAbs that bind to two or more different epitopes (multi-epitope, single-antigen) on the single antigen. In another embodiment, the fusion protein may comprise SAbs against two or more different *Y. pestis* surface proteins i.e. a multi-antigen fusion protein. The multi-antigen fusion protein may also comprise SAbs that bind to two or more different epitopes (multi-epitope, multi-antigen) on the same antigen(s). In use, each individual fusion protein molecule may bind to one *Y. pestis* surface protein molecule, or the individual fusion protein molecule may be bound to two or more separate *Y. pestis* surface protein molecules. Use of a multi-antigen and/or multi-epitope fusion protein may increase avidity in enzyme immunosorbent assays.

In another embodiment, the polypeptide may be created by joining two or more SAbs together with a protein or chemical linker to create a multivalent protein complex. For example, a linker molecule such as the verotoxin 1B-subunit may be used to create high avidity, pentavalent SAb complexes similar to keys on a key ring. In one embodiment, the multivalent protein complex may contain SAbs that are all against a single *Y. pestis* surface protein or antigen i.e. a single-antigen multivalent protein complex. This single-antigen multivalent protein complex may further comprise SAbs that bind to two or more different epitopes (multi-epitope, single-antigen) on the single antigen. In another embodiment, the multivalent protein complex may comprise SAbs against two or more different *Y. pestis* surface proteins i.e. a multi-antigen multivalent protein complex. The multi-antigen multivalent protein complex may further comprise SAbs that bind to two or more different epitopes (multi-epitope, multi-antigen) on the same antigen. In use, each multivalent protein complex may bind to one *Y. pestis* surface protein molecule, or the multivalent protein complex may be bound to two or more separate *Y. pestis* surface protein molecules. These multi-antigen and/or multi-epitope multivalent protein complexes may generally demonstrate increased affinity for their respective epitope and/or antigen target(s) and may have numerous applications for biomarker assays or proteomics.

In one embodiment of the present invention, polypeptides as described herein comprise at least two SAbs, with the SAbs being selected from the following groups: (1) SAbs comprising one each of a CDR1 sequence selected from the group consisting of SEQ ID NOs:1-7; a CDR2 sequence selected from the group consisting of SEQ ID NOs:27-33; and a CDR3 sequence selected from the group consisting of SEQ ID NOs:54-60; (2) SAbs comprising one each of a CDR1 sequence selected from the group consisting of SEQ ID NOs:8-19; a CDR2 sequence selected from the group consisting of SEQ ID NOs:34-47; and a CDR3 sequence selected from the group consisting of SEQ ID NOs:61-71, AEY, and PGY; and (3) SAbs comprising one each of a CDR1 sequence selected from the group consisting of SEQ ID NOs:20-26; a CDR2 sequence selected from the group consisting of SEQ ID NOs:48-53; and a CDR3 sequence selected from the group consisting of SEQ ID NOs:72-78 and GNI.

In a further embodiment, the polypeptides comprise at least two SAbs selected from the group consisting of: (1) SAbs comprising one each of a CDR1 sequence selected from the group consisting of sequences having at least 15% sequence identity with SEQ ID NOs:1-7; a CDR2 sequence selected from the group consisting of sequences having at least 15% sequence identity with SEQ ID NOs:27-33; and a CDR3 sequence selected from the group consisting of sequences having at least 15% sequence identity with SEQ ID NOs:54-60; (2) SAbs comprising one each of a CDR1 sequence selected from the group consisting of sequences having at least 15% sequence identity with SEQ ID NOs: 8-19; a CDR2 sequence selected from the group consisting of sequences having at least 15% sequence identity with SEQ ID NOs:34-47; and a CDR3 sequence selected from the group consisting of sequences having at least 15% sequence identity with SEQ ID NOs:61-71; and (3) SAbs comprising one each of a CDR1 sequence selected from the group consisting of sequences having at least 15% sequence identity with SEQ ID NOs:20-26; a CDR2 sequence selected from the group consisting of sequences having at least 15% sequence identity with SEQ ID NOs:48-53; and a CDR3 sequence selected from the group consisting of sequences having at least 15% sequence identity with SEQ ID NOs: 72-78.

In another embodiment, the polypeptides may comprise at least two SAbs, with the SAbs being selected from the following groups: (1) SAbs comprising one set of CDR1, CDR2, and CDR3 sequences (as described above with respect to polypeptides according to the present invention) and one each of an FR1 sequence selected from the group consisting of SEQ ID NOs:79-102, an FR2 sequence selected from the group consisting of SEQ ID NOs:103-120, an FR3 sequence selected from the group consisting of SEQ ID NOs:121-146, and an FR4 sequence selected from the group consisting of SEQ ID NOs:147-153; and (2) SAbs selected from the group consisting of SEQ ID NOs:154-160, 168-185, and 204-217 and sequences having at least 15% sequence identity with SEQ ID NOs:154-160, 168-185, and 204-217.

In another embodiment, any of the SAbs or polypeptides according to the present invention may further comprise a protein tag, a protein domain tag, or a chemical tag. These tags generally comprise one or more additional amino acids or chemical molecules or residues that may be placed using known methods on the C- or N-terminus of the SAb or polypeptide without altering the activity or functionality of the SAb or polypeptide. The tag may facilitate purification of the SAb or polypeptide, direct absorption and/or excretion in the body, and/or facilitate use in a variety of applications such as detecting and monitoring Y. pestis. The tag may include, but is not limited to, a histidine tag (HIS tag) and a poly-lysine tag.

The present invention further includes a method of preventing or treating a Y. pestis infection in a patient. Y. pestis infections are frequently difficult to properly diagnose, which can result in delayed treatment, and a low toxicity treatment such as the presently disclosed SAbs may provide a valuable tool for cases of suspected Y. pestis exposure and/or infection and/or for patients presenting with ambiguous symptoms. The method comprises identifying a patient who is suspected of having been exposed to and/or infected with Y. pestis, and administering to the patient a pharmaceutically active amount of one or more of the SAbs and/or polypeptides according to the present invention. As used throughout, a "pharmaceutically active amount" refers generally to an amount that upon administration to the patient, is capable of providing directly or indirectly, one or more of the effects or activities disclosed herein. In one embodiment, the SAb(s) and/or polypeptide(s) may be administered as a form of passive immunotherapy in which the SAb(s) and/or polypeptide(s) are administered to the patient prior to at least one of exposure to or infection with Y. pestis. In another embodiment, the SAb(s) and/or polypeptide(s) may be administered after the patient is exposed to or infected with Y. pestis. The SAb(s) and/or polypeptide(s). In all embodiments of the methods, the SAb(s) and/or polypeptide(s) may be capable of being self-administered and may be administered to the patient using known techniques including, but not limited to, intravenous and subcutaneous injection, oral ingestion, inhalation, and topical administration. The ability to self-administer the SAb(s) and/or polypeptide(s) may be particularly useful in the case of an outbreak or attack where access to medical personnel and treatment may be limited.

The present invention further includes a method of detecting and/or diagnosing a Y. pestis infection using one of more of the SAbs and/or polypeptides herein described. The method may include detection of Y. pestis and diagnosis of the infection using known in vivo and/or in vitro assays such as enzyme linked immunosorbent assays (ELISAs), dot blot assays, and other suitable immunoassays. The Y. pestis SAb(s) and/or polypeptide(s) may, for example, be used as a primary antibody or a capture antibody in an ELISA for the detection/diagnosis of a Y. pestis infection. The SAb(s) and/or polypeptide(s) according to the present invention may further be coupled to one or more enzymes or markers for use in imaging.

The present invention further includes devices and methods for the identification and detection of Y. pestis on a surface and/or in an environment. A device for the environmental detection and/or quantification of Y. pestis may comprise one or more of the SAbs or polypeptides according to the present invention, with the SAb(s) and/or polypeptide(s) being used as a capture element. A method of identifying and detecting Y. pestis using the device comprises contacting one or more of the SAbs or polypeptides with an unknown target and detecting binding between the SAbs or polypeptides and the unknown target to identify the unknown target as Y. pestis. The method may further comprise use of the device to quantify an amount of Y. pestis on the surface and/or in the environment.

TABLE 1

Amino Acid Code

| Alanine | Ala | A | Methionine | Met | M |
| Cysteine | Cys | C | Asparagine | Asn | N |
| Aspartic Acid | Asp | D | Proline | Pro | P |
| Glutamic Acid | Glu | E | Glutamine | Gln | Q |
| Phenylalanine | Phe | F | Arginine | Arg | R |
| Glycine | Gly | G | Serine | Ser | S |
| Histidine | His | H | Threonine | Thr | T |
| Isoleucine | Ile | I | Valine | Val | V |
| Lysine | Lys | K | Tryptophan | Trp | W |
| Leucine | Leu | L | Tyrosine | Tyr | Y |

TABLE 2

Exemplary Combinations of FR and CDR Sequences

| ID # FR1 | ID # CDR1 | ID # FR2 | ID # CDR2 | ID # FR3 | ID # CDR3 | ID # FR4 |
|---|---|---|---|---|---|---|
| YscF SAb Sequences | | | | | | |
| 79 QVQLQESGGGLVQAGGSLRLSCAAS | 1 GRTWRAYYMG | 103 WFRQAPGKEREFVA | 27 VMSRSGGTTSYADSVKG | 121 RFTISRDNAKNTVYLQMNNLAPEDTATYYCKA | 54 GGGMYGPDLYGMTY | 147 WGKGTQVTVSS |
| 80 QVQLQESGGGLVQAGGSLRLSCVAS | 2 GRAFSNYAMA | 103 WFRQAPGKEREFVA | 28 ANWRSGGLTDYADSVKG | 122 RFTISRDDAKNTVYLQMNSLKPEDTAVYYCAA | 55 GGGSRWYGRTTASWYDY | 148 WGQGTQVTVSS |
| 81 QVQLQESGGGLVQAGGSLRLSCAVS | 3 GRTFSRYAMG | 103 WFRQAPGKEREFVA | 29 AISWSGSSTYYADSVKG | 123 RFTISRDHAKNVMYLQMNGLKPEDTGVYVCAR | 56 PAYGLRPPYNY | 149 RGQGTQVTVSS |
| 82 QVQLQESGGGLVQAGGSLKLSCTAS | 4 QRTFSRYSLG | 104 WFRQAPGEERVFVA | 30 ATTWSGISSDYADSVKG | 124 RFTISRDNAKNTGYLQMNNLKPEDTGVYYCAA | 57 GRSSWFAPWLTPYEYDY | 150 WGRGTQVTVSS |
| 79 QVQLQESGGGLVQAGGSLRLSCAAS | 5 GRTFSSHAMA | 105 WFRQGPGEERQFLA | 31 AIRWNGDNIHYSDSAKG | 125 RFTISRDLAKNTLYLQMNSLKPEDTAVYYCAR | 58 GVYDY | 148 WGQGTQVTVSS |
| 83 QVQLQESGGGLVQAGDSRILSCTAS | 6 GRTFGRPFRYTMG | 106 WFRRAPGKEREFVG | 32 GITRSGNNIYYSDSVKG | 126 RFTISRDNAKNTVYLQMNSLKPEDTAVYYCNA | 59 DWGWRNY | 148 WGQGTQVTVSS |
| 84 QVQLQESGGGLVQAGGSLRLACAAS | 7 GETVDDLAIG | 107 WFRQAPGKEREEIS | 33 CISGSDGSTYYADSLSG | 127 RFTISRDNVKNTVYLQMNSLKLEDTAVYYCYA | 60 EIYDRRWYRNDY | 148 WGQGTQVTVSS |
| F1 SAb Sequences | | | | | | |
| 81 QVQLQESGGGLVQAGGSLRLSCAVS | 8 GMMYIREAIR | 108 WYRQAPGKQREWVA | 34 FVSSTGNPRYTDSVKG | 128 RFTISRDNAKNTVYLQMNSLTPEDTAVYYCNT | 61 YLGSRDY | 148 WGQGTQVTVSS |
| 85 QVQLQESGGGLVQPGGSLRLSCAVS | 9 GMMYIRYTMR | 108 WYRQAPGKQREWVA | 35 VVSSTGNPHYADSVKG | 128 RFTISRDNAKNTVYLQMNSLTPEDTAVYYCNT | 61 YLGSRDY | 148 WGQGTQVTVSS |
| 86 QVQLQESGGGLVRPGGSLRLSCAVS | 10 GRAVNRYHMH | 109 WYRQAPGKQREWVT | 36 FISVGGTTNYAGSVKG | 129 RFTVSRDNAKNTLYLQMNSLKPEDTAVYYCNS | * AEY | 148 WGQGTQVTVSS |
| 87 QVQLQESGGGSVQPGGSLSLSCSAS | 11 GIIFSDYALT | 108 WYRQAPGKQREWVA | 37 QITRSQNINYTGSVKG | 130 RFTVSRDNAKNTVHLQMNSLKPEDTAVYYCHA | 62 YDGRRPPY | 148 WGQGTQVTVSS |
| 87 QVQLQESGGGSVQPGGSLSLSCSAS | 11 GIIFSDYALTVV | 108 WYRQAPGKQREWVA | 37 QITRSQNINYTGSVPEDTAVYYCHKG | 130 RFTVSRDNAKNTVHLQMNSLKA | 63 YDGRRRTY | 148 WGQGTQVTVSS |
| 88 QVQLQESGGGLVQPGGSLSLSCSAS | 11 GIIFSDYALT | 108 WYRQAPGKQREWVA | 37 QITRSQNINYTGSVKG | 130 RFTVSRDNAKNTVHLQMNSLKPEDTAVYYCHA | 62 YDGRRPPY | 148 WGQGTQVTVSS |
| 88 QVQLQESGGGLVQPGGSLSLSCSAS | 11 GIIFSDYALT | 108 WYRQAPGKQREWVA | 38 QITRRQNINYTGSVKG | 130 RFTVSRDNAKNTVHLQMNSLKPEDTAVYYCHA | 64 YDGRRSPY | 148 WGQGTQVTVSS |
| 89 QVQLQESGGGLVQPGGSLRLSCSAS | 11 GIIFSDYALT | 108 WYRQAPGKQREWVA | 37 QITRSQNINYTGSVKG | 131 RFTVSRDNAKNTVHLQMNSLKPEDAAVYYCHA | 62 YDGRRPPY | 148 WGQGTQVTVSS |

TABLE 2-continued

Exemplary Combinations of FR and CDR Sequences

| ID # FR1 | ID # CDR1 | ID # FR2 | ID # CDR2 | ID # FR3 | ID # CDR3 | ID # FR4 |
|---|---|---|---|---|---|---|
| 90 QVQLQESGG GLVQPGGSL RLSCAAS | 12 ARIFSI YAMV | 108 WYRQA PGKQR EWVA | 39 AITTGGT TNYADS VKG | 126 RFTISRDNAKN TVYLQMNSLKP EDTAVYYCNA | * PGY | 148 WGQGTQ VTVSS |
| 90 QVQLQESGG GLVQPGGSL RLSCAAS | 13 GVIASI SVLR | 110 WYRQT PGKTR DWVA | 40 IITSGGN TRYADS VKG | 132 RFTTSRDNARN TVYLQMNSLKP EDTAVYYCNT | 65 LVGAKD Y | 148 WGQGTQ VTVSS |
| 91 QVQLQESGG GLVRPGGSL RLSCEAS | 14 GTTFRS LVMK | 111 WYRQA PGKER EWVA | 41 FISSPGD RTRYTE AVKG | 133 RFTISRDNAKN ALYLQMNGLK PEDTAVYYCN A | 66 NGIY | 147 WGKGTQ VTVSS |
| 92 QVQLQESGG GLVQSGDSL RLSCAAS | 15 GFTFSN YAMS | 112 WVRQA PGKGL EWVS | 42 TINSGG GSTSYA YSVKG | 134 RFTISRDNAKN TLYLQMNSLKP EDTAVYYCAK | 67 TASHIP | 151 LSQGTQ VTVSS |
| 90 QVQLQESGG GLVQPGGSL RLSCAAS | 15 GFTFSN YAMS | 112 WVRQA PGKGL EWVS | 43 TINIGGG STSYAD SVKG | 134 RFTISRDNAKN TLYLQMNSLKP EDTAVYYCAK | 67 TASHIP | 151 LSQGTQ VTVSS |
| 90 QVQLQESGG GLVQPGGSL RLSCAAS | 16 GFTFRN YAMS | 112 WVRQA PGKGL EWVS | 44 TINGGG GITSYAD SVKG | 135 RFTISRDNAKN TMYLQMNSLK PEDTAVYYCA Q | 68 TARDSR DS | 149 RGQGTQ VTVSS |
| 90 QVQLQESGG GLVQPGGSL RLSCAAS | 17 GFTFSS YAMS | 113 WVRLA PGKGL EWVS | 45 TINIAGG ITSYADS VKG | 134 RFTISRDNAKN TLYLQMNSLKP EDTAVYYCAK | 69 TAANWS AQ | 149 RGQGTQ VTVSS |
| 90 QVQLQESGG GLVQPGGSL RLSCAAS | 17 GFTFSS YAMS | 112 WVRQA PGKGL EWVS | 46 TINMGG GTTSYA DSVKG | 136 RFTISRHNAKN TLYLQMNSLKP EDTAVYYCAK | 70 TAGNWS AQ | 149 RGQGTQ VTVSS |
| 90 QVQLQESGG GLVQPGGSL RLSCAAS | 18 GFTFST SAMS | 114 WIRQPP GKARE VVA | 47 TITSAGG SISYVNS VKG | 137 RFTISRDNAKN TLYLQMNMLK PEDTAVYYCAR | 71 LVNLAQ | 152 TGQGTQ VTVSS |
| 90 QVQLQESGG GLVQPGGSL RLSCAAS | 19 GFTFST NAMS | 114 WIRQPP GKARE VVA | 47 TITSAGG SISYVNS VKG | 137 RFTISRDNAKN TLYLQMNMLK PEDTAVYYCAR | 71 LVNLAQ | 152 TGQGTQ VTVSS |
| LcrV SAb Sequences | | | | | | |
| 93 QVQLQESGG GMVEPGGSL RLSCAAS | 20 GFRFSS YAMS | 115 WVRQA PGKGL ERVS | 48 AINSDG DKTSYA DSVKG | 138 RFTISRDNARN TLYLQMSNLKP EDTAVYYCAD | 72 RDLYCS GSMCKD VLGGAR YDF | 149 RGQGTQ VTVSS |
| 94 QVQLQESGG GLVEPGGSL RLSCAAS | 20 GFRFSS YAMS | 115 WVRQA PGKGL ERVS | 48 AINSDG DKTSYA DSVKG | 138 RFTISRDNARN TLYLQMSNLKP EDTAVYYCAD | 72 RDLYCS GSMCKD VLGGAR YDF | 149 RGQGTQ VTVSS |
| 93 QVQLQESGG GMVEPGGSL RLSCAAS | 20 GFRFSS YAMS | 115 WVRQA PGKGL ERVS | 48 AINSDG DKTSYA DSVKG | 139 RFTISRDNARN TLYLQMNNLK PEDTAVYYCA D | 72 RDLYCS GSMCKD VLGGAR YDF | 149 RGQGTQ VTVSS |
| 95 QVQLQESGG GLVQSGESL RLSCAAS | 21 GLRFSS YAMS | 115 WVRQA PGKGL ERVS | 48 AINSDG DKTSYA DSVKG | 138 RFTISRDNARN TLYLQMSNLKP EDTAVYYCAD | 72 RDLYCS GSMCKD VLGGAR YDF | 149 RGQGTQ VTVSS |
| 96 QVQLQESGG GLVQPGGSL KLSCAAS | 22 GFTFN WYTM A | 116 WYRQV PGEER KMVA | 49 TITGASG DTKYAD SVKG | 140 RFTISRDNAKN TVTLQMNSLKP GDAAVYYCHA | 73 YLTYDS GSVKGV NY | 148 WGQGTQ VTVSS |
| 97 QVQLQESGG GLVRPGGSL KLSCAAS | 22 GFTFN WYTM A | 116 WYRQV PGEER KMVA | 49 TITGASG DTKYAD SVKG | 141 RFTISRDNAKN TVTLQMNSLKP GDTAVYYCHA | 73 YLTYDS GSVKGV NY | 148 WGQGTQ VTVSS |
| 98 QVQLQESGG GSVQPGGSL KLSCAAS | 22 GFTFN WYTM A | 116 WYRQV PGEER KMVA | 49 TITGASG DTKYAD SVKG | 141 RFTISRDNAKN TVTLQMNSLKP GDTAVYYCHA | 73 YLTYDS GSVKGV NY | 148 WGQGTQ VTVSS |

TABLE 2-continued

Exemplary Combinations of FR and CDR Sequences

| ID # FR1 | ID # CDR1 | ID # FR2 | ID # CDR2 | ID # FR3 | ID # CDR3 | ID # FR4 |
|---|---|---|---|---|---|---|
| 98 QVQLQESGG GSVQPGGSL KLSCAAS | 22 GFTFN WYTM A | 116 WYRQV PGEER KMVA | 49 TITGASG DTKYAD SVKG | 142 RSTISRDNAKN TVTLQMNSLKP GDTAVYYCHA | 74 CLTYDS GSVKGV NY | 148 WGQGTQ VTVSS |
| 99 QVQLQESGG GFVQPGGSL KLSCAAS | 22 GFTFN WYTM A | 116 WYRQV PGEER KMVA | 49 TITGASG DTKYAD SVKG | 141 RFTISRDNAKN TVTLQMNSLKP GDTAVYYCHA | 73 YLTYDS GSVKGV NY | 148 WGQGTQ VTVSS |
| 96 QVQLQESGG GLVQPGGSL KLSCAAS | 22 GFTFN WYTM A | 116 WYRQV PGEER KMVA | 49 TITGASG DTKYAD SVKG | 141 RFTISRDNAKN TVTLQMNSLKP GDTAVYYCHA | 75 YLTYDS GSAKGV NY | 148 WGQGTQ VTVSS |
| 100 QVQLQESGG GLVQPGGSL GLSCAAS | 23 GSLLNI YAMG | 117 WYRQA PGRQR ELVA | 50 TVTSSG TAEYAD SVKG | 143 RFTISRDNAKN TVYLQMNSLRP EDTGVYYCNA | 76 HLRYGD YVRGPP EYNY | 148 WGQGTQ VTVSS |
| 90 QVQLQESGG GLVQPGGSL RLSCAAS | 24 GGTLG YYAIG | 118 WFRQA PGKER EAVS | 51 CITSSDT SAYYAD SAKG | 144 RFTISRDNAKN TMYLQMNNLK PEDTAVYYCA A | 77 GYYFRD YSDSYY YTGTGM KV | 147 WGKGTQ VTVSS |
| 101 QVQLQESGG GLVQPGGST RLSCAAS | 25 GFTLDI YAIG | 119 WFRQA PGKEH EGVS | 52 WIVGND GRTYYI DSVKG | 145 RFTISRDNAKN TVYLEMNSLKP EDTAVYYCAA | 78 KFWPRY YSGRPP VGRDGY DY | 148 WGQGTQ VTVSS |
| 102 QVQLQESGG GLVQPGGSL ILSCTIS | 26 GASLR DRRVT | 120 WSRQG PGKSLE IIA | 53 VMAPDY GVHYFG SLEG | 146 RVAVRGDVVK NTVYLQVNAL KPEDTAIYWCS M | * GNI | 153 RGLGTQ VTVSS |

* These sequences have fewer than the required minimum of four amino acids and are not assigned a SEQ. NO.

TABLE 3

Y. pestis YscF SAb Protein Sequences

| SEQ ID NO | Name | Sequence |
|---|---|---|
| 154 | 3yscf57 | QVQLQESGGGLVQAGGSLRLSCAASGRTWRAYYMGWFRQAPGKEREFVAVMSRSGGTTSYADSVK GRFTISRDNAKNTVYLQMNNLAPEDTATYYCKAGGGMYGPDLYGMTYWGKGTQVTVSS |
| 155 | 3yscf124 | QVQLQESGGGLVQAGGSLRLSCVASGRAFSNYAMAWFRQAPGKEREFVAANWRSGGLTDYADSVK GRFTISRDDAKNTVYLQMNSLKPEDTAVYYCAAGGGSRWYGRTTASWYDYWGQGTQVTVSS |
| 156 | 3yscf15 | QVQLQESGGGLVQAGGSLRLSCAVSGRTFSRYAMGWFRQAPGKEREFVAAISWSGSSTYYADSVKG RFTISRDHAKNVMYLQMNGLKPEDTGVYVCARPAYGLRPPYNYRGQGTQVTVSS |
| 157 | 3yscf24 | QVQLQESGGGLVQAGGSLKLSCTASQRTFSRYSLGWFRQAPGEERVFVAATTWSGISSDYADSVKG RFTISRDNAKNTGYLQMNNLKPEDTGVYYCAAGRSSWFAPWLTPYEYDYWGRGTQVTVSS |
| 158 | 3yscf142 | QVQLQESGGGLVQAGGSLRLSCAASGRTFSSHAMAWFRQGPGEERQFLAAIRWNGDNIHYSDSAKG RFTISRDLAKNTLYLQMNSLKPEDTAVYYCARGVYDYWGQGTQVTVSS |
| 159 | 3yscf75 | QVQLQESGGGLVQAGDSRILSCTASGRTFGRPFRYTMGWFRRAPGKEREFVGGITRSGNNIYYSDSV KGRFTISRDNAKNTVYLQMNSLKPEDTAVYYCNADWGWRNYWGQGTQVTVSS |
| 160 | 3yscf140 | QVQLQESGGGLVQAGGSLRLACAASGETVDDLAIGWFRQAPGKEREEISCISGSDGSTYYADSLSGRF TISRDNVKNTVYLQMNSLKLEDTAVYYCYAEIYDRRWYRNDYWGQGTQVTVSS |

TABLE 4

Y. pestis YscF SAb DNA Sequences

| SEQ ID NO | Name | Sequence |
|---|---|---|
| 161 | 3yscf57 | CAGGTGCAGCTGCAGGAGTCTGGGGGAGGATTGGTGCAGGCTGGGGGCTCTCTGAGACTCTCCT GTGCAGCCTCTGGACGCACCTGGAGAGCCTATTACATGGGCTGGTTCCGCCAGGCTCCAGGGAA GGAGCGTGAGTTTGTAGCAGTTATGAGTCGGAGCGGTGGCACCACATCCTATGCGGACTCCGTG AAGGGCCGATTCACCATCTCCAGAGACAACGCCAAGAACACGGTGTATCTACAAATGAACAACC |

TABLE 4-continued

Y. pestis YscF SAb DNA Sequences

| SEQ ID NO | Name | Sequence |
|---|---|---|
|  |  | TGGCACCTGAGGACACGGCCACGTATTATTGTAAGGCGGGGGGCGGAATGTACGGGCCGGACCT<br>GTATGGTATGACATACTGGGGCAAAGGGACCCAGGTCACCGTCTCCAGCGGCCGCTACCCGTAC<br>GACGTTCCGGACTACGGTTCCGGCCGAGCATAG |
| 162 | 3yscf124 | CAGGTGCAGCTGCAGGAGTCTGGAGGAGGATTGGTACAGGCTGGGGGCTCTCTGAGACTCTCCT<br>GTGTAGCCTCTGGACGCGCCTTCAGTAATTATGCGATGGCCTGGTTCCGCCAGGCTCCAGGGAAG<br>GAGCGTGAGTTTGTAGCAGCTAATTGGCGGAGTGGTGGTCTTACAGACTATGCAGACTCCGTGA<br>AGGGCCGATTCACCATCTCCAGAGACGACGCCAAGAACGTGTATCTGCAAATGAACAGCCT<br>GAAACCTGAGGACACGGCCGTTTATTACTGTGCCGCCGGGGGCGGTAGTCGCTGGTACGGGCGA<br>ACAACCGCAAGTTGGTATGACTACTGGGGCAGGGGACCCAGGTCACCGTCTCCAGCGGCCGCT<br>ACCCGTACGACGTTCCGGACTACGGTTCCGGCCGAGCATAG |
| 163 | 3yscf15 | CAGGTGCAGCTGCAGGAGTCTGGGGGAGGATTGGTGCAGGCTGGGGGCTCTCTGAGACTCTCCT<br>GTGCAGTCTCTGGACGCACCTTCAGTAGATATGCCATGGGCTGGTTCCGCCAGGCTCCAGGGAAG<br>GAGCGTGAGTTTGTAGCAGCTATTAGCTGGAGTGGTAGTAGCACATATTATGCAGACTCCGTGAA<br>GGGCCGATTCACCATCTCCAGAGACCACGCCAAGAACGTGATGTATCTGCAAATGAACGGCCTG<br>AAACCTGAGGACACGGGTGTTTATGTCTGTGCAAGACCAGCGTACGGACTCCGCCCCCGTATA<br>ATTACCGGGGCCAGGGGACCCAGGTCACCGTCTCCAGCGGCCGCTACCCGTACGACGTTCCGGA<br>CTACGGTTCCGGCCGAGCATAG |
| 164 | 3yscf24 | CAGGTGCAGCTGCAGGAGTCTGGGGGAGGATTGGTGCAGGCTGGGGGCTCTCTGAAACTCTCCT<br>GCACAGCCTCTCAACGCACCTTCAGTCGCTATAGCTTGGGCTGGTTCCGCCAGGCTCCAGGTGAG<br>GAGCGTGTTTTTGTAGCCGCTACTACATGGAGTGGTATAAGCAGTGACTATGCAGACTCCGTGAA<br>GGGCCGATTCACCATCTCCAGAGACAACGCCAAGAACACGGGGTATCTGCAAATGAACAATTTA<br>AAACCTGAGGACACGGGCGTTTATTACTGTGCAGCAGGACGTAGTAGCTGGTTCGCCCCCTGGTT<br>GACCCCCTATGAGTATGATTATTGGGGCCGGGGGACCCAGGTCACCGTCTCCAGCGGCCGCTACC<br>CGTACGACGTTCCGGACTACGGTTCCGGCCGAGCATAG |
| 165 | 3yscf142 | CAGGTGCAGCTGCAGGAGTCTGGGGGAGGATTGGTGCAGGCTGGGGGCTCTCTGAGACTCTCCT<br>GTGCAGCCTCTGGACGCACCTTCAGTAGCCATGCCATGGGCTGGTTCCGCCAGGGTCCAGGAGA<br>GGAGCGTCAGTTTCTAGCAGCTATTAGATGGAATGGTGATAACATACACTATTCGACTCCGCGA<br>AGGGCCGATTCACCATCTCCAGAGACCTCGCCAAGAACACGCTCTATCTGCAAATGAACAGCCT<br>GAAACCTGAGGACACGGCCGTGTATTACTGTGCAAGGGGGGTGTATGACTACTGGGGCCAGGGG<br>ACCCAGGTCACCGTCTCCAGCGGCCGCTACCCGTACGACGTTCCGGACTACGGTTCCGGCCGAGC<br>ATAG |
| 166 | 3yscf75 | CAGGTGCAGCTGCAGGAGTCTGGGGGAGGATTGGTGCAGGCTGGGGACTCTCGGATACTCTCCT<br>GTACAGCCTCTGGACGCACCTTTGGACGCCCCTTCAGATATACCATGGGCTGGTTCCGCCGGGCT<br>CCAGGGAAGGAGCGTGAGTTTGTAGGAGGTATTACAAGAAGTGTAATAATATATACTATTCAG<br>ACTCCGTGAAGGGCCGATTCACCATCTCCAGAGACAACGCCAAGAACACGGTGTATCTCCAAAT<br>GAACAGCCTGAAACCTGAGGACACGGCCGTGTATTATTGTAACGCAGATTGGGGGTGGAGGAAC<br>TACTGGGGCCAGGGGACCCAGGTCACCGTCTCCAGCGGCCGCTACCCGTACGACGTTCCGGACT<br>ACGGTTCCGGCCGAGCATAG |
| 167 | 3yscf140 | CAGGTGCAGCTGCAGGAGTCTGGGGGAGGCTTGGTGCAGGCTGGGGGGTCTCTGAGACTCGCCT<br>GTGCAGCCTCTGGAGAGACTGTCGATGATCTTGCCATCGGCTGGTTCCGCCAGGCCCCAGGGAA<br>GGAGCGTGAGGAGATTTCATGTATTAGTGGTAGTGATGGTAGCACATACTATGCAGACTCCCTGT<br>CGGGCCGATTCACCATCTCCAGGGACAACGTCAAGAACACGGTGTATCTGCAAATGAACAGCCT<br>GAAACTTGAGGACACGGCCGTCTATTACTGTTATGCAGAGATTTACGATAGACGCTGGTATCGGA<br>ACGACTACTGGGGCCAGGGGACCCAGGTCACCGTCTCCAGCGGCCGCTACCCGTACGACGTTCC<br>GGACTACGGTTCCGGCCGAGCATAG |

TABLE 5

Y. pestis F1 SAb Protein Sequences

| SEQ ID NO | Name | Sequence |
|---|---|---|
| 168 | 3F55 | QVQLQESGGGLVQAGGSLRLSCAVSGMMYIREAIRWYRQAPGKQREWVAFVSSTGNPRYTDSVKG<br>RFTISRDNAKNTVYLQMNSLTPEDTAVYYCNTYLGSRDYWGQGTQVTVSS |
| 169 | 3F85 | QVQLQESGGGLVQPGGSLRLSCAVSGMMYIRYTMRWYRQAPGKQREWVAVVSSTGNPHYADSVK<br>GRFTISRDNAKNTVYLQMNSLTPEDTAVYYCNTYLGSRDYWGQGTQVTVSS |
| 170 | 3F44 | QVQLQESGGGLVRPGGSLRLSCAVSGRAVNRYHMHWYRQAPGKQREWVTFISVGGTTNYAGSVKG<br>RFTVSRDNAKNTLYLQMNSLKPEDTAVYYCNSAEYWGQGTQVTVSS |
| 171 | 4F34 | QVQLQESGGGSVQPGGSLSLSCSASGIIFSDYALTWYRQAPGKQREWVAQITRSQNINYTGSVKGRFT<br>VSRDNAKNTVHLQMNSLKPEDTAVYYCHAYDGRRPPYWGQGTQVTVSS |

TABLE 5-continued

Y. pestis F1 SAb Protein Sequences

| SEQ ID NO | Name | Sequence |
|---|---|---|
| 172 | 4F6 | QVQLQESGGGSVQPGGSLSLSCSASGIIFSDYALTWYRQAPGKQREWVAQITRSQNINYTGSVKGRFTVSRDNAKNTVHLQMNSLKPEDTAVYYCHAYDGRRRTYWGQGTQVTVSS |
| 173 | 4F1 | QVQLQESGGGLVQPGGSLSLSCSASGIIFSDYALTWYRQAPGKQREWVAQITRSQNINYTGSVKGRFTVSRDNAKNTVHLQMNSLKPEDTAVYYCHAYDGRRPPYWGQGTQVTVSS |
| 174 | 3F31 | QVQLQESGGGLVQPGGSLSLSCSASGIIFSDYALTWYRQAPGKQREWVAQITRRQNINYTGSVKGRFTVSRDNAKNTVHLQMNSLKPEDTAVYYCHAYDGRRSPYWGQGTQVTVSS |
| 175 | 3F61 | QVQLQESGGGLVQPGGSLRLSCSASGIIFSDYALTWYRQAPGKQREWVAQITRSQNINYTGSVKGRFTVSRDNAKNTVHLQMNSLKPEDAAVYYCHAYDGRRPPYWGQGTQVTVSS |
| 176 | 4F27 | QVQLQESGGGLVQPGGSLRLSCAASARIFSIYAMVWYRQAPGKQREWVAAITTGGTTNYADSVKGRFTISRDNAKNTVYLQMNSLKPEDTAVYYCNAPGYWGQGTQVTVSS |
| 177 | 3F26 | QVQLQESGGGLVQPGGSLRLSCAASGVIASISVLRWYRQTPGKTRDWVAIITSGGNTRYADSVKGRFTTSRDNARNTVYLQMNSLKPEDTAVYYCNTLVGAKDYWGQGTQVTVSS |
| 178 | 4F59 | QVQLQESGGGLVRPGGSLRLSCEASGTTFRSLVMKWYRQAPGKEREWVAFISSPGDRTRYTEAVKGRFTISRDNAKNALYLQMNGLKPEDTAVYYCNANGIYWGKGTQVTVSS |
| 179 | 3F5 | QVQLQESGGGLVQSGDSLRLSCAASGFTFSNYAMSWVRQAPGKGLEWVSTINSGGGSTSYAYSVKGRFTISRDNAKNTLYLQMNSLKPEDTAVYYCAKTASHIPLSQGTQVTVSS |
| 180 | 4F57 | QVQLQESGGGLVQPGGSLRLSCAASGFTFSNYAMSWVRQAPGKGLEWVSTINIGGGSTSYADSVKGRFTISRDNAKNTLYLQMNSLKPEDTAVYYCAKTASHIPLSQGTQVTVSS |
| 181 | 4F75 | QVQLQESGGGLVQPGGSLRLSCAASGFTFRNYAMSWVRQAPGKGLEWVSTINGGGGITSYADSVKGRFTISRDNAKNTMYLQMNSLKPEDTAVYYCAQTARDSRDSRGQGTQVTVSS |
| 182 | 3F59 | QVQLQESGGGLVQPGGSLRLSCAASGFTFSSYAMSWVRLAPGKGLEWVSTINIAGGITSYADSVKGRFTISRDNAKNTLYLQMNSLKPEDTAVYYCAKTAANWSAQRGQGTQVTVSS |
| 183 | 4F78 | QVQLQESGGGLVQPGGSLRLSCAASGFTFSSYAMSWVRQAPGKGLEWVSTINMGGGTTSYADSVKGRFTISRHNAKNTLYLQMNSLKPEDTAVYYCAKTAGNWSAQRGQGTQVTVSS |
| 184 | 3F1 | QVQLQESGGGLVQPGGSLRLSCAASGFTFSTSAMSWIRQPPGKAREVVATITSAGGSISYVNSVKGRFTISRDNAKNTLYLQMNMLKPEDTAVYYCARLVNLAQTGQGTQVTVSS |
| 185 | 3F65 | QVQLQESGGGLVQPGGSLRLSCAASGFTFSTNAMSWIRQPPGKAREVVATITSAGGSISYVNSVKGRFTISRDNAKNTLYLQMNMLKPEDTAVYYCARLVNLAQTGQGTQVTVSS |

TABLE 6

Y. pestis F1 SAb DNA Sequences

| SEQ ID NO | Name | Sequence |
|---|---|---|
| 186 | 3F55 | CAGGTGCAGCTGCAGGAGTCTGGGGGAGGCTTGGTGCAGGCTGGGGGCTCTCTGAGACTCTCCTGTGCAGTTTCTGGAATGATGTACATTAGGGAGGCTATACGCTGGTACCGCCAGGCTCCAGGGAAGCAGCGCGAGTGGGTCGCCTTTGTAAGTAGTACTGGTAATCCACGCTATACAGACTCCGTGAAGGGCCGATTCACCATCTCCAGAGACAACGCCAAGAACACGGTGTATCTGCAAATGAACAGCCTGACACCTGAGGACACGGCCGTCTATTACTGTAATACATACTTGGGCTCGAGGGACTACTGGGGCCAGGGGACCCAGGTCACCGTCTCCAGCGGCCGCTACCCGTACGACGTTCCGGACTACGGTTCCGGCCGAGCATAG |
| 187 | 3F85 | CAGGTGCAGCTGCAGGAGTCTGGAGGAGGCTTGGTGCAGCCTGGGGGGTCTCTGAGACTCTCCTGTGCAGTTTCTGGAATGATGTACATTAGGTACACTATGCGCTGGTACCGCCAGGCTCCAGGGAAGCAGCGCGAGTGGGTCGCCGTTGTAAGTAGTACTGGTAATCCACACTATGCAGACTCCGTGAAGGGCCGATTCACCATCTCCAGAGACAACGCCAAGAACACGGTGTATCTGCAAATGAACAGCCTGACACCTGAGGACACGGCCGTCTATTACTGTAATACATACTTGGGCTCGAGGGACTACTGGGGCCAGGGGACCCAGGTCACCGTCTCCAGCGGCCGCTACCCGTACGACGTTCCGGACTACGGTTCCGGCCGAGCATAG |
| 188 | 3F44 | CAGGTGCAGCTGCAGGAGTCTGGGGGAGGCTTGGTGCAGCCTGGGGGGTCTCTGAGACTCTCCTGTGCAGTCTCTGGAAGAGCCGTCAATAGGTATCACATGCACTGGTACCGCCAGGCTCCAGGGAAGCAGCGCGAGTGGGTCACATTTATTAGTGTTGGTGGTACCACAAACTATGCAGGCTCCGTGAAGGGCCGATTCACCGTCTCCCGAGACAACGCCAAAAACACGCTGTATCTGCAAATGAACAGCCTGAAACCTGAGGACACGGCCGTCTATTACTGTAATTCAGCTGAATACTGGGGCCAGGGGACCCAGGTCACCGTCTCCAGCGGCCGCTACCCGTACGACGTTCCGGACTACGGTTCCGGCCGAGCATAG |

TABLE 6-continued

Y. pestis F1 SAb DNA Sequences

| SEQ ID NO | Name | Sequence |
|---|---|---|
| 189 | 4F34 | CAGGTGCAGCTGCAGGAGTCTGGGGGAGGCTCGGTGCAGCCTGGGGGGTCTCTGAGCCTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGTCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACACGGCCGTCTACTATTGTCATGCATATGACGGTCGACGCCCACCCTACTGGGGCC<br>AGGGGACCCAGGTCACCGTCTCCAGCGGCCGCTACCCGTACGACGTTCCGGACTACGGTTCCGG<br>CCGAGCATAG |
| 190 | 4F6 | CAGGTGCAGCTGCAGGAGTCTGGGGGAGGCTCGGTGCAGCCTGGGGGGTCTCTGAGCCTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGCCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACACGGCCGTCTACTATTGTCATGCATATGACGGTCGACGCCGAACCTACTGGGGCC<br>AGGGGACCCAGGTCACCGTCTCCAGCGGCCGCTACCCGTACGACGTTCCGGACTACGGTTCCGG<br>CCGAGCATAG |
| 191 | 4F1 | CAGGTGCAGCTGCAGGAGTCTGGGGGAGGCTTGGTGCAGCCTGGGGGGTCTCTGAGCCTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGCCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACACGGCCGTCTACTATTGTCATGCATATGACGGTCGACGCCCACCCTACTGGGGCC<br>AGGGGACCCAGGTCACCGTCTCCAGCGGCCGCTACCCGTACGACGTTCCGGACTACGGTTCCGG<br>CCGAGCATAG |
| 192 | 3F31 | CAGGTGCAGCTGCAGGAGTCTGGGGGAGGCTTGGTGCAGCCTGGGGGGTCTCTGAGCCTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGGCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACACGGCCGTCTACTATTGTCATGCATATGACGGTCGACGATCACCCTACTGGGGCC<br>AGGGGACCCAGGTCACCGTCTCCAGCGGCCGCTACCCGTACGACGTTCCGGACTACGGTTCCGG<br>CCGAGCATAG |
| 193 | 3F61 | CAGGTGCAGCTGCAGGAGTCTGGGGGAGGCTTGGTGCAGCCTGGGGGGTCTCTGAGACTCTCCT<br>GTTCAGCCTCTGGAATCATCTTCAGTGACTATGCCCTGACCTGGTACCGCCAGGCTCCAGGGAAG<br>CAGCGCGAGTGGGTTGCACAGATTACGCGAAGTCAAAATATAAATTATACAGGATCCGTGAAGG<br>GCCGATTCACCGTCTCCAGAGACAACGCCAAGAACACAGTGCATCTGCAAATGAACAGCCTGAA<br>ACCTGAGGACGCGGCCGTCTACTATTGTCATGCATATGACGGTCGACGCCCACCCTACTGGGGCC<br>AGGGGACCCAGGTCACCGTCTCCAGCGGCCGCTACCCGTACGACGTTCCGGACTACGGTTCCGG<br>CCGAGCATAG |
| 194 | 4F27 | CAGGTGCAGCTGCAGGAGTCTGGGGGAGGCTTGGTGCAGCCTGGGGGGTCTCTGAGACTCTCCT<br>GTGCAGCCTCTGCCCGCATCTTCAGTATCTATGCCATGGTATGGTACCGCCAGGCTCCAGGGAAG<br>CAGCGCGAGTGGGTCGCAGCTATTACTACTGGTGGTACCACAAACTATGCAGACTCCGTGAAGG<br>GCCGATTCACCATCTCCAGAGACAACGCCAAGAACACGGTGTATCTGCAAATGAACAGCCTGAA<br>ACCTGAGGACACGGCCGTCTATTACTGTAATGCTCCGGGCTACTGGGGCCAGGGGACCCAGGTC<br>ACCGTCTCCAGCGGCCGCTACCCGTACGACGTTCCGGACTACGGTTCCGGCCGAGCATAG |
| 195 | 3F26 | CAGGTGCAGCTGCAGGAGTCTGGGGGAGGCTTGGTGCAGCCTGGGGGGTCTCTGAGACTCTCCT<br>GTGCAGCCTCTGGAGTCATCGCCAGTATCTCCGTCCTGCGCTGGTACCGCCAAACACCAGGAAAG<br>ACGCGCGACTGGGTCGCAATTATTACTAGTGGTGGCAACACACGCTATGCAGACTCCGTGAAGG<br>GCCGATTCACCACCTCCAGAGATAACGCCAGGAACACGGTGTATCTGCAAATGAACAGCCTGAA<br>ACCTGAGGACACGGCCGTCTATTACTGTAATACACTTGTAGGAGCCAAGGACTACTGGGGCCAG<br>GGGACCCAGGTCACCGTCTCCAGCGGCCGCTACCCGTACGACGTTCCGGACTACGGTTCCGGCCG<br>AGCATAG |
| 196 | 4F59 | CAGGTGCAGCTGCAGGAGTCTGGGGGAGGCTTGGTGCGGCCTGGGGATCTCTAAGACTCTCCT<br>GTGAAGCCTCTGGAACCACCTTCAGAAGCCTCGTAATGAAATGGTACCGCCAGGCTCCAGGGAA<br>GGAGCGCGAGTGGGTCGCATTTATTTCTAGTCCTGGTGATCGCACTCGCTACACAGAAGCCGTGA<br>AGGGCCGATTCACCATCTCCAGAGACAATGCCAAGAACGCGCTGTATCTGCAAATGAACGGCCT<br>GAAACCTGAGGACACGGCCGTGTATTATTGTAACGCGAACGGAATATACTGGGGCAAAGGGACC<br>CAGGTCACCGTCTCCAGCGGCCGCTACCCGTACGACGTTCCGGACTACGGTTCCGGCCGAGCATA<br>G |
| 197 | 3F5 | CAGGTGCAGCTGCAGGAGTCTGGGGGAGGCTTGGTGCAATCTGGGGATTCTCTGAGACTCTCCTG<br>TGCAGCCTCTGGATTCACCTTCAGTAACTATGCTATGAGCTGGTCCGCCAGGCTCCAGGAAAGG<br>GGCTCGAGTGGGTCTCAACTATTAATAGTGGTGGTGGTAGCACAAGCTATGCGTACTCCGTGAAG<br>GGCCGATTCACCATCTCCAGAGACAACGCCAAGAACACGCTGTATCTGCAAATGAACAGCCTGA<br>AACCTGAGGACACGGCCGTGTATTACTGTGCAAAGACGGCCTCTCACATACCCTTGAGCCAGGG<br>GACCCAGGTCACCGTCTCCAGCGGCCGCTACCCGTACGACGTTCCGGACTACGGTTCCGGCCGAG<br>CATAG |
| 198 | 4F57 | CAGGTGCAGCTGCAGGAGTCTGGGGGAGGCTTGGTGCAACCTGGGGGTTCTCTGAGACTCTCCT<br>GTGCAGCCTCTGGATTCACCTTCAGTAACTATGCTATGAGCTGGGTCCGCCAGGCTCCAGGAAAG<br>GGGCTCGAGTGGGTCTCAACTATTAATATTGGTGGTGGTAGCACAAGCTATGCAGACTCCGTGAA |

TABLE 6-continued

Y. pestis F1 SAb DNA Sequences

| SEQ ID NO | Name | Sequence |
|---|---|---|
| | | GGGCCGATTCACCATCTCCAGAGACAACGCCAAGAACACGCTGTATCTGCAAATGAACAGCCTG<br>AAACCTGAGGACACGGCCGTGTATTACTGTGCAAAGACGGCCTCTCACATACCCTTGAGCCAGG<br>GGACCCAGGTCACCGTCTCCAGCGGCCGCTACCCGTACGACGTTCCGGACTACGGTTCCGGCCGA<br>GCATAG |
| 199 | 4F75 | CAGGTGCAGCTGCAGGAGTCTGGGGGAGGCTTGGTGCAACCTGGGGGTTCTCTGAGACTCTCCT<br>GTGCAGCCTCTGGATTCACCTTCAGGAACTATGCAATGAGCTGGGTCCGTCAGGCTCCAGGAAA<br>GGGGCTCGAGTGGGTCTCAACTATTAATGGTGGTGGTATCACAAGCTATGCAGACTCCGTGA<br>AGGGCCGATTCACCATCTCCAGAGACAACGCCAAGAACACAATGTATCTGCAAATGAACAGCCT<br>GAAACCTGAGGACACGGCCGTCTATTACTGTGCCCAAACCGCCCGCGATTCCCGCGATTCCCGGG<br>GCCAGGGGACCCAGGTCACCGTCTCCAGCGGCCGCTACCCGTACGACGTTCCGGACTACGGTTCC<br>GGCCGAGCATAG |
| 200 | 3F59 | CAGGTGCAGCTGCAGGAGTCTGGGGGAGGCTTGGTGCAACCTGGGGGTTCTCTGAGACTCTCCT<br>GTGCAGCCTCTGGATTCACCTTCAGTAGCTATGCTATGAGCTGGGTCCGCCTGGCTCCAGGAAAG<br>GGGCTCGAGTGGGTCTCAACTATTAATATCGCTGGTGGTATCACAAGCTATGCAGACTCCGTGA<br>GGGCCGATTCACCATCTCCAGAGACAACGCCAAGAACACGCTGTATCTGCAAATGAACAGCCTG<br>AAACCTGAGGACACGGCCGTGTATTACTGTGCAAAAACGGCGGCCAACTGGAGCGCCCAGAGAG<br>GCCAGGGGACCCAGGTCACCGTCTCCAGCGGCCGCTACCCGTACGACGTTCCGGACTACGGTTCC<br>GGCCGAGCATAG |
| 201 | 4F78 | CAGGTGCAGCTGCAGGAGTCTGGGGGAGGCTTGGTGCAACCTGGGGGTTCTCTGAGACTCTCCT<br>GTGCAGCCTCTGGATTCACCTTCAGTAGCTATGCTATGAGCTGGGTCCGCCAGGCTCCAGGAAAG<br>GGGCTCGAGTGGGTCTCAACTATTAATATGGGTGGTGGTACCACAAGCTATGCAGACTCCGTGA<br>AGGGCCGATTCACCATCTCCAGACACAACGCCAAGAACACGCTGTATCTGCAAATGAACAGCCT<br>GAAACCTGAGGACACGGCCGTGTATTACTGTGCAAAAACGGCGGGCAACTGGAGCGCCCAGAG<br>AGGCCAGGGGACCCAGGTCACCGTCTCCAGCGGCCGCTACCCGTACGACGTTCCGGACTACGGT<br>TCCGGCCGAGCATAG |
| 202 | 3F1 | CAGGTGCAGCTGCAGGAGTCTGGGGGAGGCTTGGTGCAACCTGGGGGTTCTCTGAGACTGTCCT<br>GTGCAGCCTCTGGATTCACCTTCAGTACAAGTGCCATGAGTTGGATCCGCCAGCCTCCAGGGAAG<br>GCGCGCGAGGTGGTCGCAACTATTACTAGTGCTGGTGGTAGTATAAGTTATGTAAACTCCGTGAA<br>GGGCCGATTCACCATCTCCAGAGACAACGCCAAGAACGCTGTATCTGCAAATGAACAGCTG<br>AAACCTGAGGACACGGCCGTGTATTACTGTGCCCGACTGGTCAACCTTGCCCAGACCGGCCAGG<br>GAACCCAGGTCACCGTCTCCAGCGGCCGCTACCCGTACGACGTTCCGGACTACGGTTCCGGCCGA<br>GCATAG |
| 203 | 3F65 | CAGGTGCAGCTGCAGGAGTCTGGGGGAGGCCTGGTGCAACCTGGGGGTTCTCTGAGACTGTCCT<br>GTGCAGCCTCTGGATTCACCTTCAGTACAAATGCCATGAGTTGGATCCGCCAGCCTCCAGGGAAG<br>GCGCGCGAGGTGGTCGCAACTATTACTAGTGCTGGTGGTAGTATAAGTTATGTAAACTCCGTGAA<br>GGGCCGATTCACCATCTCCAGAGACAACGCCAAGAACACGCTGTATCTGCAAATGAACATGCTG<br>AAACCTGAGGACACGGCCGTGTATTACTGTGCCCGACTGGTCAACCTTGCCCAGACCGGCCAGG<br>GGACCCAGGTCACCGTCTCCAGCGGCCGCTACCCGTACGACGTTCCGGACTACGGTTCCGGCCGA<br>GCATAG |

TABLE 7

Y. pestis LcrV SAb Protein Sequences

| SEQ ID NO | Name | Sequence |
|---|---|---|
| 204 | 1LCRV32 | QVQLQESGGGMVEPGGSLRLSCAASGFRFSSYAMSWVRQAPGKGLERVSAINSDGDKTSYADSVKG<br>RFTISRDNARNTLYLQMSNLKPEDTAVYYCADRDLYCSGSMCKDVLGGARYDFRGQGTQVTVSS |
| 205 | 2LCRV4 | QVQLQESGGGLVEPGGSLRLSCAASGFRFSSYAMSWVRQAPGKGLERVSAINSDGDKTSYADSVKG<br>RFTISRDNARNTLYLQMSNLKPEDTAVYYCADRDLYCSGSMCKDVLGGARYDFRGQGTQVTVSS |
| 206 | 2LCRV3 | QVQLQESGGGMVEPGGSLRLSCAASGFRFSSYAMSWVRQAPGKGLERVSAINSDGDKTSYADSVKG<br>RFTISRDNARNTLYLQMNNLKPEDTAVYYCADRDLYCSGSMCKDVLGGARYDFRGQGTQVTVSS |
| 207 | 1LCRV52 | QVQLQESGGGLVQSGESLRLSCAASGLRFSSYAMSWVRQAPGKGLERVSAINSDGDKTSYADSVKG<br>RFTISRDNARNTLYLQMSNLKPEDTAVYYCADRDLYCSGSMCKDVLGGARYDFRGQGTQVTVSS |
| 208 | 1LCRV4 | QVQLQESGGGLVQPGGSLKLSCAASGFTFNWYTMAWYRQVPGEERKMVATITGASGDTKYADSVK<br>GRFTISRDNAKNTVTLQMNSLKPGDAAVYYCHAYLTYDSGSVKGVNYWGQGTQVTVSS |
| 209 | 1LCRV13 | QVQLQESGGGLVRPGGSLKLSCAASGFTFNWYTMAWYRQVPGEERKMVATITGASGDTKYADSVK<br>GRFTISRDNAKNTVTLQMNSLKPGDTAVYYCHAYLTYDSGSVKGVNYWGQGTQVTVSS |
| 210 | 2LCRV1 | QVQLQESGGGSVQPGGSLKLSCAASGFTFNWYTMAWYRQVPGEERKMVATITGASGDTKYADSVK<br>GRFTISRDNAKNTVTLQMNSLKPGDTAVYYCHAYLTYDSGSVKGVNYWGQGTQVTVSS |

TABLE 7-continued

Y. pestis LcrV SAb Protein Sequences

| SEQ ID NO | Name | Sequence |
|---|---|---|
| 211 | 1LCRV81 | QVQLQESGGGSVQPGGSLKLSCAASGFTFNWYTMAWYRQVPGEERKMVATITGASGDTKYADSVK GRSTISRDNAKNTVTLQMNSLKPGDTAVYYCHACLTYDSGSVKGVNYWGQGTQVTVSS |
| 212 | 1LCRV27 | QVQLQESGGGFVQPGGSLKLSCAASGFTFNWYTMAWYRQVPGEERKMVATITGASGDTKYADSVK GRFTISRDNAKNTVTLQMNSLKPGDTAVYYCHAYLTYDSGSVKGVNYWGQGTQVTVSS |
| 213 | 1LCRV34 | QVQLQESGGGLVQPGGSLKLSCAASGFTFNWYTMAWYRQVPGEERKMVATITGASGDTKYADSVK GRFTISRDNAKNTVTLQMNSLKPGDTAVYYCHAYLTYDSGSAKGVNYWGQGTQVTVSS |
| 214 | 1LCRV31 | QVQLQESGGGLVQPGGSLGLSCAASGSLLNIYAMGWYRQAPGRQRELVATVTSSGTAEYADSVKGR FTISRDNAKNTVYLQMNSLRPEDTGVYYCNAHLRYGDYVRGPPEYNYWGQGTQVTVSS |
| 215 | 1LCRV28 | QVQLQESGGGLVQPGGSLRLSCAASGGTLGYYAIGWFRQAPGKEREAVSCITSSDTSAYYADSAKGR FTISRDNAKNTMYLQMNNLKPEDTAVYYCAAGYYFRDYSDSYYYTGTGMKVWGKGTQVTVSS |
| 216 | 2LCRV11 | QVQLQESGGGLVQPGGSTRLSCAASGFTLDIYAIGWFRQAPGKEHEGVSWIVGNDGRTYYIDSVKGR FTISRDNAKNTVYLEMNSLKPEDTAVYYCAAKFWPRYYSGRPPVGRDGYDYWGQGTQVTVSS |
| 217 | 1LCRV47 | QVQLQESGGGLVQPGGSLILSCTISGASLRDRRVTWSRQGPGKSLEIIAVMAPDYGVHYFGSLEGRVA VRGDVVKNTVYLQVNALKPEDTAIYWCSMGNIRGLGTQVTVSS |

TABLE 8

Y. pestis LcrV SAb DNA Sequences

| SEQ ID NO | Name | Sequence |
|---|---|---|
| 218 | 1LCRV32 | CAGGTGCAGCTGCAGGAGTCTGGGGGAGGCATGGTAGAACCTGGGGGTTCTCTGAGACTCTCCT GTGCAGCCTCTGGATTCCGCTTCAGTAGTTATGCTATGAGTTGGGTCCGCCAGGCTCCAGGAAAG GGGCTCGAGCGGGTCTCGGCTATTAATAGTGATGGTGATAAAACAAGCTATGCAGACTCCGTGA AGGGCCGATTTACCATCTCCAGAGACAACGCCAGGAACACGCTGTATCTGCAAATGAGCAACCT GAAACCTGAAGACACGGCCGTGTATTACTGTGCAGACCGAGATTTGTACTGTTCAGGCTCTATGT GTAAGGACGTCTTGGGGGGAGCACGCTATGACTTTCGGGGCCAGGGGACCCAGGTCACCGTCTC CAGCGGCCGCTACCCGTACGACGTTCCGGACTACGGTTCCGGCCGAGCATAG |
| 219 | 2LCRV4 | CAGGTGCAGCTGCAGGAGTCTGGAGGAGGCTTGGTAGAACCTGGGGGTTCTCTGAGACTCTCCT GTGCAGCCTCTGGATTCCGCTTCAGTAGTTATGCTATGAGTTGGGTCCGCCAGGCTCCAGGAAAG GGGCTCGAGCGGGTCTCAGCTATTAATAGTGATGGTGATAAAACAAGCTATGCAGACTCCGTGA AGGGCCGATTTACCATCTCCAGAGACAACGCCAGGAACACGCTGTATCTGCAAATGAGCAACCT GAAACCTGAAGACACGGCCGTGTATTACTGTGCAGACCGAGATTTGTACTGTTCAGGCTCTATGT GTAAGGACGTCTTGGGGGGAGCACGCTATGACTTTCGGGGCCAGGGGACCCAGGTCACCGTCTC CAGCGGCCGCTACCCGTACGACGTTCCGGACTACGGTTCCGGCCGAGCATAG |
| 220 | 2LCRV3 | CAGGTGCAGCTGCAGGAGTCTGGGGGAGGCATGGTAGAACCTGGGGGTTCTCTGAGACTCTCTTGT GCAGCCTCTGGATTCCGCTTCAGTAGTTATGCTATGAGTTGGGTCCGCCAGGCTCCAGGAAAGGGG CTCGAGCGGGTCTCGGCTATTAATAGTGATGGTGATAAAACAAGCTATGCAGACTCCGTGAAGGGC CGATTCACCATCTCCAGAGACAACGCCAGGAACACGCTGTATCTGCAAATGAACAACCTGAAACCT GAAGACACGGCCGTGTATTACTGTGCAGACCGAGATTTGTACTGTTCGGGCTCTATGTGTAAGGAC GTCTTGGGGGGAGCACGCTATGACTTTCGGGGCCAGGGGACCCAGGTCACCGTCTCCAGCGGCCGC TACCCGTACGACGTTCCGGACTACGGTTCCGGCCGAGCATAG |
| 221 | 1LCRV52 | CAGGTGCAGCTGCAGGAGTCTGGGGGAGGCTTGGTGCAGTCTGGCGAGTCTCTCAGACTCTCCTG TGCAGCCTCTGGACTCCGCTTCAGTAGTTATGCTATGAGTTGGGTCCGCCAGGCTCCAGGAAAGG GGCTCGAGCGGGTCTCGGCTATTAATAGTGATGGTGATAAAACAAGCTATGCAGACTCCGTGAA GGGCCGATTTACCATCTCCAGAGACAACGCCAGGAACACGCTGTATCTGCAAATGAGCAACCTG AAACCTGAAGACACGGCCGTGTATTACTGTGCAGACCGAGATTTGTACTGTTCAGGCTCTATGTG TAAGGACGTCTTGGGGGGAGCACGCTATGACTTTCGGGGCCAGGGGACCCAGGTCACCGTCTCC AGCGGCCGCTACCCGTACGACGTTCCGGACTACGGTTCCGGCCGAGCATAG |
| 222 | 1LCRV4 | CAGGTGCAGCTGCAGGAGTCTGGAGGAGGCCTGGTGCAGCCTGGGGGTCTCTGAAACTCTCCT GTGCAGCCTCTGGATTCACCTTCAATTGGTATACCATGGCCTGGTATCGCCAGGTTCCAGGGGAG GAGCGCAAAATGGTCGCCACAATTACAGGTGCTAGTGGTGACACAAAATATGCAGACTCCGTGA AGGGCCGGTTCACCATCTCCAGAGACAATGCCAAGAACACGGTGACACTGCAAATGAACAGCCT TAAACCTGGAGACGCGGCCGTCTATTACTGTCATGCCTACCTAACCTACGACTCGGGGTCCGTCA AAGGAGTTAACTACTGGGGCCAGGGGACCCAGGTCACCGTCTCCAGCGGCCGCTACCCGTACGA CGTTCCGGACTACGGTTCCGGCCGAGCATAG |
| 223 | 1LCRV13 | CAGGTGCAGCTGCAGGAGTCTGGGGGAGGCTTGGTGCGGCCTGGGGGTCTCTGAAACTCTCCT GTGCAGCCTCTGGATTCACCTTCAATTGGTATACCATGGCCTGGTATCGCCAGGTTCCAGGGGAG GAGCGCAAAATGGTCGCCACAATTACAGGTGCTAGTGGTGACACAAAATATGCAGACTCCGTGA |

TABLE 8-continued

Y. pestis LcrV SAb DNA Sequences

| SEQ ID NO | Name | Sequence |
|---|---|---|
| | | AGGGCCGGTTCACCATCTCCAGAGACAATGCCAAGAACACGGTGACACTGCAAATGAACAGCCT<br>TAAACCTGGAGACACGGCCGTCTATTACTGTCATGCCTACCTAACCTACGACTCGGGGTCCGTCA<br>AAGGAGTTAACTACTGGGGCCAGGGGACCCAGGTCACCGTCTCCAGCGGCCGCTACCCGTACGA<br>CGTTCCGGACTACGGTTCCGGCCGAGCATAG |
| 224 | 2LCRV1 | CAGGTGCAGCTGCAGGAGTCTGGGGGAGGCTCGGTGCAGCCTGGGGGGTCTCTGAAACTCTCCT<br>GTGCAGCCTCTGGATTCACCTTCAATTGGTATACCATGGCCTGGTATCGCCAGGTTCCAGGGGAG<br>GAGCGCAAAATGGTTGCCACAATTACAGGTGCTAGTGGTGACACAAAATATGCAGACTCCGTGA<br>AGGGCCGGTTCACCATCTCCAGAGACAATGCCAAGAACACGGTGACACTGCAAATGAACAGCCT<br>TAAACCTGGAGACACGGCCGTCTATTACTGTCATGCCTACCTAACCTACGACTCGGGGTCCGTCA<br>AAGGAGTTAACTACTGGGGCCAGGGGACCCAGGTCACCGTCTCCAGCGGCCGCTACCCGTACGA<br>CGTTCCGGACTACGGTTCCGGCCGAGCATAG |
| 225 | 1LCRV81 | CAGGTGCAGCTGCAGGAGTCTGGGGGAGGCTCGGTGCAGCCTGGGGGGTCTCTGAAACTCTCCT<br>GTGCAGCCTCTGGATTCACCTTCAATTGGTATACCATGGCCTGGTATCGCCAGGTTCCAGGGGAG<br>GAGCGCAAAATGGTCGCCACAATTACAGGTGCTAGTGGTGACACAAAATATGCAGACTCCGTGA<br>AGGGCCGGTCCACCATCTCCAGAGACAATGCCAAGAACACGGTGACACTGCAAATGAACAGCCT<br>TAAACCTGGAGACACGGCCGTCTATTACTGTCATGCCTGCCTAACCTACGACTCGGGGTCCGTCA<br>AAGGAGTTAACTACTGGGGTCAGGGGACCCAGGTCACCGTCTCCAGCGGCCGCTACCCGTACGA<br>CGTTCCGGACTACGGTTCCGGCCGAGCATAG |
| 226 | 1LCRV27 | CAGGTGCAGCTGCAGGAGTCTGGGGGAGGCTTCGTGCAGCCTGGGGGGTCTCTGAAACTCTCCT<br>GTGCAGCCTCTGGATTCACCTTCAATTGGTATACCATGGCCTGGTATCGCCAGGTTCCAGGGGAG<br>GAGCGCAAAATGGTCGCCACAATTACAGGTGCTAGTGGTGACACAAAATATGCAGACTCCGTGA<br>AGGGCCGGTTCACCATCTCCAGAGACAATGCCAAGAACACGGTGACACTGCAAATGAACAGCCT<br>TAAACCTGGAGACACGGCCGTCTATTACTGTCATGCCTACCTAACCTACGACTCGGGGTCCGTCA<br>AAGGAGTTAACTACTGGGGCCAGGGGACCCAGGTCACCGTCTCCAGCGGCCGCTACCCGTACGA<br>CGTTCCGGACTACGGTTCCGGCCGAGCATAG |
| 227 | 1LCRV34 | CAGGTGCAGCTGCAGGAGTCTGGGGGAGGCCTGGTGCAGCCTGGGGGGTCTCTGAAACTCTCCT<br>GTGCAGCCTCTGGATTCACCTTCAATTGGTATACCATGGCCTGGTATCGCCAGGTTCCAGGGGAG<br>GAGCGCAAAATGGTCGCCACAATTACAGGTGCTAGTGGTGACACAAAATATGCAGACTCCGTGA<br>AGGGCCGGTTCACCATCTCCAGAGACAATGCCAAGAACACGGTGACACTGCAAATGAACAGCCT<br>TAAACCTGGAGACACGGCCGTCTATTACTGTCATGCCTACCTAACCTACGACTCGGGGTCCGCCA<br>AAGGAGTTAACTACTGGGGCCAGGGGACCCAGGTCACCGTCTCCAGCGGCCGCTACCCGTACGA<br>CGTTCCGGACTACGGTTCCGGCCGAGCATAG |
| 228 | 1LCRV31 | CAGGTGCAGCTGCAGGAGTCTGGGGGAGGCTTGGTGCAGCCTGGGGGGTCTCTAGGACTCTCCT<br>GTGCAGCCTCTGGAAGCCTCTTAAATATCTATGCCATGGGCTGGTACCGCCAGGCTCCAGGGAGA<br>CAGCGCGAGTTGGTCGCAACTGTAACGAGTAGTGGAACCGCAGAATATGCAGACTCCGTGAAGG<br>GCCGATTCACCATCTCTAGAGACAACGCCAAGAACACGGTGTATCTGCAAATGAACAGCCTGAG<br>ACCTGAGGACACGGGCGTCTATTACTGTAATGCACATCTCAGATATGGCGACTATGTCCGTGGCC<br>CTCCGGAGTATAACTACTGGGGCCAGGGGACCCAGGTCACCGTCTCCAGCGGCCGCTACCCGTA<br>CGACGTTCCGGACTACGGTTCCGGCCGAGCATAG |
| 229 | 1LCRV28 | CAGGTGCAGCTGCAGGAGTCTGGGGGAGGCTTGGTGCAGCCTGGGGGGTCTCTGAGACTCTCCT<br>GTGCAGCCTCTGGAGGCACTTTGGGTTACTATGCCATAGGCTGGTTCCGCCAGGCCCCAGGGAAG<br>GAGCGCGAGGCGGTCTCCTGTATTACTAGTAGTGACACTAGCGCATACTATGCAGACTCCGCGA<br>AGGGCCGATTCACCATCTCCAGAGACAACGCCAAGAACACGATGTATCTGCAAATGAACAACCT<br>GAAACCTGAGGACACAGCCGTTTATTACTGTGCAGCCGGTTACTATTTTAGAGACTATAGTGACA<br>GTTACTACTACACGGGGACGGGTATGAAAGTCTGGGCAAAGGGACCCAGGTCACCGTCTCCAG<br>CGGCCGCTACCCGTACGACGTTCCGGACTACGGTTCCGGCCGAGCATAG |
| 230 | 2LCRV11 | CAGGTGCAGCTGCAGGAGTCTGGGGGAGGCTTGGTGCAGCCTGGGGGGTCTACGAGACTCTCCT<br>GTGCAGCCTCTGGATTCACTTTGGATATTTATGCTATAGGCTGGTTCCGCCAGGCCCCAGGGAAG<br>GAGCATGAGGGGGTCTCGTGGATTGTTGGTAATGATGGTAGGACATACTACATAGACTCCGTGA<br>AGGGCCGATTCACCATCTCCAGAGACAACGCCAAGAACACGGTGTATCTTGAAATGAACAGCCT<br>GAAACCTGAGGATACAGCCGTTTATTACTGCGCAGCTAAGTTCTGGCCCCGATATTATAGTGGTA<br>GGCCTCCAGTAGGGAGGGATGGCTATGACTATTGGGCCAGGGGACCCAGGTCACCGTCTCCAG<br>CGGCCGCTACCCGTACGACGTTCCGGACTACGGTTCCGGCCGAGCATAG |
| 231 | 1LCRV47 | CAGGTGCAGCTGCAGGAGTCTGGGGGAGGCTTGGTGCAGCCTGGCGGGTCTCTGATACTCCTG<br>TACAATCTCGGGAGCCTCGCTCCGAGACCGACGCGTCACCTGGAGTCGCCAAGGTCAGGGAAA<br>TCGCTTGAGATCATCGCAGTTATGGCGCCGGATTACGGGGTCCATTACTTTGGCTCCCTGGAGGG<br>GCGAGTTGCCGTCCGAGGAGACGTCGTCAAGAATACAGTATATCTCCAAGTAAACGCCCTGAAA<br>CCCGAAGACACAGCCATCTATTGGTGCAGTATGGGGAATATCCGGGGCCTGGGGACCCAGGTCA<br>CCGTCTCCAGCGGCCGCTACCCGTACGACGTTCCGGACTACGGTTCCGGCCGAGCATAG |

TABLE 9

F1 SAb Groups

| Group | Name | SEQ ID NO |
|---|---|---|
| 1 | 3F55, 3F85 | 168, 169 |
| 2 | 3F44 | 170 |
| 3 | 3F31, 3F61, 4F1, 4F6, 4F34 | 171-175 |
| 4 | 4F27 | 176 |
| 5 | 3F26 | 177 |
| 6 | 4F59 | 178 |
| 7 | 3F5, 4F57 | 179-180 |
| 8 | 4F75 | 181 |
| 9 | 3F59, 4F78 | 182-183 |
| 10 | 3F1, 3F65 | 184-185 |

TABLE 10

LcrV SAb Groups

| Group | Name | SEQ ID NO |
|---|---|---|
| 1 | 1LCRV32, 2LCRV4, 2LCRV3, 1LCRV52 | 204-207 |
| 2 | 1CLRV4, 1LCRV13, 2LCRV1, 1LCRV81, 1LCRV27, 1LCRV34 | 208-213 |
| 3 | 1LCRV31 | 214 |
| 4 | 1LCRV28 | 215 |
| 5 | 2LCRV11 | 216 |
| 6 | 1LCRV47 | 217 |

TABLE 11

Binding Kinetics of LcrV and F1 Sabs

| Name | SEQ ID NO | BIACORE $K_D$ (nM) | Microcal $K_D$ (nM) |
|---|---|---|---|
| 1LCRV13 | 209 | 0.00063 | 3.2 |
| 1LCRV28 | 215 | 0.19 | 0.20 |
| 1LCRV31 | 214 | 0.0019 | 0.76 |
| 1LCRV32 | 204 | 22 | 26 |
| 1LCRV47 | 217 | >1000 | no heat |
| 1LCRV81 | 211 | 3.5 | Error |
| 2LCRV11 | 216 | 8.2 | Error |
| 3F1 | 184 | 97 | 110 |
| 3F5 | 179 | 47 | 83 |
| 3F26 | 177 | — | — |
| 3F44 | 170 | — | — |
| 3F55 | 168 | 2.2 | 190 |
| 3F59 | 182 | 5.9 | no heat |
| 3F61 | 175 | 68 | 290 |
| 3F85 | 169 | 15 | 110 |
| 4F1 | 173 | 520 | error |
| 4F6 | 172 | 34 | 80 |
| 4F27 | 176 | — | — |
| 4F34 | 171 | 390 | error |
| 4F59 | 178 | 27 | 83 |
| 4F75 | 181 | 6/9 | error |
| 4F78 | 183 | 6/28 | error |

TABLE 12

Binding Constants of LcrV SAbs

| Name | SEQ ID NO | $k_a$ (M$^{-1}$ s$^{-1}$) | $k_d$ (s$^{-1}$) | $K_D$ (nM) |
|---|---|---|---|---|
| 1LCRV13 | 209 | $2.5 \times 10^5$ | $1.6 \times 10^{-6}$ | 0.00063 |
| 1LCRV28 | 215 | $4.3 \times 10^5$ | $8.1 \times 10^{-5}$ | 0.19 |
| 1LCRV31 | 214 | $1.7 \times 10^5$ | $3.1 \times 10^{-7}$ | 0.0019 |
| 1LCRV32 | 204 | $3.4 \times 10^5$ | $7.3 \times 10^{-3}$ | 22 |
| 1LCRV47 | 217 | n.b. | n.b. | — |
| 1LCRV81 | 211 | $1.8 \times 10^5$ | $6.3 \times 10^{-4}$ | 3.5 |
| 2LCRV11 | 216 | $8.8 \times 10^5$ | $7.2 \times 10^{-3}$ | 8.2 |

Although specific embodiments have been described in detail in the foregoing description and illustrated in the drawings, various other embodiments, changes, and modifications to the disclosed embodiment(s) will become apparent to those skilled in the art. All such other embodiments, changes, and modifications are intended to come within the spirit and scope of the appended claims.

---

SEQUENCE LISTING

---

```
Sequence total quantity: 231
SEQ ID NO: 1            moltype = AA  length = 10
FEATURE                 Location/Qualifiers
REGION                  1..10
                        note = Generated by phage peptide display
source                  1..10
                        mol_type = protein
                        organism = synthetic construct
SEQUENCE: 1
GRTWRAYYMG                                                           10

SEQ ID NO: 2            moltype = AA  length = 10
FEATURE                 Location/Qualifiers
REGION                  1..10
                        note = Generated by phage peptide display
source                  1..10
                        mol_type = protein
                        organism = synthetic construct
SEQUENCE: 2
GRAFSNYAMA                                                           10

SEQ ID NO: 3            moltype = AA  length = 10
FEATURE                 Location/Qualifiers
REGION                  1..10
                        note = Generated by phage peptide display
source                  1..10
                        mol_type = protein
```

```
                        organism = synthetic construct
SEQUENCE: 3
GRTFSRYAMG                                                              10

SEQ ID NO: 4            moltype = AA   length = 10
FEATURE                 Location/Qualifiers
REGION                  1..10
                        note = Generated by phage peptide display
source                  1..10
                        mol_type = protein
                        organism = synthetic construct
SEQUENCE: 4
QRTFSRYSLG                                                              10

SEQ ID NO: 5            moltype = AA   length = 10
FEATURE                 Location/Qualifiers
REGION                  1..10
                        note = Generated by phage peptide display
source                  1..10
                        mol_type = protein
                        organism = synthetic construct
SEQUENCE: 5
GRTFSSHAMA                                                              10

SEQ ID NO: 6            moltype = AA   length = 13
FEATURE                 Location/Qualifiers
REGION                  1..13
                        note = Generated by phage peptide display
source                  1..13
                        mol_type = protein
                        organism = synthetic construct
SEQUENCE: 6
GRTFGRPFRY TMG                                                          13

SEQ ID NO: 7            moltype = AA   length = 10
FEATURE                 Location/Qualifiers
REGION                  1..10
                        note = Generated by phage peptide display
source                  1..10
                        mol_type = protein
                        organism = synthetic construct
SEQUENCE: 7
GETVDDLAIG                                                              10

SEQ ID NO: 8            moltype = AA   length = 10
FEATURE                 Location/Qualifiers
REGION                  1..10
                        note = Generated by phage peptide display
source                  1..10
                        mol_type = protein
                        organism = synthetic construct
SEQUENCE: 8
GMMYIREAIR                                                              10

SEQ ID NO: 9            moltype = AA   length = 10
FEATURE                 Location/Qualifiers
REGION                  1..10
                        note = Generated by phage peptide display
source                  1..10
                        mol_type = protein
                        organism = synthetic construct
SEQUENCE: 9
GMMYIRYTMR                                                              10

SEQ ID NO: 10           moltype = AA   length = 10
FEATURE                 Location/Qualifiers
REGION                  1..10
                        note = Generated by phage peptide display
source                  1..10
                        mol_type = protein
                        organism = synthetic construct
SEQUENCE: 10
GRAVNRYHMH                                                              10

SEQ ID NO: 11           moltype = AA   length = 10
FEATURE                 Location/Qualifiers
REGION                  1..10
                        note = Generated by phage peptide display
source                  1..10
```

```
                            mol_type = protein
                            organism = synthetic construct
SEQUENCE: 11
GIIFSDYALT                                                              10

SEQ ID NO: 12               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 12
ARIFSIYAMV                                                              10

SEQ ID NO: 13               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 13
GVIASISVLR                                                              10

SEQ ID NO: 14               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 14
GTTFRSLVMK                                                              10

SEQ ID NO: 15               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 15
GFTFSNYAMS                                                              10

SEQ ID NO: 16               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 16
GFTFRNYAMS                                                              10

SEQ ID NO: 17               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 17
GFTFSSYAMS                                                              10

SEQ ID NO: 18               moltype = AA  length = 10
FEATURE                     Location/Qualifiers
REGION                      1..10
                            note = Generated by phage peptide display
source                      1..10
                            mol_type = protein
                            organism = synthetic construct
SEQUENCE: 18
GFTFSTSAMS                                                              10

SEQ ID NO: 19               moltype = AA  length = 10
FEATURE                     Location/Qualifiers
REGION                      1..10
                            note = Generated by phage peptide display
```

```
source                    1..10
                          mol_type = protein
                          organism = synthetic construct
SEQUENCE: 19
GFTFSTNAMS                                                                        10

SEQ ID NO: 20             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 20
GFRFSSYAMS                                                                        10

SEQ ID NO: 21             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 21
GLRFSSYAMS                                                                        10

SEQ ID NO: 22             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 22
GFTFNWYTMA                                                                        10

SEQ ID NO: 23             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 23
GSLLNIYAMG                                                                        10

SEQ ID NO: 24             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 24
GGTLGYYAIG                                                                        10

SEQ ID NO: 25             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 25
GFTLDIYAIG                                                                        10

SEQ ID NO: 26             moltype = AA   length = 10
FEATURE                   Location/Qualifiers
REGION                    1..10
                          note = Generated by phage peptide display
source                    1..10
                          mol_type = protein
                          organism = synthetic construct
SEQUENCE: 26
GASLRDRRVT                                                                        10

SEQ ID NO: 27             moltype = AA   length = 17
FEATURE                   Location/Qualifiers
REGION                    1..17
```

```
                              note = Generated by phage peptide display
source                        1..17
                              mol_type = protein
                              organism = synthetic construct
SEQUENCE: 27
VMSRSGGTTS YADSVKG                                                              17

SEQ ID NO: 28                 moltype = AA   length = 17
FEATURE                       Location/Qualifiers
REGION                        1..17
                              note = Generated by phage peptide display
source                        1..17
                              mol_type = protein
                              organism = synthetic construct
SEQUENCE: 28
ANWRSGGLTD YADSVKG                                                              17

SEQ ID NO: 29                 moltype = AA   length = 17
FEATURE                       Location/Qualifiers
REGION                        1..17
                              note = Generated by phage peptide display
source                        1..17
                              mol_type = protein
                              organism = synthetic construct
SEQUENCE: 29
AISWSGSSTY YADSVKG                                                              17

SEQ ID NO: 30                 moltype = AA   length = 17
FEATURE                       Location/Qualifiers
REGION                        1..17
                              note = Generated by phage peptide display
source                        1..17
                              mol_type = protein
                              organism = synthetic construct
SEQUENCE: 30
ATTWSGISSD YADSVKG                                                              17

SEQ ID NO: 31                 moltype = AA   length = 17
FEATURE                       Location/Qualifiers
REGION                        1..17
                              note = Generated by phage peptide display
source                        1..17
                              mol_type = protein
                              organism = synthetic construct
SEQUENCE: 31
AIRWNGDNIH YSDSAKG                                                              17

SEQ ID NO: 32                 moltype = AA   length = 17
FEATURE                       Location/Qualifiers
REGION                        1..17
                              note = Generated by phage peptide display
source                        1..17
                              mol_type = protein
                              organism = synthetic construct
SEQUENCE: 32
GITRSGNNIY YSDSVKG                                                              17

SEQ ID NO: 33                 moltype = AA   length = 17
FEATURE                       Location/Qualifiers
REGION                        1..17
                              note = Generated by phage peptide display
source                        1..17
                              mol_type = protein
                              organism = synthetic construct
SEQUENCE: 33
CISGSDGSTY YADSLSG                                                              17

SEQ ID NO: 34                 moltype = AA   length = 16
FEATURE                       Location/Qualifiers
REGION                        1..16
                              note = Generated by phage peptide display
source                        1..16
                              mol_type = protein
                              organism = synthetic construct
SEQUENCE: 34
FVSSTGNPRY TDSVKG                                                               16

SEQ ID NO: 35                 moltype = AA   length = 16
FEATURE                       Location/Qualifiers
```

```
REGION                    1..16
                          note = Generated by phage peptide display
source                    1..16
                          mol_type = protein
                          organism = synthetic construct
SEQUENCE: 35
VVSSTGNPHY ADSVKG                                                        16

SEQ ID NO: 36             moltype = AA  length = 16
FEATURE                   Location/Qualifiers
REGION                    1..16
                          note = Generated by phage peptide display
source                    1..16
                          mol_type = protein
                          organism = synthetic construct
SEQUENCE: 36
FISVGGTTNY AGSVKG                                                        16

SEQ ID NO: 37             moltype = AA  length = 16
FEATURE                   Location/Qualifiers
REGION                    1..16
                          note = Generated by phage peptide display
source                    1..16
                          mol_type = protein
                          organism = synthetic construct
SEQUENCE: 37
QITRSQNINY TGSVKG                                                        16

SEQ ID NO: 38             moltype = AA  length = 16
FEATURE                   Location/Qualifiers
REGION                    1..16
                          note = Generated by phage peptide display
source                    1..16
                          mol_type = protein
                          organism = synthetic construct
SEQUENCE: 38
QITRRQNINY TGSVKG                                                        16

SEQ ID NO: 39             moltype = AA  length = 16
FEATURE                   Location/Qualifiers
REGION                    1..16
                          note = Generated by phage peptide display
source                    1..16
                          mol_type = protein
                          organism = synthetic construct
SEQUENCE: 39
AITTGGTTNY ADSVKG                                                        16

SEQ ID NO: 40             moltype = AA  length = 16
FEATURE                   Location/Qualifiers
REGION                    1..16
                          note = Generated by phage peptide display
source                    1..16
                          mol_type = protein
                          organism = synthetic construct
SEQUENCE: 40
IITSGGNTRY ADSVKG                                                        16

SEQ ID NO: 41             moltype = AA  length = 17
FEATURE                   Location/Qualifiers
REGION                    1..17
                          note = Generated by phage peptide display
source                    1..17
                          mol_type = protein
                          organism = synthetic construct
SEQUENCE: 41
FISSPGDRTR YTEAVKG                                                       17

SEQ ID NO: 42             moltype = AA  length = 17
FEATURE                   Location/Qualifiers
REGION                    1..17
                          note = Generated by phage peptide display
source                    1..17
                          mol_type = protein
                          organism = synthetic construct
SEQUENCE: 42
TINSGGGSTS YAYSVKG                                                       17

SEQ ID NO: 43             moltype = AA  length = 17
```

```
                        -continued

FEATURE                 Location/Qualifiers
REGION                  1..17
                        note = Generated by phage peptide display
source                  1..17
                        mol_type = protein
                        organism = synthetic construct
SEQUENCE: 43
TINIGGGSTS YADSVKG                                                  17

SEQ ID NO: 44           moltype = AA  length = 17
FEATURE                 Location/Qualifiers
REGION                  1..17
                        note = Generated by phage peptide display
source                  1..17
                        mol_type = protein
                        organism = synthetic construct
SEQUENCE: 44
TINGGGGITS YADSVKG                                                  17

SEQ ID NO: 45           moltype = AA  length = 17
FEATURE                 Location/Qualifiers
REGION                  1..17
                        note = Generated by phage peptide display
source                  1..17
                        mol_type = protein
                        organism = synthetic construct
SEQUENCE: 45
TINIAGGITS YADSVKG                                                  17

SEQ ID NO: 46           moltype = AA  length = 17
FEATURE                 Location/Qualifiers
REGION                  1..17
                        note = Generated by phage peptide display
source                  1..17
                        mol_type = protein
                        organism = synthetic construct
SEQUENCE: 46
TINMGGGTTS YADSVKG                                                  17

SEQ ID NO: 47           moltype = AA  length = 17
FEATURE                 Location/Qualifiers
REGION                  1..17
                        note = Generated by phage peptide display
source                  1..17
                        mol_type = protein
                        organism = synthetic construct
SEQUENCE: 47
TITSAGGSIS YVNSVKG                                                  17

SEQ ID NO: 48           moltype = AA  length = 17
FEATURE                 Location/Qualifiers
REGION                  1..17
                        note = Generated by phage peptide display
source                  1..17
                        mol_type = protein
                        organism = synthetic construct
SEQUENCE: 48
AINSDGDKTS YADSVKG                                                  17

SEQ ID NO: 49           moltype = AA  length = 17
FEATURE                 Location/Qualifiers
REGION                  1..17
                        note = Generated by phage peptide display
source                  1..17
                        mol_type = protein
                        organism = synthetic construct
SEQUENCE: 49
TITGASGDTK YADSVKG                                                  17

SEQ ID NO: 50           moltype = AA  length = 16
FEATURE                 Location/Qualifiers
REGION                  1..16
                        note = Generated by phage peptide display
source                  1..16
                        mol_type = protein
                        organism = synthetic construct
SEQUENCE: 50
TVTSSGTAEY ADSVKG                                                   16
```

```
SEQ ID NO: 51              moltype = AA  length = 17
FEATURE                    Location/Qualifiers
REGION                     1..17
                           note = Generated by phage peptide display
source                     1..17
                           mol_type = protein
                           organism = synthetic construct
SEQUENCE: 51
CITSSDTSAY YADSAKG                                                        17

SEQ ID NO: 52              moltype = AA  length = 17
FEATURE                    Location/Qualifiers
REGION                     1..17
                           note = Generated by phage peptide display
source                     1..17
                           mol_type = protein
                           organism = synthetic construct
SEQUENCE: 52
WIVGNDGRTY YIDSVKG                                                        17

SEQ ID NO: 53              moltype = AA  length = 16
FEATURE                    Location/Qualifiers
REGION                     1..16
                           note = Generated by phage peptide display
source                     1..16
                           mol_type = protein
                           organism = synthetic construct
SEQUENCE: 53
VMAPDYGVHY FGSLEG                                                         16

SEQ ID NO: 54              moltype = AA  length = 14
FEATURE                    Location/Qualifiers
REGION                     1..14
                           note = Generated by phage peptide display
source                     1..14
                           mol_type = protein
                           organism = synthetic construct
SEQUENCE: 54
GGGMYGPDLY GMTY                                                           14

SEQ ID NO: 55              moltype = AA  length = 17
FEATURE                    Location/Qualifiers
REGION                     1..17
                           note = Generated by phage peptide display
source                     1..17
                           mol_type = protein
                           organism = synthetic construct
SEQUENCE: 55
GGGSRWYGRT TASWYDY                                                        17

SEQ ID NO: 56              moltype = AA  length = 11
FEATURE                    Location/Qualifiers
REGION                     1..11
                           note = Generated by phage peptide display
source                     1..11
                           mol_type = protein
                           organism = synthetic construct
SEQUENCE: 56
PAYGLRPPYN Y                                                              11

SEQ ID NO: 57              moltype = AA  length = 17
FEATURE                    Location/Qualifiers
REGION                     1..17
                           note = Generated by phage peptide display
source                     1..17
                           mol_type = protein
                           organism = synthetic construct
SEQUENCE: 57
GRSSWFAPWL TPYEYDY                                                        17

SEQ ID NO: 58              moltype = AA  length = 5
FEATURE                    Location/Qualifiers
REGION                     1..5
                           note = Generated by phage peptide display
source                     1..5
                           mol_type = protein
                           organism = synthetic construct
SEQUENCE: 58
GVYDY                                                                      5
```

```
SEQ ID NO: 59          moltype = AA   length = 7
FEATURE                Location/Qualifiers
REGION                 1..7
                       note = Generated by phage peptide display
source                 1..7
                       mol_type = protein
                       organism = synthetic construct
SEQUENCE: 59
DWGWRNY                                                                  7

SEQ ID NO: 60          moltype = AA   length = 12
FEATURE                Location/Qualifiers
REGION                 1..12
                       note = Generated by phage peptide display
source                 1..12
                       mol_type = protein
                       organism = synthetic construct
SEQUENCE: 60
EIYDRRWYRN DY                                                           12

SEQ ID NO: 61          moltype = AA   length = 7
FEATURE                Location/Qualifiers
REGION                 1..7
                       note = Generated by phage peptide display
source                 1..7
                       mol_type = protein
                       organism = synthetic construct
SEQUENCE: 61
YLGSRDY                                                                  7

SEQ ID NO: 62          moltype = AA   length = 8
FEATURE                Location/Qualifiers
REGION                 1..8
                       note = Generated by phage peptide display
source                 1..8
                       mol_type = protein
                       organism = synthetic construct
SEQUENCE: 62
YDGRRPPY                                                                 8

SEQ ID NO: 63          moltype = AA   length = 8
FEATURE                Location/Qualifiers
REGION                 1..8
                       note = Generated by phage peptide display
source                 1..8
                       mol_type = protein
                       organism = synthetic construct
SEQUENCE: 63
YDGRRRTY                                                                 8

SEQ ID NO: 64          moltype = AA   length = 8
FEATURE                Location/Qualifiers
REGION                 1..8
                       note = Generated by phage peptide display
source                 1..8
                       mol_type = protein
                       organism = synthetic construct
SEQUENCE: 64
YDGRRSPY                                                                 8

SEQ ID NO: 65          moltype = AA   length = 7
FEATURE                Location/Qualifiers
REGION                 1..7
                       note = Generated by phage peptide display
source                 1..7
                       mol_type = protein
                       organism = synthetic construct
SEQUENCE: 65
LVGAKDY                                                                  7

SEQ ID NO: 66          moltype = AA   length = 4
FEATURE                Location/Qualifiers
REGION                 1..4
                       note = Generated by phage peptide display
source                 1..4
                       mol_type = protein
                       organism = synthetic construct
SEQUENCE: 66
```

```
                                            -continued
NGIY                                                                          4

SEQ ID NO: 67           moltype = AA  length = 6
FEATURE                 Location/Qualifiers
REGION                  1..6
                        note = Generated by phage peptide display
source                  1..6
                        mol_type = protein
                        organism = synthetic construct
SEQUENCE: 67
TASHIP                                                                        6

SEQ ID NO: 68           moltype = AA  length = 8
FEATURE                 Location/Qualifiers
REGION                  1..8
                        note = Generated by phage peptide display
source                  1..8
                        mol_type = protein
                        organism = synthetic construct
SEQUENCE: 68
TARDSRDS                                                                      8

SEQ ID NO: 69           moltype = AA  length = 8
FEATURE                 Location/Qualifiers
REGION                  1..8
                        note = Generated by phage peptide display
source                  1..8
                        mol_type = protein
                        organism = synthetic construct
SEQUENCE: 69
TAANWSAQ                                                                      8

SEQ ID NO: 70           moltype = AA  length = 8
FEATURE                 Location/Qualifiers
REGION                  1..8
                        note = Generated by phage peptide display
source                  1..8
                        mol_type = protein
                        organism = synthetic construct
SEQUENCE: 70
TAGNWSAQ                                                                      8

SEQ ID NO: 71           moltype = AA  length = 6
FEATURE                 Location/Qualifiers
REGION                  1..6
                        note = Generated by phage peptide display
source                  1..6
                        mol_type = protein
                        organism = synthetic construct
SEQUENCE: 71
LVNLAQ                                                                        6

SEQ ID NO: 72           moltype = AA  length = 21
FEATURE                 Location/Qualifiers
REGION                  1..21
                        note = Generated by phage peptide display
source                  1..21
                        mol_type = protein
                        organism = synthetic construct
SEQUENCE: 72
RDLYCSGSMC KDVLGGARYD F                                                      21

SEQ ID NO: 73           moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 73
YLTYDSGSVK GVNY                                                              14

SEQ ID NO: 74           moltype = AA  length = 14
FEATURE                 Location/Qualifiers
REGION                  1..14
                        note = Generated by phage peptide display
source                  1..14
                        mol_type = protein
                        organism = synthetic construct
```

```
SEQUENCE: 74
CLTYDSGSVK GVNY                                                              14

SEQ ID NO: 75           moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 75
YLTYDSGSAK GVNY                                                              14

SEQ ID NO: 76           moltype = AA  length = 16
FEATURE                 Location/Qualifiers
REGION                  1..16
                        note = Generated by phage peptide display
source                  1..16
                        mol_type = protein
                        organism = synthetic construct
SEQUENCE: 76
HLRYGDYVRG PPEYNY                                                            16

SEQ ID NO: 77           moltype = AA  length = 20
FEATURE                 Location/Qualifiers
REGION                  1..20
                        note = Generated by phage peptide display
source                  1..20
                        mol_type = protein
                        organism = synthetic construct
SEQUENCE: 77
GYYFRDYSDS YYYTGTGMKV                                                        20

SEQ ID NO: 78           moltype = AA  length = 20
FEATURE                 Location/Qualifiers
REGION                  1..20
                        note = Generated by phage peptide display
source                  1..20
                        mol_type = protein
                        organism = synthetic construct
SEQUENCE: 78
KFWPRYYSGR PPVGRDGYDY                                                        20

SEQ ID NO: 79           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 79
QVQLQESGGG LVQAGGSLRL SCAAS                                                  25

SEQ ID NO: 80           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 80
QVQLQESGGG LVQAGGSLRL SCVAS                                                  25

SEQ ID NO: 81           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 81
QVQLQESGGG LVQAGGSLRL SCAVS                                                  25

SEQ ID NO: 82           moltype = AA  length = 25
FEATURE                 Location/Qualifiers
REGION                  1..25
                        note = Generated by phage peptide display
source                  1..25
                        mol_type = protein
```

```
                        organism = synthetic construct
SEQUENCE: 82
QVQLQESGGG LVQAGGSLKL SCTAS                                              25

SEQ ID NO: 83           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 83
QVQLQESGGG LVQAGDSRIL SCTAS                                              25

SEQ ID NO: 84           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 84
QVQLQESGGG LVQAGGSLRL ACAAS                                              25

SEQ ID NO: 85           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 85
QVQLQESGGG LVQPGGSLRL SCAVS                                              25

SEQ ID NO: 86           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 86
QVQLQESGGG LVRPGGSLRL SCAVS                                              25

SEQ ID NO: 87           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 87
QVQLQESGGG SVQPGGSLSL SCSAS                                              25

SEQ ID NO: 88           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 88
QVQLQESGGG LVQPGGSLSL SCSAS                                              25

SEQ ID NO: 89           moltype = AA  length = 25
FEATURE                 Location/Qualifiers
REGION                  1..25
                        note = Generated by phage peptide display
source                  1..25
                        mol_type = protein
                        organism = synthetic construct
SEQUENCE: 89
QVQLQESGGG LVQPGGSLRL SCSAS                                              25

SEQ ID NO: 90           moltype = AA  length = 25
FEATURE                 Location/Qualifiers
REGION                  1..25
                        note = Generated by phage peptide display
source                  1..25
```

```
                            mol_type = protein
                            organism = synthetic construct
SEQUENCE: 90
QVQLQESGGG LVQPGGSLRL SCAAS                                           25

SEQ ID NO: 91               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 91
QVQLQESGGG LVRPGGSLRL SCEAS                                           25

SEQ ID NO: 92               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 92
QVQLQESGGG LVQSGDSLRL SCAAS                                           25

SEQ ID NO: 93               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 93
QVQLQESGGG MVEPGGSLRL SCAAS                                           25

SEQ ID NO: 94               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 94
QVQLQESGGG LVEPGGSLRL SCAAS                                           25

SEQ ID NO: 95               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 95
QVQLQESGGG LVQSGESLRL SCAAS                                           25

SEQ ID NO: 96               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 96
QVQLQESGGG LVQPGGSLKL SCAAS                                           25

SEQ ID NO: 97               moltype = AA   length = 25
FEATURE                     Location/Qualifiers
REGION                      1..25
                            note = Generated by phage peptide display
source                      1..25
                            mol_type = protein
                            organism = synthetic construct
SEQUENCE: 97
QVQLQESGGG LVRPGGSLKL SCAAS                                           25

SEQ ID NO: 98               moltype = AA   length = 25
FEATURE                     Location/Qualifiers
REGION                      1..25
                            note = Generated by phage peptide display
```

```
                              source          1..25
                                              mol_type = protein
                                              organism = synthetic construct
SEQUENCE: 98
QVQLQESGGG SVQPGGSLKL SCAAS                                                     25

SEQ ID NO: 99         moltype = AA   length = 25
FEATURE               Location/Qualifiers
REGION                1..25
                      note = Generated by phage peptide display
source                1..25
                      mol_type = protein
                      organism = synthetic construct
SEQUENCE: 99
QVQLQESGGG FVQPGGSLKL SCAAS                                                     25

SEQ ID NO: 100        moltype = AA   length = 25
FEATURE               Location/Qualifiers
REGION                1..25
                      note = Generated by phage peptide display
source                1..25
                      mol_type = protein
                      organism = synthetic construct
SEQUENCE: 100
QVQLQESGGG LVQPGGSLGL SCAAS                                                     25

SEQ ID NO: 101        moltype = AA   length = 25
FEATURE               Location/Qualifiers
REGION                1..25
                      note = Generated by phage peptide display
source                1..25
                      mol_type = protein
                      organism = synthetic construct
SEQUENCE: 101
QVQLQESGGG LVQPGGSTRL SCAAS                                                     25

SEQ ID NO: 102        moltype = AA   length = 25
FEATURE               Location/Qualifiers
REGION                1..25
                      note = Generated by phage peptide display
source                1..25
                      mol_type = protein
                      organism = synthetic construct
SEQUENCE: 102
QVQLQESGGG LVQPGGSLIL SCTIS                                                     25

SEQ ID NO: 103        moltype = AA   length = 14
FEATURE               Location/Qualifiers
REGION                1..14
                      note = Generated by phage peptide display
source                1..14
                      mol_type = protein
                      organism = synthetic construct
SEQUENCE: 103
WFRQAPGKER EFVA                                                                 14

SEQ ID NO: 104        moltype = AA   length = 14
FEATURE               Location/Qualifiers
REGION                1..14
                      note = Generated by phage peptide display
source                1..14
                      mol_type = protein
                      organism = synthetic construct
SEQUENCE: 104
WFRQAPGEER VFVA                                                                 14

SEQ ID NO: 105        moltype = AA   length = 14
FEATURE               Location/Qualifiers
REGION                1..14
                      note = Generated by phage peptide display
source                1..14
                      mol_type = protein
                      organism = synthetic construct
SEQUENCE: 105
WFRQGPGEER QFLA                                                                 14

SEQ ID NO: 106        moltype = AA   length = 14
FEATURE               Location/Qualifiers
REGION                1..14
```

```
                    note = Generated by phage peptide display
source              1..14
                    mol_type = protein
                    organism = synthetic construct
SEQUENCE: 106
WFRRAPGKER EFVG                                                             14

SEQ ID NO: 107      moltype = AA  length = 14
FEATURE             Location/Qualifiers
REGION              1..14
                    note = Generated by phage peptide display
source              1..14
                    mol_type = protein
                    organism = synthetic construct
SEQUENCE: 107
WFRQAPGKER EEIS                                                             14

SEQ ID NO: 108      moltype = AA  length = 14
FEATURE             Location/Qualifiers
REGION              1..14
                    note = Generated by phage peptide display
source              1..14
                    mol_type = protein
                    organism = synthetic construct
SEQUENCE: 108
WYRQAPGKQR EWVA                                                             14

SEQ ID NO: 109      moltype = AA  length = 14
FEATURE             Location/Qualifiers
REGION              1..14
                    note = Generated by phage peptide display
source              1..14
                    mol_type = protein
                    organism = synthetic construct
SEQUENCE: 109
WYRQAPGKQR EWVT                                                             14

SEQ ID NO: 110      moltype = AA  length = 14
FEATURE             Location/Qualifiers
REGION              1..14
                    note = Generated by phage peptide display
source              1..14
                    mol_type = protein
                    organism = synthetic construct
SEQUENCE: 110
WYRQTPGKTR DWVA                                                             14

SEQ ID NO: 111      moltype = AA  length = 14
FEATURE             Location/Qualifiers
REGION              1..14
                    note = Generated by phage peptide display
source              1..14
                    mol_type = protein
                    organism = synthetic construct
SEQUENCE: 111
WYRQAPGKER EWVA                                                             14

SEQ ID NO: 112      moltype = AA  length = 14
FEATURE             Location/Qualifiers
REGION              1..14
                    note = Generated by phage peptide display
source              1..14
                    mol_type = protein
                    organism = synthetic construct
SEQUENCE: 112
WVRQAPGKGL EWVS                                                             14

SEQ ID NO: 113      moltype = AA  length = 14
FEATURE             Location/Qualifiers
REGION              1..14
                    note = Generated by phage peptide display
source              1..14
                    mol_type = protein
                    organism = synthetic construct
SEQUENCE: 113
WVRLAPGKGL EWVS                                                             14

SEQ ID NO: 114      moltype = AA  length = 14
FEATURE             Location/Qualifiers
```

```
REGION                  1..14
                        note = Generated by phage peptide display
source                  1..14
                        mol_type = protein
                        organism = synthetic construct
SEQUENCE: 114
WIRQPPGKAR EVVA                                                              14

SEQ ID NO: 115          moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 115
WVRQAPGKGL ERVS                                                              14

SEQ ID NO: 116          moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 116
WYRQVPGEER KMVA                                                              14

SEQ ID NO: 117          moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 117
WYRQAPGRQR ELVA                                                              14

SEQ ID NO: 118          moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 118
WFRQAPGKER EAVS                                                              14

SEQ ID NO: 119          moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 119
WFRQAPGKEH EGVS                                                              14

SEQ ID NO: 120          moltype = AA  length = 14
FEATURE                 Location/Qualifiers
REGION                  1..14
                        note = Generated by phage peptide display
source                  1..14
                        mol_type = protein
                        organism = synthetic construct
SEQUENCE: 120
WSRQGPGKSL EIIA                                                              14

SEQ ID NO: 121          moltype = AA  length = 32
FEATURE                 Location/Qualifiers
REGION                  1..32
                        note = Generated by phage peptide display
source                  1..32
                        mol_type = protein
                        organism = synthetic construct
SEQUENCE: 121
RFTISRDNAK NTVYLQMNNL APEDTATYYC KA                                          32

SEQ ID NO: 122          moltype = AA  length = 32
```

```
FEATURE              Location/Qualifiers
REGION               1..32
                     note = Generated by phage peptide display
source               1..32
                     mol_type = protein
                     organism = synthetic construct
SEQUENCE: 122
RFTISRDDAK NTVYLQMNSL KPEDTAVYYC AA                                      32

SEQ ID NO: 123       moltype = AA  length = 32
FEATURE              Location/Qualifiers
REGION               1..32
                     note = Generated by phage peptide display
source               1..32
                     mol_type = protein
                     organism = synthetic construct
SEQUENCE: 123
RFTISRDHAK NVMYLQMNGL KPEDTGVYVC AR                                      32

SEQ ID NO: 124       moltype = AA  length = 32
FEATURE              Location/Qualifiers
REGION               1..32
                     note = Generated by phage peptide display
source               1..32
                     mol_type = protein
                     organism = synthetic construct
SEQUENCE: 124
RFTISRDNAK NTGYLQMNNL KPEDTGVYYC AA                                      32

SEQ ID NO: 125       moltype = AA  length = 32
FEATURE              Location/Qualifiers
REGION               1..32
                     note = Generated by phage peptide display
source               1..32
                     mol_type = protein
                     organism = synthetic construct
SEQUENCE: 125
RFTISRDLAK NTLYLQMNSL KPEDTAVYYC AR                                      32

SEQ ID NO: 126       moltype = AA  length = 32
FEATURE              Location/Qualifiers
REGION               1..32
                     note = Generated by phage peptide display
source               1..32
                     mol_type = protein
                     organism = synthetic construct
SEQUENCE: 126
RFTISRDNAK NTVYLQMNSL KPEDTAVYYC NA                                      32

SEQ ID NO: 127       moltype = AA  length = 32
FEATURE              Location/Qualifiers
REGION               1..32
                     note = Generated by phage peptide display
source               1..32
                     mol_type = protein
                     organism = synthetic construct
SEQUENCE: 127
RFTISRDNVK NTVYLQMNSL KLEDTAVYYC YA                                      32

SEQ ID NO: 128       moltype = AA  length = 32
FEATURE              Location/Qualifiers
REGION               1..32
                     note = Generated by phage peptide display
source               1..32
                     mol_type = protein
                     organism = synthetic construct
SEQUENCE: 128
RFTISRDNAK NTVYLQMNSL TPEDTAVYYC NT                                      32

SEQ ID NO: 129       moltype = AA  length = 32
FEATURE              Location/Qualifiers
REGION               1..32
                     note = Generated by phage peptide display
source               1..32
                     mol_type = protein
                     organism = synthetic construct
SEQUENCE: 129
RFTVSRDNAK NTLYLQMNSL KPEDTAVYYC NS                                      32
```

```
SEQ ID NO: 130           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 130
RFTVSRDNAK NTVHLQMNSL KPEDTAVYYC HA                                    32

SEQ ID NO: 131           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 131
RFTVSRDNAK NTVHLQMNSL KPEDAAVYYC HA                                    32

SEQ ID NO: 132           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 132
RFTTSRDNAR NTVYLQMNSL KPEDTAVYYC NT                                    32

SEQ ID NO: 133           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 133
RFTISRDNAK NALYLQMNGL KPEDTAVYYC NA                                    32

SEQ ID NO: 134           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 134
RFTISRDNAK NTLYLQMNSL KPEDTAVYYC AK                                    32

SEQ ID NO: 135           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 135
RFTISRDNAK NTMYLQMNSL KPEDTAVYYC AQ                                    32

SEQ ID NO: 136           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 136
RFTISRHNAK NTLYLQMNSL KPEDTAVYYC AK                                    32

SEQ ID NO: 137           moltype = AA  length = 32
FEATURE                  Location/Qualifiers
REGION                   1..32
                         note = Generated by phage peptide display
source                   1..32
                         mol_type = protein
                         organism = synthetic construct
SEQUENCE: 137
RFTISRDNAK NTLYLQMNML KPEDTAVYYC AR                                    32
```

```
SEQ ID NO: 138            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 138
RFTISRDNAR NTLYLQMSNL KPEDTAVYYC AD                                        32

SEQ ID NO: 139            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 139
RFTISRDNAR NTLYLQMNNL KPEDTAVYYC AD                                        32

SEQ ID NO: 140            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 140
RFTISRDNAK NTVTLQMNSL KPGDAAVYYC HA                                        32

SEQ ID NO: 141            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 141
RFTISRDNAK NTVTLQMNSL KPGDTAVYYC HA                                        32

SEQ ID NO: 142            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 142
RSTISRDNAK NTVTLQMNSL KPGDTAVYYC HA                                        32

SEQ ID NO: 143            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 143
RFTISRDNAK NTVYLQMNSL RPEDTGVYYC NA                                        32

SEQ ID NO: 144            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 144
RFTISRDNAK NTMYLQMNNL KPEDTAVYYC AA                                        32

SEQ ID NO: 145            moltype = AA   length = 32
FEATURE                   Location/Qualifiers
REGION                    1..32
                          note = Generated by phage peptide display
source                    1..32
                          mol_type = protein
                          organism = synthetic construct
SEQUENCE: 145
```

RFTISRDNAK NTVYLEMNSL KPEDTAVYYC AA                             32

SEQ ID NO: 146          moltype = AA   length = 32
FEATURE                 Location/Qualifiers
REGION                  1..32
                        note = Generated by phage peptide display
source                  1..32
                        mol_type = protein
                        organism = synthetic construct
SEQUENCE: 146
RVAVRGDVVK NTVYLQVNAL KPEDTAIYWC SM                             32

SEQ ID NO: 147          moltype = AA   length = 11
FEATURE                 Location/Qualifiers
REGION                  1..11
                        note = Generated by phage peptide display
source                  1..11
                        mol_type = protein
                        organism = synthetic construct
SEQUENCE: 147
WGKGTQVTVS S                                                    11

SEQ ID NO: 148          moltype = AA   length = 11
FEATURE                 Location/Qualifiers
REGION                  1..11
                        note = Generated by phage peptide display
source                  1..11
                        mol_type = protein
                        organism = synthetic construct
SEQUENCE: 148
WGQGTQVTVS S                                                    11

SEQ ID NO: 149          moltype = AA   length = 11
FEATURE                 Location/Qualifiers
REGION                  1..11
                        note = Generated by phage peptide display
source                  1..11
                        mol_type = protein
                        organism = synthetic construct
SEQUENCE: 149
RGQGTQVTVS S                                                    11

SEQ ID NO: 150          moltype = AA   length = 11
FEATURE                 Location/Qualifiers
REGION                  1..11
                        note = Generated by phage peptide display
source                  1..11
                        mol_type = protein
                        organism = synthetic construct
SEQUENCE: 150
WGRGTQVTVS S                                                    11

SEQ ID NO: 151          moltype = AA   length = 11
FEATURE                 Location/Qualifiers
REGION                  1..11
                        note = Generated by phage peptide display
source                  1..11
                        mol_type = protein
                        organism = synthetic construct
SEQUENCE: 151
LSQGTQVTVS S                                                    11

SEQ ID NO: 152          moltype = AA   length = 11
FEATURE                 Location/Qualifiers
REGION                  1..11
                        note = Generated by phage peptide display
source                  1..11
                        mol_type = protein
                        organism = synthetic construct
SEQUENCE: 152
TGQGTQVTVS S                                                    11

SEQ ID NO: 153          moltype = AA   length = 11
FEATURE                 Location/Qualifiers
REGION                  1..11
                        note = Generated by phage peptide display
source                  1..11
                        mol_type = protein
                        organism = synthetic construct

```
SEQUENCE: 153
RGLGTQVTVS S                                                                  11

SEQ ID NO: 154          moltype = AA  length = 123
FEATURE                 Location/Qualifiers
REGION                  1..123
                        note = Generated by phage peptide display
source                  1..123
                        mol_type = protein
                        organism = synthetic construct
SEQUENCE: 154
QVQLQESGGG LVQAGGSLRL SCAASGRTWR AYYMGWFRQA PGKEREFVAV MSRSGGTTSY    60
ADSVKGRFTI SRDNAKNTVY LQMNNLAPED TATYYCKAGG GMYGPDLYGM TYWGKGTQVT   120
VSS                                                                          123

SEQ ID NO: 155          moltype = AA  length = 126
FEATURE                 Location/Qualifiers
REGION                  1..126
                        note = Generated by phage peptide display
source                  1..126
                        mol_type = protein
                        organism = synthetic construct
SEQUENCE: 155
QVQLQESGGG LVQAGGSLRL SCVASGRAFS NYAMAWFRQA PGKEREFVAA NWRSGGLTDY    60
ADSVKGRFTI SRDDAKNTVY LQMNSLKPED TAVYYCAAGG GSRWYGRTTA SWYDYWGQGT   120
QVTVSS                                                                       126

SEQ ID NO: 156          moltype = AA  length = 120
FEATURE                 Location/Qualifiers
REGION                  1..120
                        note = Generated by phage peptide display
source                  1..120
                        mol_type = protein
                        organism = synthetic construct
SEQUENCE: 156
QVQLQESGGG LVQAGGSLRL SCAVSGRTFS RYAMGWFRQA PGKEREFVAA ISWSGSSTYY    60
ADSVKGRFTI SRDHAKNVMY LQMNGLKPED TGVYVCARPA YGLRPPYNYR GQGTQVTVSS   120

SEQ ID NO: 157          moltype = AA  length = 126
FEATURE                 Location/Qualifiers
REGION                  1..126
                        note = Generated by phage peptide display
source                  1..126
                        mol_type = protein
                        organism = synthetic construct
SEQUENCE: 157
QVQLQESGGG LVQAGGSLKL SCTASQRTFS RYSLGWFRQA PGEERVFVAA TTWSGISSDY    60
ADSVKGRFTI SRDNAKNTGY LQMNNLKPED TGVYYCAAGR SSWFAPWLTP YEYDYWGRGT   120
QVTVSS                                                                       126

SEQ ID NO: 158          moltype = AA  length = 114
FEATURE                 Location/Qualifiers
REGION                  1..114
                        note = Generated by phage peptide display
source                  1..114
                        mol_type = protein
                        organism = synthetic construct
SEQUENCE: 158
QVQLQESGGG LVQAGGSLRL SCAASGRTFS SHAMAWFRQG PGEERQFLAA IRWNGDNIHY    60
SDSAKGRFTI SRDLAKNTLY LQMNSLKPED TAVYYCARGV YDYWGQGTQV TVSS          114

SEQ ID NO: 159          moltype = AA  length = 119
FEATURE                 Location/Qualifiers
REGION                  1..119
                        note = Generated by phage peptide display
source                  1..119
                        mol_type = protein
                        organism = synthetic construct
SEQUENCE: 159
QVQLQESGGG LVQAGDSRIL SCTASGRTFG RPFRYTMGWF RRAPGKEREF VGGITRSGNN    60
IYYSDSVKGR FTISRDNAKN TVYLQMNSLK PEDTAVYYCN ADWGWRNYWG QGTQVTVSS    119

SEQ ID NO: 160          moltype = AA  length = 121
FEATURE                 Location/Qualifiers
REGION                  1..121
                        note = Generated by phage peptide display
source                  1..121
                        mol_type = protein
                        organism = synthetic construct
```

```
SEQUENCE: 160
QVQLQESGGG LVQAGGSLRL ACAASGETVD DLAIGWFRQA PGKEREEISC ISGSDGSTYY   60
ADSLSGRFTI SRDNVKNTVY LQMNSLKLED TAVYYCYAEI YDRRWYRNDY WGQGTQVTVS  120
S                                                                 121

SEQ ID NO: 161          moltype = DNA  length = 417
FEATURE                 Location/Qualifiers
misc_feature            1..417
                        note = Generated by phage peptide display
source                  1..417
                        mol_type = other DNA
                        organism = synthetic construct
SEQUENCE: 161
caggtgcagc tgcaggagtc tgggggagga ttggtgcagg ctgggggctc tctgagactc   60
tcctgtgcag cctctggacg cacctggaga gcctattaca tgggctggtt ccgccaggct  120
ccagggaagg agcgtgagtt tgtagcagtt atgagtcgga gcggtggcac acatcctat   180
gcggactccg tgaagggccg attcaccatc tccagagaca cgccaagaa cacggtgtat   240
ctacaaatga acaacctggc acctgaggac acggccacgt attattgtaa ggcggggggc  300
ggaatgtacg ggccggacct gtatggtatg acatactggg gcaaagggac ccaggtcacc  360
gtctccagcg ccgctaccc gtacgacgtt cggactacg gttccggccg agcatag      417

SEQ ID NO: 162          moltype = DNA  length = 426
FEATURE                 Location/Qualifiers
misc_feature            1..426
                        note = Generated by phage peptide display
source                  1..426
                        mol_type = other DNA
                        organism = synthetic construct
SEQUENCE: 162
caggtgcagc tgcaggagtc tggaggagga ttggtacagg ctgggggctc tctgagactc   60
tcctgtgtag cctctggacg cgccttcagt aattatgcga tggcctggtt ccgccaggct  120
ccagggaagg agcgtgagtt tgtagcagct aattggcgga gtggtggtct tacagactat  180
gcagactccg tgaagggccg attcaccatc tccagagacg acgccaagaa cacggtgtat  240
ctgcaaatga acagcctgaa acctgaggac acggccgttt attactgtgc cgccggggc   300
ggtagtcgct ggtacgggcg aacaaccgca agttggtatg actactgggg ccaggggacc  360
caggtcaccg tctccagcgg ccgctacccg tacgacgttc ggactacgg ttccggcga   420
gcatag                                                            426

SEQ ID NO: 163          moltype = DNA  length = 408
FEATURE                 Location/Qualifiers
misc_feature            1..408
                        note = Generated by phage peptide display
source                  1..408
                        mol_type = other DNA
                        organism = synthetic construct
SEQUENCE: 163
caggtgcagc tgcaggagtc tgggggagga ttggtgcagg ctgggggctc tctgagactc   60
tcctgtgcag tctctggacg caccttcagt agatatgcca tgggctggtt ccgccaggct  120
ccagggaagg agcgtgagtt tgtagcagct attagctgga gtggtagtag cacatattat  180
gcagactccg tgaagggccg attcaccatc tccagagacc acgccaagaa cgtgatgtat  240
ctgcaaatga acggcctgaa acctgaggac acgggtgtaa atgtctgtgc aagaccagcg  300
tacggactcc gcccccgta taattaccgg ggcaggggga cccaggtcac cgtctccagc  360
ggccgctacc cgtacgacgt tccggactac ggttccggcc gagcatag              408

SEQ ID NO: 164          moltype = DNA  length = 426
FEATURE                 Location/Qualifiers
misc_feature            1..426
                        note = Generated by phage peptide display
source                  1..426
                        mol_type = other DNA
                        organism = synthetic construct
SEQUENCE: 164
caggtgcagc tgcaggagtc tgggggagga ttggtgcagg ctgggggctt tctgaaactc   60
tcctgcacag cctctcaacg caccttcagt cgctatatgg tgggctggtt ccgccaggct  120
ccaggtgagg agcgtgtttt tgtagcgcgt actacatgga gtggtataag cagtgactat  180
gcagactccg tgaagggccg attcaccatc tccagagaca cgccaagaa cacggggtat   240
ctgcaaatga acaatttaaa acctgaggac acggcgtttt attactgtgc agcaggacgt  300
agtagctggt tcgccccctg gttgaccccc tatgagtatg attattgggg ccgggggacc  360
caggtcaccg tctccagcgg ccgctacccg tacgacgttc ggactacgg ttccggccga   420
gcatag                                                            426

SEQ ID NO: 165          moltype = DNA  length = 390
FEATURE                 Location/Qualifiers
misc_feature            1..390
                        note = Generated by phage peptide display
source                  1..390
                        mol_type = other DNA
                        organism = synthetic construct
SEQUENCE: 165
```

```
caggtgcagc tgcaggagtc tggggggagga ttggtgcagg ctggggggctc tctgagactc    60
tcctgtgcag cctctggacg caccttcagt agccatgcca tggcctggtt ccgccaggtt   120
ccaggagagg agcgtcagtt tctagcagct attagatgga atggtgataa catacactat   180
tcagactccg cgaagggccg attcaccatc tccagagacc tcgccaagaa cacgctctat   240
ctgcaaatga acagcctgaa acctgaggac acggccgtgt attactgtgc aaggggggtg   300
tatgactact ggggccaggg gacccaggtc accgtctcca gcggccgcta cccgtacgac   360
gttccggact acggttccgg ccgagcatag                                     390
```

```
SEQ ID NO: 166        moltype = DNA    length = 405
FEATURE               Location/Qualifiers
misc_feature          1..405
                      note = Generated by phage peptide display
source                1..405
                      mol_type = other DNA
                      organism = synthetic construct
SEQUENCE: 166
caggtgcagc tgcaggagtc tgggggagga ttggtgcagg ctgggggactc tcggatactc    60
tcctgtacag cctctggacg caccttttgga cgccccttca gatataccat gggctggttc   120
cgccgggctc cagggaagga gcgtgagttt gtaggaggta ttacaagaag tggtaataat   180
atatactatt cagactccgt gaagggccga ttcaccatct ccagagacaa cgccaagaac   240
acggtgtatc tccaaatgaa cagcctgaaa cctgaggaca cggccgtgta ttattgtaac   300
gcagattggg ggtggaggaa ctactggggc caggggaccc aggtcaccgt ctccagcggc   360
cgctacccgt acgacgttcc ggactacggt tccggccgag catag                   405
```

```
SEQ ID NO: 167        moltype = DNA    length = 411
FEATURE               Location/Qualifiers
misc_feature          1..411
                      note = Generated by phage peptide display
source                1..411
                      mol_type = other DNA
                      organism = synthetic construct
SEQUENCE: 167
caggtgcagc tgcaggagtc tgggggaggc ttggtgcagg ctgggggggtc tctgagactc    60
gcctgtgcag cctctggaga gactgtcgat gatcttgcca tcggctggtt ccgccaggcc   120
ccagggaagg agcgtgagga gatttcatgt attagtggta gtgatggta cacatactat   180
gcagactccc tgtcgggccg attcaccatc tccaggggaca acgtcaagaa cacggtgtat   240
ctgcaaatga acagcctgaa acttgaggac acggccgtct attactgtta tgcagagatt   300
tacgatagcg ctggtatcg gaacgactac tggggccagg ggaccccaggt caccgtctcc   360
agcggccgct acccgtacga cgttccggac tacggttccg ccgagcata g             411
```

```
SEQ ID NO: 168        moltype = AA    length = 115
FEATURE               Location/Qualifiers
REGION                1..115
                      note = Generated by phage peptide display
source                1..115
                      mol_type = protein
                      organism = synthetic construct
SEQUENCE: 168
QVQLQESGGG LVQAGGSLRL SCAVSGMMYI REAIRWYRQA PGKQREWVAF VSSTGNPRYT    60
DSVKGRFTIS RDNAKNTVYL QMNSLTPEDT AVYYCNTYLG SRDYWGQGTQ VTVSS        115
```

```
SEQ ID NO: 169        moltype = AA    length = 115
FEATURE               Location/Qualifiers
REGION                1..115
                      note = Generated by phage peptide display
source                1..115
                      mol_type = protein
                      organism = synthetic construct
SEQUENCE: 169
QVQLQESGGG LVQPGGSLRL SCAVSGMMYI RYTMRWYRQA PGKQREWVAV VSSTGNPHYA    60
DSVKGRFTIS RDNAKNTVYL QMNSLTPEDT AVYYCNTYLG SRDYWGQGTQ VTVSS        115
```

```
SEQ ID NO: 170        moltype = AA    length = 111
FEATURE               Location/Qualifiers
REGION                1..111
                      note = Generated by phage peptide display
source                1..111
                      mol_type = protein
                      organism = synthetic construct
SEQUENCE: 170
QVQLQESGGG LVRPGGSLRL SCAVSGRAVN RYHMHWYRQA PGKQREWVTF ISVGGTTNYA    60
GSVKGRFTVS RDNAKNTLYL QMNSLKPEDT AVYYCNSAEY WGQGTQVTVS S            111
```

```
SEQ ID NO: 171        moltype = AA    length = 116
FEATURE               Location/Qualifiers
REGION                1..116
                      note = Generated by phage peptide display
source                1..116
                      mol_type = protein
```

```
                        organism = synthetic construct
SEQUENCE: 171
QVQLQESGGG SVQPGGSLSL SCSASGIIFS DYALTWYRQA PGKQREWVAQ ITRSQNINYT    60
GSVKGRFTVS RDNAKNTVHL QMNSLKPEDT AVYYCHAYDG RRPPYWGQGT QVTVSS        116

SEQ ID NO: 172          moltype = AA   length = 116
FEATURE                 Location/Qualifiers
REGION                  1..116
                        note = Generated by phage peptide display
source                  1..116
                        mol_type = protein
                        organism = synthetic construct
SEQUENCE: 172
QVQLQESGGG SVQPGGSLSL SCSASGIIFS DYALTWYRQA PGKQREWVAQ ITRSQNINYT    60
GSVKGRFTVS RDNAKNTVHL QMNSLKPEDT AVYYCHAYDG RRRTYWGQGT QVTVSS        116

SEQ ID NO: 173          moltype = AA   length = 116
FEATURE                 Location/Qualifiers
REGION                  1..116
                        note = Generated by phage peptide display
source                  1..116
                        mol_type = protein
                        organism = synthetic construct
SEQUENCE: 173
QVQLQESGGG LVQPGGSLSL SCSASGIIFS DYALTWYRQA PGKQREWVAQ ITRSQNINYT    60
GSVKGRFTVS RDNAKNTVHL QMNSLKPEDT AVYYCHAYDG RRPPYWGQGT QVTVSS        116

SEQ ID NO: 174          moltype = AA   length = 116
FEATURE                 Location/Qualifiers
REGION                  1..116
                        note = Generated by phage peptide display
source                  1..116
                        mol_type = protein
                        organism = synthetic construct
SEQUENCE: 174
QVQLQESGGG LVQPGGSLSL SCSASGIIFS DYALTWYRQA PGKQREWVAQ ITRRQNINYT    60
GSVKGRFTVS RDNAKNTVHL QMNSLKPEDT AVYYCHAYDG RRSPYWGQGT QVTVSS        116

SEQ ID NO: 175          moltype = AA   length = 116
FEATURE                 Location/Qualifiers
REGION                  1..116
                        note = Generated by phage peptide display
source                  1..116
                        mol_type = protein
                        organism = synthetic construct
SEQUENCE: 175
QVQLQESGGG LVQPGGSLRL SCSASGIIFS DYALTWYRQA PGKQREWVAQ ITRSQNINYT    60
GSVKGRFTVS RDNAKNTVHL QMNSLKPEDA AVYYCHAYDG RRPPYWGQGT QVTVSS        116

SEQ ID NO: 176          moltype = AA   length = 111
FEATURE                 Location/Qualifiers
REGION                  1..111
                        note = Generated by phage peptide display
source                  1..111
                        mol_type = protein
                        organism = synthetic construct
SEQUENCE: 176
QVQLQESGGG LVQPGGSLRL SCAASARIFS IYAMVWYRQA PGKQREWVAA ITTGGTTNYA    60
DSVKGRFTIS RDNAKNTVYL QMNSLKPEDT AVYYCNAPGY WGQGTQVTVS S             111

SEQ ID NO: 177          moltype = AA   length = 115
FEATURE                 Location/Qualifiers
REGION                  1..115
                        note = Generated by phage peptide display
source                  1..115
                        mol_type = protein
                        organism = synthetic construct
SEQUENCE: 177
QVQLQESGGG LVQPGGSLRL SCAASGVIAS ISVLRWYRQT PGKTRDWVAI ITSGGNTRYA    60
DSVKGRFTTS RDNARNTVYL QMNSLKPEDT AVYYCNTLVG AKDYWGQGTQ VTVSS         115

SEQ ID NO: 178          moltype = AA   length = 113
FEATURE                 Location/Qualifiers
REGION                  1..113
                        note = Generated by phage peptide display
source                  1..113
                        mol_type = protein
                        organism = synthetic construct
SEQUENCE: 178
```

```
QVQLQESGGG LVRPGGSLRL SCEASGTTFR SLVMKWYRQA PGKEREWVAF ISSPGDRTRY    60
TEAVKGRFTI SRDNAKNALY LQMNGLKPED TAVYYCNANG IYWGKGTQVT VSS          113

SEQ ID NO: 179            moltype = AA   length = 115
FEATURE                   Location/Qualifiers
REGION                    1..115
                          note = Generated by phage peptide display
source                    1..115
                          mol_type = protein
                          organism = synthetic construct
SEQUENCE: 179
QVQLQESGGG LVQSGDSLRL SCAASGFTFS NYAMSWVRQA PGKGLEWVST INSGGGSTSY    60
AYSVKGRFTI SRDNAKNTLY LQMNSLKPED TAVYYCAKTA SHIPLSQGTQ VTVSS        115

SEQ ID NO: 180            moltype = AA   length = 115
FEATURE                   Location/Qualifiers
REGION                    1..115
                          note = Generated by phage peptide display
source                    1..115
                          mol_type = protein
                          organism = synthetic construct
SEQUENCE: 180
QVQLQESGGG LVQPGGSLRL SCAASGFTFS NYAMSWVRQA PGKGLEWVST INIGGGSTSY    60
ADSVKGRFTI SRDNAKNTLY LQMNSLKPED TAVYYCAKTA SHIPLSQGTQ VTVSS        115

SEQ ID NO: 181            moltype = AA   length = 117
FEATURE                   Location/Qualifiers
REGION                    1..117
                          note = Generated by phage peptide display
source                    1..117
                          mol_type = protein
                          organism = synthetic construct
SEQUENCE: 181
QVQLQESGGG LVQPGGSLRL SCAASGFTFR NYAMSWVRQA PGKGLEWVST INGGGGITSY    60
ADSVKGRFTI SRDNAKNTMY LQMNSLKPED TAVYYCAQTA RDSRDSRGQG TQVTVSS      117

SEQ ID NO: 182            moltype = AA   length = 117
FEATURE                   Location/Qualifiers
REGION                    1..117
                          note = Generated by phage peptide display
source                    1..117
                          mol_type = protein
                          organism = synthetic construct
SEQUENCE: 182
QVQLQESGGG LVQPGGSLRL SCAASGFTFS SYAMSWVRLA PGKGLEWVST INIAGGITSY    60
ADSVKGRFTI SRDNAKNTLY LQMNSLKPED TAVYYCAKTA ANWSAQRGQG TQVTVSS      117

SEQ ID NO: 183            moltype = AA   length = 117
FEATURE                   Location/Qualifiers
REGION                    1..117
                          note = Generated by phage peptide display
source                    1..117
                          mol_type = protein
                          organism = synthetic construct
SEQUENCE: 183
QVQLQESGGG LVQPGGSLRL SCAASGFTFS SYAMSWVRQA PGKGLEWVST INMGGGTTSY    60
ADSVKGRFTI SRHNAKNTLY LQMNSLKPED TAVYYCAKTA GNWSAQRGQG TQVTVSS      117

SEQ ID NO: 184            moltype = AA   length = 115
FEATURE                   Location/Qualifiers
REGION                    1..115
                          note = Generated by phage peptide display
source                    1..115
                          mol_type = protein
                          organism = synthetic construct
SEQUENCE: 184
QVQLQESGGG LVQPGGSLRL SCAASGFTFS TSAMSWIRQP PGKAREVVAT ITSAGGSISY    60
VNSVKGRFTI SRDNAKNTLY LQMNMLKPED TAVYYCARLV NLAQTGQGTQ VTVSS        115

SEQ ID NO: 185            moltype = AA   length = 115
FEATURE                   Location/Qualifiers
REGION                    1..115
                          note = Generated by phage peptide display
source                    1..115
                          mol_type = protein
                          organism = synthetic construct
SEQUENCE: 185
QVQLQESGGG LVQPGGSLRL SCAASGFTFS TNAMSWIRQP PGKAREVVAT ITSAGGSISY    60
VNSVKGRFTI SRDNAKNTLY LQMNMLKPED TAVYYCARLV NLAQTGQGTQ VTVSS        115
```

```
SEQ ID NO: 186            moltype = DNA  length = 393
FEATURE                   Location/Qualifiers
misc_feature              1..393
                          note = Generated by phage peptide display
source                    1..393
                          mol_type = other DNA
                          organism = synthetic construct
SEQUENCE: 186
caggtgcagc tgcaggagtc tgggggaggc ttggtgcagg ctgggggctc tctgagactc    60
tcctgtgcag tttctggaat gatgtacatt agggaggcta tacgctggta ccgccaggct   120
ccagggaagc agcgcgagtg ggtcgccttt gtaagtagta ctggtaatcc acgctataca   180
gactccgtga agggccgatt caccatctcc agagacaacg ccaagaacac ggtgtatctg   240
caaatgaaca gcctgacacc tgaggacacg gccgtctatt actgtaatac atacttgggc   300
tcgagggact actggggcca ggggacccag gtcaccgtct ccagcggccg ctacccgtac   360
gacgttccgg actacggttc cggccgagca tag                                393

SEQ ID NO: 187            moltype = DNA  length = 393
FEATURE                   Location/Qualifiers
misc_feature              1..393
                          note = Generated by phage peptide display
source                    1..393
                          mol_type = other DNA
                          organism = synthetic construct
SEQUENCE: 187
caggtgcagc tgcaggagtc tggaggaggc ttggtgcagc ctggggggtc tctgagactc    60
tcctgtgcag tttctggaat gatgtacatt aggtacacta tgcgctggta ccgccaggct   120
ccagggaagc agcgcgagtg ggtcgccgtt gtaagtagta ctggtaatcc acactatgca   180
gactccgtga agggccgatt caccatctcc agagacaacg ccaagaacac ggtgtatctg   240
caaatgaaca gcctgacacc tgaggacacg gccgtctatt actgtaatac atacttgggc   300
tcgagggact actggggcca ggggacccag gtcaccgtct ccagcggccg ctacccgtac   360
gacgttccgg actacggttc cggccgagca tag                                393

SEQ ID NO: 188            moltype = DNA  length = 381
FEATURE                   Location/Qualifiers
misc_feature              1..381
                          note = Generated by phage peptide display
source                    1..381
                          mol_type = other DNA
                          organism = synthetic construct
SEQUENCE: 188
caggtgcagc tgcaggagtc tggggggaggc ttggtgcggc ctgggggtc tctgagactc    60
tcctgtgcag tctctggaag agccgtcaat aggtatcaca tgcactggta ccgccaggct   120
ccagggaagc agcgcgagtg ggtcacattt attagtgttg gtggtaccac aaactatgca   180
ggctccgtga agggccgatt caccgtctcc cgagacaacg ccaaaaacac gctgtatctg   240
caaatgaaca gcctgaaacc tgaggacacg gccgtctatt actgtaattc agctgaatac   300
tggggccagg ggaccaggt caccgtctcc agcgccgct acccgtacga cgttccggac   360
tacggttccg gccgagcata g                                             381

SEQ ID NO: 189            moltype = DNA  length = 396
FEATURE                   Location/Qualifiers
misc_feature              1..396
                          note = Generated by phage peptide display
source                    1..396
                          mol_type = other DNA
                          organism = synthetic construct
SEQUENCE: 189
caggtgcagc tgcaggagtc tggggaggc tcggtgcagc ctggggggtc tctgagcctc     60
tcctgttcag cctctggaat catcttcagt gactatgccc tgacctggta ccgccaggct   120
ccagggaagc agcgcgagtg ggttgcacag attacgcgaa gtcaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgcccac cctactgggg ccaggggacc caggtcaccg tctccagcgg ccgctacccg   360
tacgacgttc cggactacgg ttccggccga gcatag                             396

SEQ ID NO: 190            moltype = DNA  length = 396
FEATURE                   Location/Qualifiers
misc_feature              1..396
                          note = Generated by phage peptide display
source                    1..396
                          mol_type = other DNA
                          organism = synthetic construct
SEQUENCE: 190
caggtgcagc tgcaggagtc tggggggaggc tcggtgcagc ctggggggtc tctgagcctc    60
tcctgttcag cctctggaat catcttcagt gactatgccc tgacctggta ccgccaggct   120
ccagggaagc agcgcgagtg ggttgcacag attacgcgaa gccaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgccgaa cctactgggg ccaggggacc caggtcaccg tctccagcgg ccgctacccg   360
```
tacgacgttc cggactacgg ttccggccga gcatag 396

SEQ ID NO: 191          moltype = DNA   length = 396
FEATURE                 Location/Qualifiers
misc_feature            1..396
                        note = Generated by phage peptide display
source                  1..396
                        mol_type = other DNA
                        organism = synthetic construct
SEQUENCE: 191
caggtgcagc tgcaggagtc tgggggaggc ttggtgcagc ctgggggtc tctgagcctc    60
tcctgttcag cctctggaat catcttcagt gactatgccc tgacctggta ccgccaggct   120
ccagggaagc agcgcgagtg ggttgcacag attacgcgaa gccaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgcccac cctactgggg ccaggggacc caggtcaccg tctccagcgg ccgctacccg   360
tacgacgttc cggactacgg ttccggccga gcatag                             396

SEQ ID NO: 192          moltype = DNA   length = 396
FEATURE                 Location/Qualifiers
misc_feature            1..396
                        note = Generated by phage peptide display
source                  1..396
                        mol_type = other DNA
                        organism = synthetic construct
SEQUENCE: 192
caggtgcagc tgcaggagtc tgggggaggc ttggtgcagc ctgggggtc tctgagcctc    60
tcctgttcag cctctggaat catcttcagt gactatgccc tgacctggta ccgccaggct   120
ccagggaagc agcgcgagtg ggttgcacag attacgcgaa ggcaaaatat aaattataca   180
ggatccgtga agggccgatt caccgtctcc agagacaacg ccaagaacac agtgcatctg   240
caaatgaaca gcctgaaacc tgaggacacg gccgtctact attgtcatgc atatgacggt   300
cgacgatcac cctactgggg ccaggggacc caggtcaccg tctccagcgg ccgctacccg   360
tacgacgttc cggactacgg ttccggccga gcatag                             396

SEQ ID NO: 193          moltype = DNA   length = 396
FEATURE                 Location/Qualifiers
misc_feature            1..396
                        note = Generated by phage peptide display
source                  1..396
                        mol_type = other DNA
                        organism = synthetic construct
SEQUENCE: 193
caggtgcagc tgcaggagtc tgggggaggc ttggtgcagc ctgggggtc tctgagactc    60
tcctgttcag cctctggaat catcttcagt gactatgccc tgacctggta ccgccaggct   120
ccagggaagc agcgcgagtg ggttgcacag attacgcgaa gtcaaaatat aaattataca   180
ggatccgtga agggccgatt caccgtctcc agagacaacg ccaagaacac agtgcatctg   240
caaatgaaca gcctgaaacc tgaggacgcg gccgtctact attgtcatgc atatgacggt   300
cgacgcccac cctactgggg ccaggggacc caggtcaccg tctccagcgg ccgctacccg   360
tacgacgttc cggactacgg ttccggccga gcatag                             396

SEQ ID NO: 194          moltype = DNA   length = 381
FEATURE                 Location/Qualifiers
misc_feature            1..381
                        note = Generated by phage peptide display
source                  1..381
                        mol_type = other DNA
                        organism = synthetic construct
SEQUENCE: 194
caggtgcagc tgcaggagtc tgggggaggc ttggtgcagc ctgggggtc tctgagactc    60
tcctgtgcag cctctgcccg catcttcagt atctatgcca tggtatggta ccgccaggct   120
ccagggaagc agcgcgagtg ggtcgcagct attactactg gtggtaccac aaactatgca   180
gactccgtga agggccgatt caccatctcc agagacaacg ccaagaacac ggtgtatctg   240
caaatgaaca gcctgaaacc tgaggacacg gccgtctatt actgtaatgc tccgggctac   300
tggggccagg ggacccaggt caccgtctcc agcgccgct accgtacga cgttccggac    360
tacggttccg gccgagcata g                                             381

SEQ ID NO: 195          moltype = DNA   length = 393
FEATURE                 Location/Qualifiers
misc_feature            1..393
                        note = Generated by phage peptide display
source                  1..393
                        mol_type = other DNA
                        organism = synthetic construct
SEQUENCE: 195
caggtgcagc tgcaggagtc tgggggaggc ttggtgcagc ctgggggtc tctgagactc    60
tcctgtgcag cctctggagt catcgccagt atctccgtcc tgcgctggta ccgccaaaca   120
ccaggaaaga gcgcgactg gtcgcaatt attactagtg gtggcaacac acgctatgca   180
gactccgtga agggccgatt caccacctcc agagataacg ccaggaacac ggtgtatctg   240
caaatgaaca gcctgaaacc tgaggacacg gccgtctatt actgtaatac acttgtagga   300

```
gccaaggact actgggggcca ggggacccag gtcaccgtct ccagcggccg ctacccgtac   360
gacgttccgg actacggttc cggccgagca tag                                 393

SEQ ID NO: 196           moltype = DNA   length = 387
FEATURE                  Location/Qualifiers
misc_feature             1..387
                         note = Generated by phage peptide display
source                   1..387
                         mol_type = other DNA
                         organism = synthetic construct
SEQUENCE: 196
caggtgcagc tgcaggagtc tgggggaggc ttggtgcggc ctgggggatc tctaagactc     60
tcctgtgaag cctctggaac caccttcaga agcctcgtaa tgaaatggta ccgccaggct   120
ccagggaagg agcgcgagtg ggtcgcattt atttctagtc ctggtgatcg cactcgctac   180
acagaagccg tgaagggccg attcaccatc tccagagaca atgccaagaa cgcgctgtat   240
ctgcaaatga acggcctgaa acctgaggac acggccgtgt attattgtaa cgcgaacgga   300
atatactggg gcaaagggac ccaggtcacc gtctccagcg gccgctaccc gtacgacgtt   360
ccggactacg gttccggccg agcatag                                        387

SEQ ID NO: 197           moltype = DNA   length = 393
FEATURE                  Location/Qualifiers
misc_feature             1..393
                         note = Generated by phage peptide display
source                   1..393
                         mol_type = other DNA
                         organism = synthetic construct
SEQUENCE: 197
caggtgcagc tgcaggagtc tgggggaggc ttggtgcaat ctgggggattc tctgagactc    60
tcctgtgcag cctctggatt caccttcagt aactatgcta tgagctgggt ccgccaggct   120
ccaggaaagg ggctcgagtg ggtctcaact attaatagtg gtggtgtag cacaagctat   180
gcgtactccg tgaagggccg attcaccatc tccagagaca acgccaagaa cacgctgtat   240
ctgcaaatga acagcctgaa acctgaggac acggccgtgt attactgtgc aaagacggcc   300
tctcacatac ccttgagcca ggggacccag gtcaccgtct ccagcggccg ctacccgtac   360
gacgttccgg actacggttc cggccgagca tag                                 393

SEQ ID NO: 198           moltype = DNA   length = 393
FEATURE                  Location/Qualifiers
misc_feature             1..393
                         note = Generated by phage peptide display
source                   1..393
                         mol_type = other DNA
                         organism = synthetic construct
SEQUENCE: 198
caggtgcagc tgcaggagtc tgggggaggc ttggtgcaac ctgggggttc tctgagactc     60
tcctgtgcag cctctggatt caccttcagt aactatgcta tgagctgggt ccgccaggct   120
ccaggaaagg ggctcgagtg ggtctcaact attaatattg gtggtggtag cacaagctat   180
gcagactccg tgaagggccg attcaccatc tccagagaca acgccaagaa cacgctgtat   240
ctgcaaatga acagcctgaa acctgaggac acggccgtgt attactgtgc aaagacggcc   300
tctcacatac ccttgagcca ggggacccag gtcaccgtct ccagcggccg ctacccgtac   360
gacgttccgg actacggttc cggccgagca tag                                 393

SEQ ID NO: 199           moltype = DNA   length = 399
FEATURE                  Location/Qualifiers
misc_feature             1..399
                         note = Generated by phage peptide display
source                   1..399
                         mol_type = other DNA
                         organism = synthetic construct
SEQUENCE: 199
caggtgcagc tgcaggagtc tgggggaggc ttggtgcaac ctgggggttc tctgagactc     60
tcctgtgcag cctctggatt caccttcagg aactatgcaa tgagctgggt ccgtcaggct   120
ccaggaaagg ggctcgagtg ggtctcaact attaatggtg gtggtggtat cacaagctat   180
gcagactccg tgaagggccg attcaccatc tccagagaca acgccaagaa cacaatgtat   240
ctgcaaatga acagcctgaa acctgaggac acggccgtgt attactgtgc ccaaaccgcc   300
cgcgattccc gcgattcccg gggccagggg acccaggtca ccgtctccag cggccgctac   360
ccgtacgacg ttccggacta cggttccggc cgagcatag                           399

SEQ ID NO: 200           moltype = DNA   length = 399
FEATURE                  Location/Qualifiers
misc_feature             1..399
                         note = Generated by phage peptide display
source                   1..399
                         mol_type = other DNA
                         organism = synthetic construct
SEQUENCE: 200
caggtgcagc tgcaggagtc tgggggaggc ttggtgcaac ctgggggttc tctgagactc     60
tcctgtgcag cctctggatt caccttcagt agctatgcta tgagctgggt ccgcctggct   120
ccaggaaagg ggctcgagtg ggtctcaact attaatatcg ctggtggtat cacaagctat   180
gcagactccg tgaagggccg attcaccatc tccagagaca acgccaagaa cacgctgtat   240
```

```
ctgcaaatga acagcctgaa acctgaggac acggccgtgt attactgtgc aaaaacggcg   300
gccaactgga gcgcccagag aggccagggg acccaggtca ccgtctccag cggccgctac   360
ccgtacgacg ttccggacta cggttccggc cgagcatag                          399
```

```
SEQ ID NO: 201          moltype = DNA   length = 399
FEATURE                 Location/Qualifiers
misc_feature            1..399
                        note = Generated by phage peptide display
source                  1..399
                        mol_type = other DNA
                        organism = synthetic construct
SEQUENCE: 201
caggtgcagc tgcaggagtc tgggggaggc ttggtgcaac ctggggttc tctgagactc     60
tcctgtgcag cctctggatt caccttcagt agctatgcta tgagttgggt ccgccaggct   120
ccaggaaagg ggctcgagtg ggtctcaact attaatatgg gtggtggtac cacaagtat   180
gcagactccg tgaagggccg attcaccatc tccagacaca acgccaagaa cacgctgtat   240
ctgcaaatga acagcctgaa acctgaggac acggccgtgt attactgtgc aaaaacggcg   300
ggcaactgga gcgcccagag aggccagggg acccaggtca ccgtctccag cggccgctac   360
ccgtacgacg ttccggacta cggttccggc cgagcatag                          399
```

```
SEQ ID NO: 202          moltype = DNA   length = 393
FEATURE                 Location/Qualifiers
misc_feature            1..393
                        note = Generated by phage peptide display
source                  1..393
                        mol_type = other DNA
                        organism = synthetic construct
SEQUENCE: 202
caggtgcagc tgcaggagtc tgggggaggc ttggtgcaac ctggggggttc tctgagactg   60
tcctgtgcag cctctggatt caccttcagt acaaagtgcca tgagttggat ccgccagcct   120
ccagggaagg cgcgcgaggt ggtcgcaact attactagtg ctggtggtag tataagttat   180
gtaaactccg tgaagggccg attcaccatc tccagacaca acgccaagaa cacgctgtat   240
ctgcaaatga acatgctgaa acctgaggac acggccgtgt attactgtgc ccgactggtc   300
aaccttgccc agaccggcca gggaacccag gtcaccgtct ccagcggccg ctaccccgtac   360
gacgttccgg actacggttc cggccgagca tag                                393
```

```
SEQ ID NO: 203          moltype = DNA   length = 393
FEATURE                 Location/Qualifiers
misc_feature            1..393
                        note = Generated by phage peptide display
source                  1..393
                        mol_type = other DNA
                        organism = synthetic construct
SEQUENCE: 203
caggtgcagc tgcaggagtc tgggggaggc ctggtgcaac ctggggggttc tctgagactg   60
tcctgtgcag cctctggatt caccttcagt acaaatgcca tgagttggat ccgccagcct   120
ccagggaagg cgcgcgaggt ggtcgcaact attactagtg ctggtggtag tataagttat   180
gtaaactccg tgaagggccg attcaccatc tccagacaca acgccaagaa cacgctgtat   240
ctgcaaatga acatgctgaa acctgaggac acggccgtgt attactgtgc ccgactggtc   300
aaccttgccc agaccggcca ggggacccag gtcaccgtct ccagcggccg ctaccccgtac   360
gacgttccgg actacggttc cggccgagca tag                                393
```

```
SEQ ID NO: 204          moltype = AA    length = 130
FEATURE                 Location/Qualifiers
REGION                  1..130
                        note = Generated by phage peptide display
source                  1..130
                        mol_type = protein
                        organism = synthetic construct
SEQUENCE: 204
QVQLQESGGG MVEPGGSLRL SCAASGFRFS SYAMSWVRQA PGKGLERVSA INSDGDKTSY    60
ADSVKGRFTI SRDNARNTLY LQMSNLKPED TAVYYCADRD LYCSGSMCKD VLGGARYDFR   120
GQGTQVTVSS                                                          130
```

```
SEQ ID NO: 205          moltype = AA    length = 130
FEATURE                 Location/Qualifiers
REGION                  1..130
                        note = Generated by phage peptide display
source                  1..130
                        mol_type = protein
                        organism = synthetic construct
SEQUENCE: 205
QVQLQESGGG LVEPGGSLRL SCAASGFRFS SYAMSWVRQA PGKGLERVSA INSDGDKTSY    60
ADSVKGRFTI SRDNARNTLY LQMSNLKPED TAVYYCADRD LYCSGSMCKD VLGGARYDFR   120
GQGTQVTVSS                                                          130
```

```
SEQ ID NO: 206          moltype = AA    length = 130
FEATURE                 Location/Qualifiers
REGION                  1..130
```

```
                        note = Generated by phage peptide display
source                  1..130
                        mol_type = protein
                        organism = synthetic construct
SEQUENCE: 206
QVQLQESGGG MVEPGGSRLR LSCAASGFRFS SYAMSWVRQA PGKGLERVSA INSDGDKTSY    60
ADSVKGRFTI SRDNARNTLY LQMNNLKPED TAVYYCADRD LYCSGSMCKD VLGGARYDFR   120
GQGTQVTVSS                                                          130

SEQ ID NO: 207          moltype = AA   length = 130
FEATURE                 Location/Qualifiers
REGION                  1..130
                        note = Generated by phage peptide display
source                  1..130
                        mol_type = protein
                        organism = synthetic construct
SEQUENCE: 207
QVQLQESGGG LVQSGESLRL SCAASGLRFS SYAMSWVRQA PGKGLERVSA INSDGDKTSY    60
ADSVKGRFTI SRDNARNTLY LQMSNLKPED TAVYYCADRD LYCSGSMCKD VLGGARYDFR   120
GQGTQVTVSS                                                          130

SEQ ID NO: 208          moltype = AA   length = 123
FEATURE                 Location/Qualifiers
REGION                  1..123
                        note = Generated by phage peptide display
source                  1..123
                        mol_type = protein
                        organism = synthetic construct
SEQUENCE: 208
QVQLQESGGG LVQPGGSLKL SCAASGFTFN WYTMAWYRQV PGEERKMVAT ITGASGDTKY    60
ADSVKGRFTI SRDNAKNTVT LQMNSLKPGD AAVYYCHAYL TYDSGSVKGV NYWGQGTQVT   120
VSS                                                                 123

SEQ ID NO: 209          moltype = AA   length = 123
FEATURE                 Location/Qualifiers
REGION                  1..123
                        note = Generated by phage peptide display
source                  1..123
                        mol_type = protein
                        organism = synthetic construct
SEQUENCE: 209
QVQLQESGGG LVRPGGSLKL SCAASGFTFN WYTMAWYRQV PGEERKMVAT ITGASGDTKY    60
ADSVKGRFTI SRDNAKNTVT LQMNSLKPGD TAVYYCHAYL TYDSGSVKGV NYWGQGTQVT   120
VSS                                                                 123

SEQ ID NO: 210          moltype = AA   length = 123
FEATURE                 Location/Qualifiers
REGION                  1..123
                        note = Generated by phage peptide display
source                  1..123
                        mol_type = protein
                        organism = synthetic construct
SEQUENCE: 210
QVQLQESGGG SVQPGGSLKL SCAASGFTFN WYTMAWYRQV PGEERKMVAT ITGASGDTKY    60
ADSVKGRFTI SRDNAKNTVT LQMNSLKPGD TAVYYCHAYL TYDSGSVKGV NYWGQGTQVT   120
VSS                                                                 123

SEQ ID NO: 211          moltype = AA   length = 123
FEATURE                 Location/Qualifiers
REGION                  1..123
                        note = Generated by phage peptide display
source                  1..123
                        mol_type = protein
                        organism = synthetic construct
SEQUENCE: 211
QVQLQESGGG SVQPGGSLKL SCAASGFTFN WYTMAWYRQV PGEERKMVAT ITGASGDTKY    60
ADSVKGRSTI SRDNAKNTVT LQMNSLKPGD TAVYYCHACL TYDSGSVKGV NYWGQGTQVT   120
VSS                                                                 123

SEQ ID NO: 212          moltype = AA   length = 123
FEATURE                 Location/Qualifiers
REGION                  1..123
                        note = Generated by phage peptide display
source                  1..123
                        mol_type = protein
                        organism = synthetic construct
SEQUENCE: 212
QVQLQESGGG FVQPGGSLKL SCAASGFTFN WYTMAWYRQV PGEERKMVAT ITGASGDTKY    60
ADSVKGRFTI SRDNAKNTVT LQMNSLKPGD TAVYYCHAYL TYDSGSVKGV NYWGQGTQVT   120
```

```
VSS                                                                  123

SEQ ID NO: 213          moltype = AA  length = 123
FEATURE                 Location/Qualifiers
REGION                  1..123
                        note = Generated by phage peptide display
source                  1..123
                        mol_type = protein
                        organism = synthetic construct
SEQUENCE: 213
QVQLQESGGG LVQPGGSLKL SCAASGFTFN WYTMAWYRQV PGEERKMVAT ITGASGDTKY     60
ADSVKGRFTI SRDNAKNTVT LQMNSLKPGD TAVYYCHAYL TYDSGSAKGV NYWGQGTQVT    120
VSS                                                                  123

SEQ ID NO: 214          moltype = AA  length = 124
FEATURE                 Location/Qualifiers
REGION                  1..124
                        note = Generated by phage peptide display
source                  1..124
                        mol_type = protein
                        organism = synthetic construct
SEQUENCE: 214
QVQLQESGGG LVQPGGSLGL SCAASGSLLN IYAMGWYRQA PGRQRELVAT VTSSGTAEYA     60
DSVKGRFTIS RDNAKNTVYL QMNSLRPEDT GVYYCNAHLR YGDYVRGPPE YNWGQGTQV     120
TVSS                                                                 124

SEQ ID NO: 215          moltype = AA  length = 129
FEATURE                 Location/Qualifiers
REGION                  1..129
                        note = Generated by phage peptide display
source                  1..129
                        mol_type = protein
                        organism = synthetic construct
SEQUENCE: 215
QVQLQESGGG LVQPGGSLRL SCAASGGTLG YYAIGWFRQA PGKEREAVSC ITSSDTSAYY     60
ADSAKGRFTI SRDNAKNTMY LQMNNLKPED TAVYYCAAGY YFRDYSDSYY YTGTGMKVWG    120
KGTQVTVSS                                                            129

SEQ ID NO: 216          moltype = AA  length = 129
FEATURE                 Location/Qualifiers
REGION                  1..129
                        note = Generated by phage peptide display
source                  1..129
                        mol_type = protein
                        organism = synthetic construct
SEQUENCE: 216
QVQLQESGGG LVQPGGSTRL SCAASGFTLD IYAIGWFRQA PGKEHEGVSW IVGNDGRTYY     60
IDSVKGRFTI SRDNAKNTVY LEMNSLKPED TAVYYCAAKF WPRYYSGRPP VGRDGYDYWG    120
QGTQVTVSS                                                            129

SEQ ID NO: 217          moltype = AA  length = 111
FEATURE                 Location/Qualifiers
REGION                  1..111
                        note = Generated by phage peptide display
source                  1..111
                        mol_type = protein
                        organism = synthetic construct
SEQUENCE: 217
QVQLQESGGG LVQPGGSLIL SCTISGASLR DRRVTWSRQG PGKSLEIIAV MAPDYGVHYF     60
GSLEGRVAVR GDVVKNTVYL QVNALKPEDT AIYWCSMGNI RGLGTQVTVS S             111

SEQ ID NO: 218          moltype = DNA  length = 438
FEATURE                 Location/Qualifiers
misc_feature            1..438
                        note = Generated by phage peptide display
source                  1..438
                        mol_type = other DNA
                        organism = synthetic construct
SEQUENCE: 218
caggtgcagc tgcaggagtc tgggggaggc atggtagaac ctgggggttc tctgagactc     60
tcctgtgcag cctctggatt ccgcttcagt agttatgcta tgagttgggt ccgccaggct    120
ccaggaaagg ggctcgagcg ggtctcggct attaatagtg atggtgataa acaagctat     180
gcagactccg tgaagggccg atttaccatc tccagagaca cgccaggaa cacgctgtat     240
ctgcaaatga gcaacctgaa acctgaagac acggccgtgt attactgtgc agaccggagat    300
ttgtactgtt caggctctat gtgtaaggac gtcttggggg gagcacgcta tgactttcgg    360
ggccagggga cccaggtcac cgtctccagc ggccgctacc cgtacgacgt tccggactac    420
ggttccggcc gagcatag                                                  438

SEQ ID NO: 219          moltype = DNA  length = 438
```

| FEATURE | Location/Qualifiers |
|---|---|
| misc_feature | 1..438 |
| | note = Generated by phage peptide display |
| source | 1..438 |
| | mol_type = other DNA |
| | organism = synthetic construct |

SEQUENCE: 219

```
caggtgcagc tgcaggagtc tggaggaggc ttggtagaac ctgggggttc tctgagactc    60
tcctgtgcag cctctggatt ccgcttcagt agttatgcta tgagttgggt ccgccaggct   120
ccaggaaagg ggctcgagcg ggtctcagct attaatagtg atggtgataa aacaagctat   180
gcagactccg tgaagggccg atttaccatc tccagagaca acgccaggaa cacgctgtat   240
ctgcaaatga gcaacctgaa acctgaagac acggccgtgt attactgtgc agaccgagat   300
ttgtactgtt caggctctat gtgtaaggac gtcttggggg agcacgcta tgactttcgg   360
ggccagggga cccaggtcac cgtctccagc ggccgctacc cgtacgacgt tccggactac   420
ggttccggcc gagcatag                                                 438
```

| SEQ ID NO: 220 | moltype = DNA   length = 438 |
|---|---|
| FEATURE | Location/Qualifiers |
| misc_feature | 1..438 |
| | note = Generated by phage peptide display |
| source | 1..438 |
| | mol_type = other DNA |
| | organism = synthetic construct |

SEQUENCE: 220

```
caggtgcagc tgcaggagtc tggggggaggc atggtagaac ctgggggttc tctgagactc    60
tcctgtgcag cctctggatt ccgcttcagt agttatgcta tgagttgggt ccgccaggct   120
ccaggaaagg ggctcgagcg ggtctcggct attaatagtg atggtgataa aacaagctat   180
gcagactccg tgaagggccg attcaccatc tccagagaca acgccaggaa cacgctgtat   240
ctgcaaatga acaacctgaa acctgaagac acggccgtgt attactgtgc agaccgagat   300
ttgtactgtt cgggctctat gtgtaaggac gtcttggggg agcacgcta tgactttcgg   360
ggccagggga cccaggtcac cgtctccagc ggccgctacc cgtacgacgt tccggactac   420
ggttccggcc gagcatag                                                 438
```

| SEQ ID NO: 221 | moltype = DNA   length = 438 |
|---|---|
| FEATURE | Location/Qualifiers |
| misc_feature | 1..438 |
| | note = Generated by phage peptide display |
| source | 1..438 |
| | mol_type = other DNA |
| | organism = synthetic construct |

SEQUENCE: 221

```
caggtgcagc tgcaggagtc tggggggaggc ttggtgcagt ctggcgagtc tctcagactc    60
tcctgtgcag cctctggact ccgcttcagt agttatgcta tgagttgggt ccgccaggct   120
ccaggaaagg ggctcgagcg ggtctcggct attaatagtg atggtgataa aacaagctat   180
gcagactccg tgaagggccg atttaccatc tccagagaca acgccaggaa cacgctgtat   240
ctgcaaatga gcaacctgaa acctgaagac acggccgtgt attactgtgc agaccgagat   300
ttgtactgtt caggctctat gtgtaaggac gtcttggggg agcacgcta tgactttcgg   360
ggccagggga cccaggtcac cgtctccagc ggccgctacc cgtacgacgt tccggactac   420
ggttccggcc gagcatag                                                 438
```

| SEQ ID NO: 222 | moltype = DNA   length = 417 |
|---|---|
| FEATURE | Location/Qualifiers |
| misc_feature | 1..417 |
| | note = Generated by phage peptide display |
| source | 1..417 |
| | mol_type = other DNA |
| | organism = synthetic construct |

SEQUENCE: 222

```
caggtgcagc tgcaggagtc tggaggaggc ctggtgcagc ctgggggggtc tctgaaactc    60
tcctgtgcag cctctggatt caccttcaat tggtatacca tggcctggta tcgccaggtt   120
ccaggggagg agcgcaaaat ggtcgccaca attacaggtg ctagtggtga cacaaaatat   180
gcagactccg tgaagggccg gttcaccatc tccagagaca atgccaagaa cacggtgaca   240
ctgcaaatga acagccttaa acctggagac acggccgtct attactgtca tgcctaccta   300
acctacgact cggggtccgt caaaggagtt aactactggg gccaggggac ccaggtcacc   360
gtctccagcg gccgctaccc gtacgacgtt ccggactacg gttccggccg agcatag      417
```

| SEQ ID NO: 223 | moltype = DNA   length = 417 |
|---|---|
| FEATURE | Location/Qualifiers |
| misc_feature | 1..417 |
| | note = Generated by phage peptide display |
| source | 1..417 |
| | mol_type = other DNA |
| | organism = synthetic construct |

SEQUENCE: 223

```
caggtgcagc tgcaggagtc tggggggaggc ttggtgcggc ctggggggtc tctgaaactc    60
tcctgtgcag cctctggatt caccttcaat tggtatacca tggcctggta tcgccaggtt   120
ccaggggagg agcgcaaaat ggtcgccaca attacaggtg ctagtggtga cacaaaatat   180
gcagactccg tgaagggccg gttcaccatc tccagagaca atgccaagaa cacggtgaca   240
ctgcaaatga acagccttaa acctggagac acggccgtct attactgtca tgcctaccta   300
```

```
acctacgact cggggtccgt caaaggagtt aactactggg gccaggggac ccaggtcacc   360
gtctccagcg gccgctaccc gtacgacgtt ccggactacg gttccggccg agcatag     417

SEQ ID NO: 224          moltype = DNA  length = 417
FEATURE                 Location/Qualifiers
misc_feature            1..417
                        note = Generated by phage peptide display
source                  1..417
                        mol_type = other DNA
                        organism = synthetic construct
SEQUENCE: 224
caggtgcagc tgcaggagtc tgggggaggc tcggtgcagc ctgggggtc tctgaaactc    60
tcctgtgcag cctctggatt caccttcaat tggtatacca tggcctggta tcgccaggtt  120
ccaggggagg agcgcaaaat ggttgccaca attacaggtg ctagtggtga cacaaaatat  180
gcagactccg tgaagggccg gttcaccatc tccagagaca atgccaagaa cacggtgaca  240
ctgcaaatga acagccttaa acctggagac acggccgtct attactgtca tgcctaccta  300
acctacgact cggggtccgt caaaggagtt aactactggg gccaggggac ccaggtcacc  360
gtctccagcg gccgctaccc gtacgacgtt ccggactacg gttccggccg agcatag     417

SEQ ID NO: 225          moltype = DNA  length = 417
FEATURE                 Location/Qualifiers
misc_feature            1..417
                        note = Generated by phage peptide display
source                  1..417
                        mol_type = other DNA
                        organism = synthetic construct
SEQUENCE: 225
caggtgcagc tgcaggagtc tgggggaggc tcggtgcagc ctgggggtc tctgaaactc    60
tcctgtgcag cctctggatt caccttcaat tggtatacca tggcctggta tcgccaggtt  120
ccaggggagg agcgcaaaat ggtcgccaca attacaggtg ctagtggtga cacaaaatat  180
gcagactccg tgaagggccg gtccaccatc tccagagaca atgccaagaa cacggtgaca  240
ctgcaaatga acagccttaa acctggagac acggccgtct attactgtca tgcctgccta  300
acctacgact cggggtccgt caaaggagtt aactactggg gtcaggggac ccaggtcacc  360
gtctccagcg gccgctaccc gtacgacgtt ccggactacg gttccggccg agcatag     417

SEQ ID NO: 226          moltype = DNA  length = 417
FEATURE                 Location/Qualifiers
misc_feature            1..417
                        note = Generated by phage peptide display
source                  1..417
                        mol_type = other DNA
                        organism = synthetic construct
SEQUENCE: 226
caggtgcagc tgcaggagtc tgggggaggc ttcgtgcagc ctgggggtc tctgaaactc    60
tcctgtgcag cctctggatt caccttcaat tggtatacca tggcctggta tcgccaggtt  120
ccaggggagg agcgcaaaat ggtcgccaca attacaggtg ctagtggtga cacaaaatat  180
gcagactccg tgaagggccg gttcaccatc tccagagaca atgccaagaa cacggtgaca  240
ctgcaaatga acagccttaa acctggagac acggccgtct attactgtca tgcctaccta  300
acctacgact cggggtccgt caaaggagtt aactactggg gccaggggac ccaggtcacc  360
gtctccagcg gccgctaccc gtacgacgtt ccggactacg gttccggccg agcatag     417

SEQ ID NO: 227          moltype = DNA  length = 417
FEATURE                 Location/Qualifiers
misc_feature            1..417
                        note = Generated by phage peptide display
source                  1..417
                        mol_type = other DNA
                        organism = synthetic construct
SEQUENCE: 227
caggtgcagc tgcaggagtc tgggggaggc ctggtgcagc ctgggggtc tctgaaactc    60
tcctgtgcag cctctggatt caccttcaat tggtatacca tggcctggta tcgccaggtt  120
ccaggggagg agcgcaaaat ggtcgccaca attacaggtg ctagtggtga cacaaaatat  180
gcagactccg tgaagggccg gttcaccatc tccagagaca atgccaagaa cacggtgaca  240
ctgcaaatga acagccttaa acctggagac acggccgtct attactgtca tgcctaccta  300
acctacgact cggggtccgc caaaggagtt aactactggg gccaggggac ccaggtcacc  360
gtctccagcg gccgctaccc gtacgacgtt ccggactacg gttccggccg agcatag     417

SEQ ID NO: 228          moltype = DNA  length = 420
FEATURE                 Location/Qualifiers
misc_feature            1..420
                        note = Generated by phage peptide display
source                  1..420
                        mol_type = other DNA
                        organism = synthetic construct
SEQUENCE: 228
caggtgcagc tgcaggagtc tgggggaggc ttggtgcagc ctgggggtc tctaggactc    60
tcctgtgcag cctctggaag cctcttaaat atctatgcca tgggctggta ccgccaggct  120
ccagggagac agcgcgagtt ggtcgcaact gtaacgagta gtggaaccgc agaatatgca  180
gactccgtga agggccgatt caccatctct agagacaacg ccaagaacac ggtgtatctg  240
```

```
caaatgaaca gcctgagacc tgaggacacg ggcgtctatt actgtaatgc acatctcaga    300
tatgcgact  atgtccgtgg ccctccggag tataactact ggggccaggg gacccaggtc    360
accgtctcca gcggccgcta cccgtacgac gttccggact acggttccgg ccgagcatag   420

SEQ ID NO: 229           moltype = DNA  length = 435
FEATURE                  Location/Qualifiers
misc_feature             1..435
                         note = Generated by phage peptide display
source                   1..435
                         mol_type = other DNA
                         organism = synthetic construct
SEQUENCE: 229
caggtgcagc tgcaggagtc tgggggaggc ttggtgcagc ctggggggtc tctgagactc    60
tcctgtgcag cctctggagg cactttgggt tactatgcca taggctggtt ccgccaggcc   120
ccagggaagg agcgcgaggc ggtctcctgt attactagta gtgacactag cgcatactat   180
gcagactccg cgaagggccg attcaccatc tccagagaca acgccaagaa cacgatgtat   240
ctgcaaatga acaacctgaa acctgaggac acagccgttt attactgtgc agccggttac   300
tattttagag actatagtga cagttactac tacacgggga cgggtatgaa agtctggggc   360
aaagggaccc aggtcaccgt ctccagcggc cgctacccgt acgacgttcc ggactacggt   420
tccggccgag catag                                                    435

SEQ ID NO: 230           moltype = DNA  length = 435
FEATURE                  Location/Qualifiers
misc_feature             1..435
                         note = Generated by phage peptide display
source                   1..435
                         mol_type = other DNA
                         organism = synthetic construct
SEQUENCE: 230
caggtgcagc tgcaggagtc tgggggaggc ttggtgcagc ctggggggtc tacgagactc    60
tcctgtgcag cctctggatt cactttggat atttatgcta taggctggtt ccgccaggcc   120
ccagggaagg agcatgaggg ggtctcgtgg attgttggta atgatggtag gacatactac   180
atagactccg tgaagggccg attcaccatc tccagagaca acgccaagaa cacggtgtat   240
cttgaaatga acagcctgaa acctgaggat acagccgttt attactgcgc agctaagttc   300
tggccccgat attatagtgg taggcctcca gtagggaggg atggctatga ctattgggc    360
caggggaccc aggtcaccgt ctccagcggc cgctacccgt acgacgttcc ggactacggt   420
tccggccgag catag                                                    435

SEQ ID NO: 231           moltype = DNA  length = 381
FEATURE                  Location/Qualifiers
misc_feature             1..381
                         note = Generated by phage peptide display
source                   1..381
                         mol_type = other DNA
                         organism = synthetic construct
SEQUENCE: 231
caggtgcagc tgcaggagtc tgggggaggc ttggtgcagc ctggcgggtc tctgatactc    60
tcctgtacaa tctcgggagc ctcgctccga gaccgacgcg tcacctgagg tcgccaaggt   120
ccagggaaat cgcttgagat catcgcagtt atggcgccgg attacggggt ccattacttt   180
ggctccctgg aggggcgagt tgccgtccga ggagacgtcg tcaagaatac agtatatctc   240
caagtaaacg ccctgaaacc cgaagacaca gccatctatt ggtgcagtat ggggaatatc   300
cggggcctgg ggacccaggt caccgtctcc agcggccgct acccgtacga cgttccggac   360
tacggttccg gccgagcata g                                             381
```

What is claimed is:

1. A single-domain antibody against *Yersinia pestis* (*Y. pestis*) SAb protein comprising:
   a first framing region ("FR") sequence comprising SEQ ID No:79;
   a first complementarity determining region ("CDR") sequence comprising SEQ ID No:1;
   a second FR sequence comprising SEQ ID No: 103, the first CDR sequence being positioned between the first FR sequence and the second FR sequence;
   a second CDR sequence comprising SEQ ID No:27;
   a third FR sequence comprising SEQ ID No: 121, the second CDR sequence being positioned between the second FR sequence and the third FR sequence;
   a third CDR sequence comprising SEQ ID No.54; and
   a fourth FR sequence comprising SEQ ID No:147, the third CDR sequence being positioned between the third FR sequence and the fourth FR sequence.

2. The single-domain antibody of claim 1, wherein the single-domain antibody further comprises:
   at least one of a protein tag, a protein domain tag, or a chemical tag.

* * * * *